(12) United States Patent
Larisch

(10) Patent No.: US 11,230,579 B2
(45) Date of Patent: Jan. 25, 2022

(54) METHOD OF TREATING BCL-2 OVER-EXPRESSING DISORDERS USING ARTS CONTAINING A BH3-LIKE DOMAIN

(71) Applicant: CARMEL-HAIFA UNIVERSITY ECONOMIC CORPORATION LTD., Haifa (IL)

(72) Inventor: Sarit Larisch, Zichron Yaakov (IL)

(73) Assignee: CARMEL-HAIFA UNIVERSITY ECONOMIC CORPORATION LTD., Haifa (IL)

( * ) Notice: Subject to any disclaimer, the term of this patent is extended or adjusted under 35 U.S.C. 154(b) by 0 days.

(21) Appl. No.: 15/372,842

(22) Filed: Dec. 8, 2016

(65) Prior Publication Data

US 2017/0081380 A1    Mar. 23, 2017

Related U.S. Application Data

(63) Continuation of application No. 14/378,719, filed as application No. PCT/IL2013/050138 on Feb. 14, 2013, now abandoned.

(60) Provisional application No. 61/598,953, filed on Feb. 15, 2012.

(51) Int. Cl.
| | |
|---|---|
| *A61K 38/10* | (2006.01) |
| *A61K 38/17* | (2006.01) |
| *C07K 14/47* | (2006.01) |
| *G01N 33/68* | (2006.01) |
| *A61K 38/00* | (2006.01) |

(52) U.S. Cl.
CPC ......... *C07K 14/4747* (2013.01); *G01N 33/68* (2013.01); *G01N 33/6893* (2013.01); *A61K 38/00* (2013.01); *G01N 2333/4704* (2013.01); *G01N 2510/00* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 7,423,115 | B2* | 9/2008 | Larisch | C07K 14/4747 |
| | | | | 530/328 |
| 8,455,540 | B2* | 6/2013 | Mortier | C07C 41/30 |
| | | | | 514/453 |
| 2003/0124571 | A1 | 7/2003 | Larisch et al. | |

FOREIGN PATENT DOCUMENTS

| | | |
|---|---|---|
| WO | 2003013422 A2 | 2/2003 |
| WO | 2005074381 A2 | 8/2005 |
| WO | 2006126198 A2 | 11/2006 |

(Continued)

OTHER PUBLICATIONS

Chen et al., Differntial targeting of prosurvival Bcl-2 proteins by their BH3-only ligands allows complemtary apoptotic funcion, Mol. Cell, 17:393-403, Feb. 4, 2005.*

(Continued)

*Primary Examiner* — Claire Kaufman
(74) *Attorney, Agent, or Firm* — Browdy and Neimark, PLLC

(57) ABSTRACT

The present invention provides an antagonist of a Bcl-2 prosurvival protein containing a BH3-like domain. The antagonist of the invention comprises ARTS and any fragment or peptide that comprises a BH3-like domain. The invention further provides compositions, combined compositions and kits as well as methods for treating Bcl-2 over-expressing disorders.

16 Claims, 20 Drawing Sheets

Specification includes a Sequence Listing.

(56) References Cited

FOREIGN PATENT DOCUMENTS

| WO | 2010042225 A2 | 4/2010 |
| WO | 2010068684 A2 | 6/2010 |

OTHER PUBLICATIONS

Masood et al., Small molecule inhibitors of Bcl-2 family proteins for pancreatic cancer therapy, Cancers, 3(2):1527-1549, 2011.*

GenBank Database, Accession No. NP_001271321, septin-4 isoform 2 [Mus musculus], Retrieved Online fromURL< https://www.ncbi.nlm.nih.gov/protein/NP_001271321>, Retrieved on Jul. 25, 2019, Jul. 7, 2019.*

Edison et al., Degradation of Bcl-2 by XIAP and ARTS promotes apoptosis, Cell Rep. 21(2):442-454, Oct. 10, 2017.*

Koren et al., <span style="font-family: "Windows Arial Unicode";">RTS mediates apoptosis and regeneration of the intestinal stem cell niche, Nat. Comm. 9:4582., Retrieved online Jul. 22, 2019. Retrieved from: URL<http://DOI:.org/10.1038/s41467-018-06941-4 >. </span> Nov. 2, 2018.*

Accession No. C9JT15 in UNIPROTKB/TrEMBL Database for "SubName: Full-Septin-2 . . . " Nov. 3, 2009, referencing Ladeana W. Hillier et al., Nature 434:724-731 (2005).

Fuchs et al "Programmed Cell Death in Animal Development and Disease" Cell. 147:1-17 (2011).

Gottfried et al., "The mitochondrial ARTS protein promotes apoptosis through targeting XIAP" EMBO J. 23:1627-1635 (2004).

Edison et al. "Peptides Mimicking the Unique ARTS-XIAP Binding Site Promote Apoptotic Cell Death in Cultured Cancer Cell" Clin Cancer Res 2569-2578 (2012a).

Bornstein et al. ARTS binds to a distinct domain in XIAP-BIR3 and promotes apoptosis by a mechanism that is different from other IAP-antagonists. Apoptosis 16:869-881 (2011).

Reingewertz et al., "Mechanism of the interaction between the intrinsically disordered C-Terminus of the Pro-Apoptotic ARTS Protein and the Bir3 Domain of XIAP" PLoS One. 6 (9) e24655 : 1-10 (Sep. 2011).

Adams et al. "Life-or-death decisions by the Bcl-2 protein family" Trends Biochem Sci. 26 (1) 61-66 (Jan. 2001).

Youle et al "The BCL-2 protein family: opposing activities that mediate cell death" Nat Rev Mol Cell Biol. 9:47-59 (Jan. 2008).

Happo et al., "BH3-ONLY Proteins in Apoptosis at a Glance" J Cell Sci. 125:1081-1087 (2012).

Robertson et al., "Bcl-2 expression in chronic lymphocytic leukemia and its correlation with the induction of apoptosis and clinical outcome" Leukemia. 10:456-459 (1996).

Oltersdorf et al., "An inhibitor of Bcl-2 family proteins induces regression of solid tumors" Nature. 435:677-681 (Jun. 2005).

Schile et al., "Regulation of apoptosis by XIAP ubiquitin-ligase activity" M. Genes Dev. 22:2256-2266 (Jun. 2008).

Lotan et al., "Regulation of the Proapoptotic ARTS Protein by Ubiquitin-mediated Degradation" J Biol Chem. 280:25802-25810 (Jul. 2005).

Kerppola et al "Design and Implementation of Bimolecular Flurescence Complementation (BiFC) Assays for the Visualization of Protein Interactions in Living Cells" Nat Protoc. 1 (3) 1278-1286 (2006).

Bader et al "Regulation of cell death by the ubiquitin-proteasome system" Curr Opin Cell Biol. 21:878-884 (2009).

Kaufmann et al. "Characterization of the signal that directs Bcl-xL, but not Bcl-2, to the mitochondrial outer membrane" J Cell Biol. 160 (1) 53-64 (Jan. 2003).

Garcia-Fernandez et al., "Sept4/ARTS is required for stem cell apoptosis and tumor suppression" Genes Dev. 24:2282-2293 (2010).

Kissel et al "The Sept4 Septin Locus Is Required for Sperm Terminal Differentiation in Mice" Dev Cell. 8:353-364 (Mar. 2005).

Edison et al., "The IAP-antagonist ARTS initiates caspase activation upstream of cytochrome C and SMAC/Diablo" Cell Death Differ. 19:356-368 (2012b).

Garrison et al., "ARTS and Siah Collaboration in a Pathway for XIAP Degradation" Mol Cell. 41:107-116 (2010).

Bornstein et al., "X-linked Inhibitor of Apoptosis Protein promotes the degradation of its antagonist, the pro-apoptotic ARTS protein" Int J Biochem Cell Biol. 44:489-495 (2011).

Larishch et al., "A novel mitochondrial septin-like protein, arts, mediates apoptosis dependsents on its P-loop motif" Nat Cell Biol. 2:915-221 (2000).

Larisch, et al., "Homo sapiens . . . product, " NCBI Genbank AF:176379.1 (submitted Aug. 4, 1999; accessed Oct. 22, 2014).

Kim et al., "Apoptosis regulator Bcl-2 alpha isoform {Homo sapiens}." GenBank Accession No. NP_000624. (accessed Oct. 22, 2014).

Kim et al "Apoptosis regulator Bcl-2 alpha isoform {Homo sapiens}." GenBank Accession No. NP_000648 (accessed Oct. 22, 2014).

Kim et al "Homo sapiens B-cell CLL/lymphoma 2 (BCL2), transcript variant alpha, mRNA." GenBank Accession No. NM_000633 (accessed Oct. 22, 2014).

Kim et al "Homo sapiens B-cell CLL/lymphoma 2 (BCL2), transcript variant beta, mRNA." GenBank Accession No. NM_000657. (accessed Oct. 22, 2014).

Boise et al "bcl-xL [Homo sapiens]." GenBank Accession No. CAA80661. (submitted Jun. 22, 1993; accessed Oct. 22, 2014).

Boise et al "H.sapiens bcl-xL mRNA." GenBank Accession No. Z23115. (submitted Jun. 22, 1993; accessed Oct. 22, 2014).

Wang et al "E3 ubiquitin-protein ligase XIAP [Homo sapiens]." GenBank Accession No. NP_001158 (accessed Oct. 22, 2014).

Wang et al "Homo sapiens X-linked inhibitor of apoptosis (XIAP), transcript variant 1, mRNA." GenBank Accession No. NM_001167. (accessed Oct. 22, 2014).

Winkler et al "E3 ubiquitin-protein ligase XIAP [Homo sapiens]." GenBank Accession No. NP_001191330. (accessed Oct. 22, 2014).

Winkler et al "Homo sapiens X-linked inhibitor of apoptosis, E3 ubiquitin protein ligase (XIAP), transcript variant 2, mRNA." GenBank Accession No. NM_001204401 (accessed Oct. 22, 2014).

Lotan et al "Regulation of the Proapoptotic ARTS Protein by Ubiquitin-mediated Degradation" J. Biol. Chem. 280:25802-25810 (2005).

Tse et al "ABT-263: A Potent and Orally Bioavailable Bcl-2 Family Inhibitor" Cancer Res. 68 : 9 (2008).

Giam et al., BH3-only proteins and their roles in programmed cell death, Oncogene, 27:S128-S136, 2009.

GenBank Accession No. NP 001271321, Septin-4 isoform 2 [Mus musculus], [Retrieved Jun. 2, 2016], Feb. 15, 2015.

Imazu et al., Bci-2/E1 B 19 Da-interacting protein 3-like protein (Bnip3L) interacts with Bci-2/Bcl-xl and induces apoptosis by altering mitochondria membrane permeability, Oncogene 8:4523-4529, 1999.

Gandhi et al., Phase I study of navitoclax (ABT-263), a novel Bcl-2 family inhibitor, in patients with small-cell lung cancer and other solid tumors, J. Clin. Oncol. 29(7):909-916, Mar. 1, 2011.

* cited by examiner

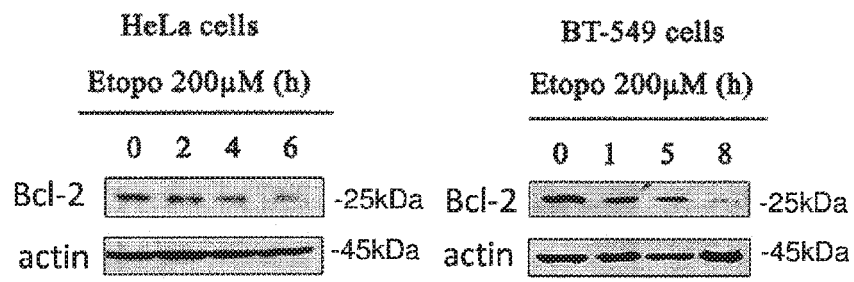
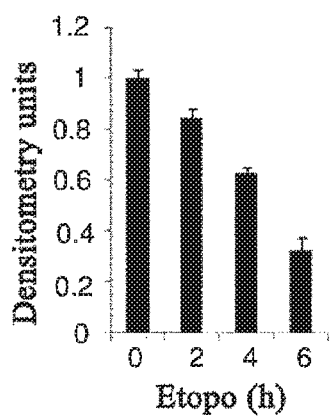
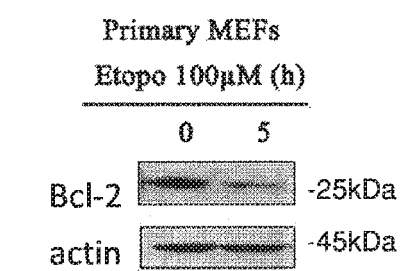
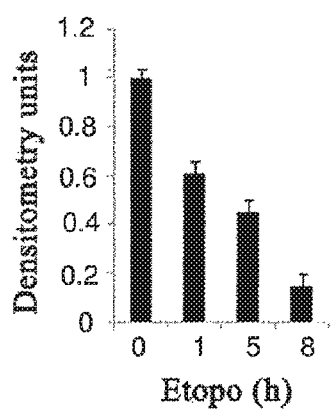
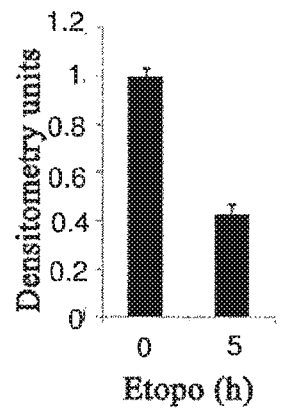
Figure 1G  Figure 1H  Figure 1I  Figure 1J  Figure 1K  Figure 1L

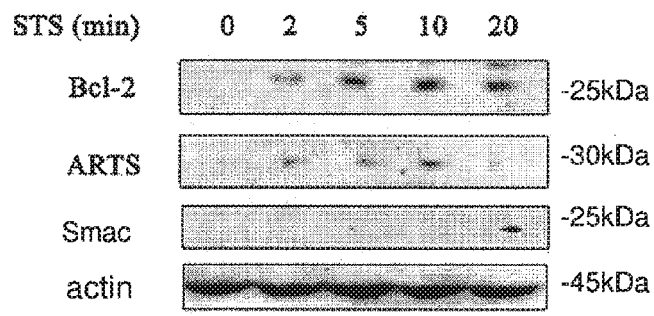
Figure 3D
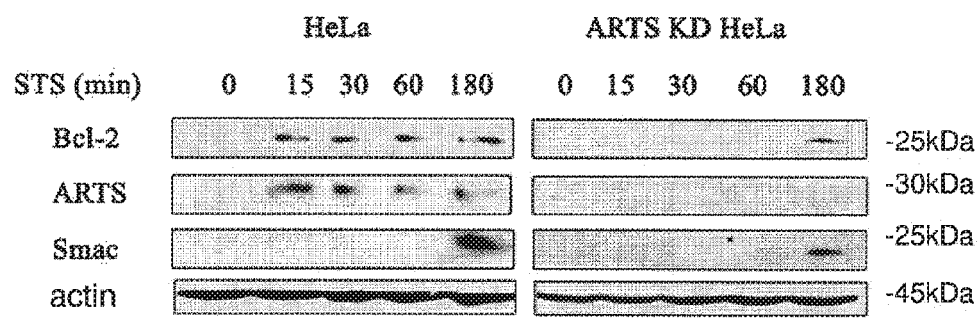
Figure 3E          Figure 3F
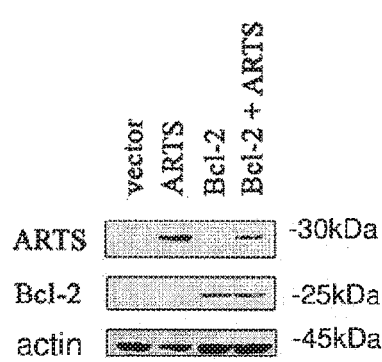      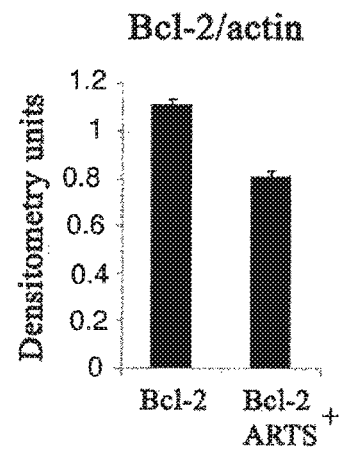
Figure 3G          Figure 3H

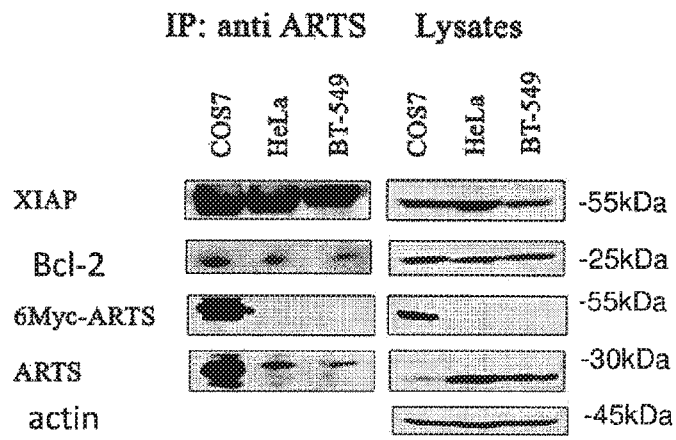
Figure 4B
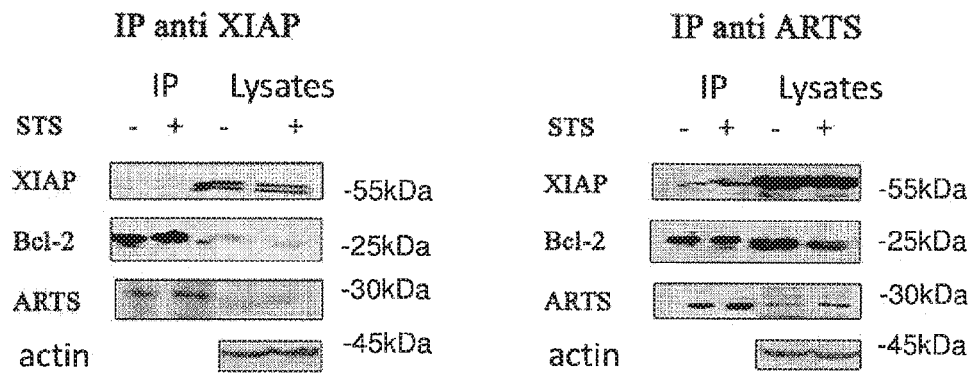
Figure 4C
Figure 4D

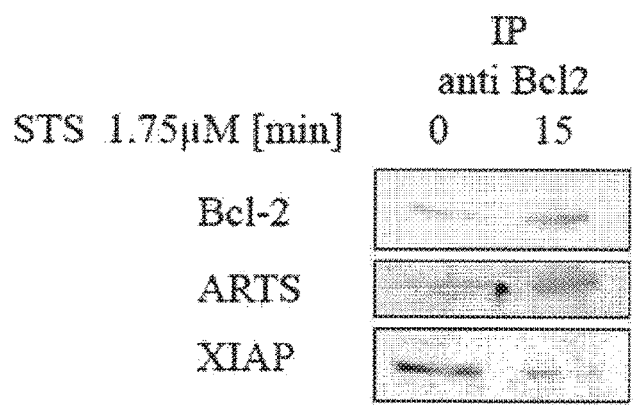
Figure 4E
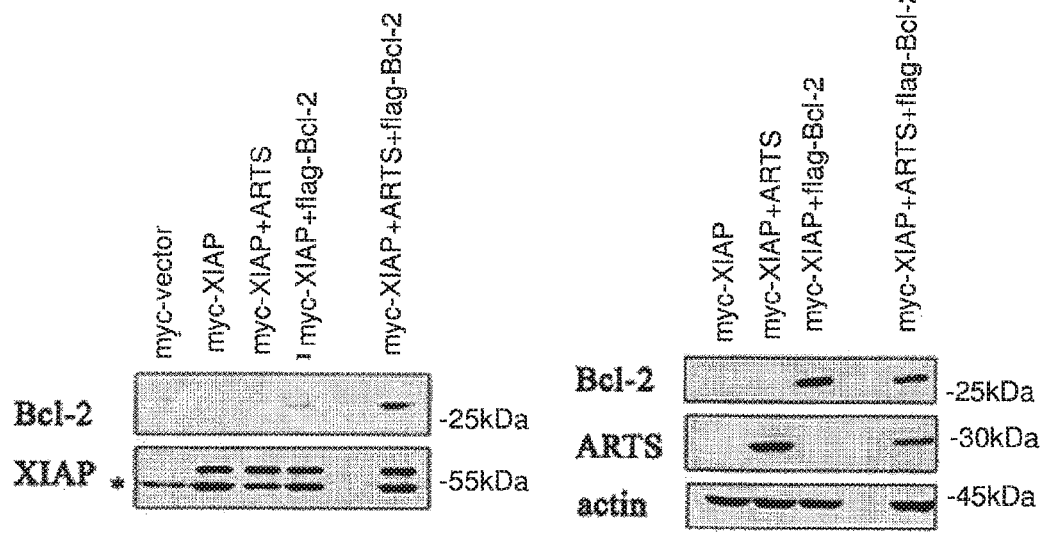
Figure 5A                    Figure 5B

HeLa cells

SEQUENCE LISTING

<160> NUMBER OF SEQ ID NOS: 40

<210> SEQ ID NO 1
<211> LENGTH: 6492
<212> TYPE: DNA
<213> ORGANISM: Homo sapiens

<400> SEQUENCE: 1

| | | | | | |
|---|---|---|---|---|---|
| tttctgtgaa | gcagaagtct | gggaatcgat | ctggaaatcc | tcctaattt | tactccctct | 60 |
| ccccgcgact | cctgattcat | tgggaagttt | caaatcagct | ataactggag | agtgctgaag | 120 |
| attgatggga | tcgttgcctt | atgcatttgt | tttggtttta | caaaaggaa | acttgacaga | 180 |
| ggatcatgct | gtacttaaaa | aatacaacat | cacagaggaa | gtagactgat | attaacaata | 240 |
| cttactaata | ataacgtgcc | tcatgaaata | aagatccgaa | aggaattgga | ataaaatt | 300 |
| cctgcatctc | atgccaaggg | ggaaacacca | gaatcaagtg | ttccgcgtga | ttgaagacac | 360 |
| ccctcgtcc | aagaatgcaa | agcacatcca | ataaatagc | tggattataa | ctcctcttct | 420 |
| ttctctgggg | gccgtggggt | gggagctggg | gcgagaggtg | ccgttggccc | ccgttgcttt | 480 |
| tcctctggga | aggatggcgc | acgctgggag | aacagggtac | gataaccggg | agatagtgat | 540 |
| gaagtacatc | cattataagc | tgtcgcagag | gggctacgag | tgggatgcgg | gagatgtggg | 600 |
| cgccgcgccc | ccgggggccg | ccccgcacc | gggcatcttc | tcctcccagc | ccgggcacac | 660 |
| gccccatcca | gccgcatccc | gggacccggt | cgccaggacc | tcgccgctgc | agaccccggc | 720 |
| tgccccggc | gccgccgcgg | ggcctgcgct | cagcccggtg | ccacctgtgg | tccacctgac | 780 |
| cctccgccag | gccggcgacg | acttctcccg | ccgctaccgc | cgcgacttcg | ccgagatgtc | 840 |
| cagccagctg | cacctgacgc | ccttcaccgc | gcggggacgc | tttgccacgg | tggtggagga | 900 |
| gctcttcagg | gacggggtga | actggggag | gattgtggcc | ttctttgagt | tcggtggggt | 960 |
| catgtgtgtg | gagagcgtca | accgggagat | gtcgccctg | gtggacaaca | tcgccctgtg | 1020 |
| gatgactgag | tacctgaacc | ggcacctgca | cacctggatc | caggataacg | gaggctggga | 1080 |
| tgcctttgtg | gaactgtacg | gccccagcat | gcggcctctg | tttgatttct | cctggctgtc | 1140 |
| tctgaagact | ctgctcagtt | tggccctggt | gggagcttgc | atcaccctgg | gtgcctatct | 1200 |
| gggccacaag | tgaagtcaac | atgcctgccc | caaacaaata | tgcaaaaggt | tcactaaagc | 1260 |
| agtagaaata | atatgcattg | tcagtgatgt | accatgaaac | aaagctgcag | gctgtttaag | 1320 |
| aaaaaataac | acacatataa | acatcacaca | cacagacaga | cacacacaca | cacaacaatt | 1380 |
| aacagtcttc | aggcaaaacg | tcgaatcagc | tatttactgc | caaagggaaa | tatcatttat | 1440 |
| tttttacatt | attaagaaaa | aaagatttat | ttatttaaga | cagtcccatc | aaaactcctg | 1500 |
| tctttggaaa | tccgaccact | aattgccaag | caccgcttcg | tgtggctcca | cctggatgtt | 1560 |
| ctgtgcctgt | aaacatagat | tcgctttcca | tgttgttggc | cggatcacca | tctgaagagc | 1620 |
| agacggatgg | aaaaaggacc | tgatcattgg | ggaagctggc | tttctggctg | ctggaggctg | 1680 |
| gggagaaggt | gttcattcac | ttgcatttct | ttgccctggg | ggctgtgata | ttaacagagg | 1740 |
| gagggttcct | gtgggggaa | gtccatgcct | ccctggcctg | aagaagagac | tctttgcata | 1800 |
| tgactcacat | gatgcatacc | tggtgggagg | aaaagagttg | gaacttcag | atggacctag | 1860 |
| tacccactga | gatttccacg | ccgaaggaca | gcgatgggaa | aaatgccctt | aaatcatagg | 1920 |
| aaagtatttt | tttaagctac | caattgtgcc | gagaaaagca | ttttagcaat | ttatacaata | 1980 |
| tcatccagta | ccttaagccc | tgattgtgta | tattcatata | ttttggatac | gcaccccca | 2040 |
| actcccaata | ctggctctgt | ctgagtaaga | aacagaatcc | tctggaactt | gaggaagtga | 2100 |

```
acatttcggt gacttccgca tcaggaaggc tagagttacc cagagcatca ggccgccaca    2160
agtgcctgct tttaggagac cgaagtccgc agaacctgcc tgtgtcccag cttggaggcc    2220
tggtcctgga actgagccgg ggccctcact ggcctcctcc agggatgatc aacagggcag    2280
tgtggtctcc gaatgtctgg aagctgatgg agctcagaat tccactgtca agaaagagca    2340
gtagaggggt gtggctgggc ctgtcaccct ggggccctcc aggtaggccc gttttcacgt    2400
ggagcatggg agccacgacc cttcttaaga catgtatcac tgtagaggga aggaacagag    2460
gccctgggcc cttcctatca gaaggacatg gtgaaggctg gaacgtgag gagaggcaat    2520 ggccacggcc cattttggct gtagcacatg gcacgttggc tgtgtggcct tggcccacct    2580
gtgagtttaa agcaaggctt taaatgactt tggagagggt cacaaatcct aaaagaagca    2640
ttgaagtgag gtgtcatgga ttaattgacc cctgtctatg gaattacatg taaaacatta    2700
tcttgtcact gtagtttggt tttatttgaa aacctgacaa aaaaaaagtt ccaggtgtgg    2760
aatatggggg ttatctgtac atcctggggc attaaaaaaa aaatcaatgg tggggaacta    2820
taaagaagta acaaaagaag tgacatcttc agcaaataaa ctaggaaatt ttttttttctt    2880 ccagtttaga atcagccttg aaacattgat ggaataactc tgtggcatta ttgcattata    2940
taccatttat ctgtattaac tttggaatgt actctgttca atgtttaatg ctgtggttga    3000
tatttcgaaa gctgctttaa aaaaatacat gcatctcagc gttttttgt ttttaattgt    3060 atttagttat ggcctataca ctatttgtga gcaaggtga tcgttttctg tttgagattt    3120
ttatctcttg attcttcaaa agcattctga gaaggtgaga taagccctga gtctcagcta    3180
cctaagaaaa acctggatgt cactggccac tgaggagctt tgtttcaacc aagtcatgtg    3240
catttccacg tcaacagaat tgtttattgt gacagttata tctgttgtcc ctttgacctt    3300
gtttcttgaa ggtttcctcg tccctgggca attccgcatt taattcatgg tattcaggat    3360
tacatgcatg tttggttaaa cccatgagat tcattcagtt aaaaatccag atggcaaatg    3420
accagcagat tcaaatctat ggtggtttga cctttagaga gttgctttac gtggcctgtt    3480
tcaacacaga cccacccaga gccctcctgc cctccttccg cggggctttt ctcatggctg    3540
tccttcaggg tcttcctgaa atgcagtggt gcttacgctc caccaagaaa gcaggaaacc    3600
tgtggtatga agccagacct ccccggcggg cctcagggaa cagaatgatc agacctttga    3660
atgattctaa ttttttaagca aaatattatt ttatgaaagg tttacattgt caaagtgatg    3720
aatatggaat atccaatcct gtgctgctat cctgccaaaa tcattttaat ggagtcagtt    3780
tgcagtatgc tccacgtggt aagatcctcc aagctgcttt agaagtaaca atgaagaacg    3840
tggacgtttt taatataaag cctgttttgt cttttgttgt tgttcaaacg ggattcacag    3900
agtatttgaa aaatgtatat atattaagag gtcacggggg ctaattgctg gctggctgcc    3960
ttttgctgtg gggttttgtt acctggtttt aataacagta aatgtgccca gcctcttggc    4020
cccagaactg tacagtattg tggctgcact tgctctaaga gtagttgatg ttgcattttc    4080
cttattgtta aaaacatgtt agaagcaatg aatgtatata aaagcctcaa ctagtcattt    4140
ttttctcctc ttctttttttt tcattatatc taattatttt gcagttgggc aacagagaac    4200
catccctatt ttgtattgaa gagggattca catctgcatc ttaactgctc tttatgaatg    4260
aaaaaacagt cctctgtatg tactcctctt tacactggcc agggtcagag ttaaatagag    4320
tatatgcact ttccaaattg gggacaaggg ctctaaaaaa agccccaaaa ggagaagaac    4380
atctgagaac ctcctcggcc ctcccagtcc ctcgctgcac aaatactccg caagagaggc    4440
```

```
cagaatgaca gctgacaggg tctatggcca tcgggtcgtc tccgaagatt tggcaggggc      4500
agaaaactct ggcaggctta agatttggaa taaagtcaca gaattaagga agcacctcaa      4560
tttagttcaa acaagacgcc aacattctct ccacagctca cttacctctc tgtgttcaga      4620
tgtggccttc catttatatg tgatctttgt tttattagta aatgcttatc atctaaagat      4680
gtagctctgg cccagtggga aaaattagga agtgattata aatcgagagg agttataata      4740
atcaagatta aatgtaaata atcagggcaa tcccaacaca tgtctagctt tcacctccag      4800
gatctattga gtgaacagaa ttgcaaatag tctctatttg taattgaact tatcctaaaa      4860
caaatagttt ataaatgtga acttaaactc taattaattc caactgtact tttaaggcag      4920
tggctgtttt tagactttct tatcacttat agttagtaat gtacacctac tctatcagag      4980
aaaaacagga aaggctcgaa atacaagcca ttctaaggaa attagggagt cagttgaaat      5040
tctattctga tcttattctg tggtgtcttt tgcagcccag acaaatgtgg ttacacactt      5100
tttaagaaat acaattctac attgtcaagc ttatgaaggt tccaatcaga tctttattgt      5160
tattcaattt ggatctttca gggattttt ttttaaatta ttatgggaca aaggacattt      5220
gttggagggg tgggagggag gaagaatttt taaatgtaaa acattcccaa gtttggatca      5280
gggagttgga agttttcaga ataaccagaa ctaagggtat gaaggacctg tattggggtc      5340
gatgtgatgc ctctgcgaag aaccttgtgt gacaaatgag aaacattttg aagtttgtgg      5400
tacgaccttt agattccaga gacatcagca tggctcaaag tgcagctccg tttggcagtg      5460
caatggtata aatttcaagc tggatatgtc taatgggtat ttaaacaata aatgtgcagt      5520
tttaactaac aggatattta atgacaacct tctggttggt agggacatct gtttctaaat      5580
gtttattatg tacaatacag aaaaaaattt tataaaatta agcaatgtga aactgaattg      5640
gagagtgata atacaagtcc tttagtctta cccagtgaat cattctgttc catgtctttg      5700
gacaaccatg accttggaca atcatgaaat atgcatctca ctggatgcaa agaaaatcag      5760
atggagcatg aatggtactg taccggttca tctggactgc cccagaaaaa taacttcaag      5820
caaacatcct atcaacaaca aggttgttct gcataccaag ctgagcacag aagatgggaa      5880
cactggtgga ggatggaaag gctcgctcaa tcaagaaaat tctgagacta ttaataaata      5940
agactgtagt gtagatactg agtaaatcca tgcacctaaa cctttggaa aatctgccgt      6000 gggccctcca gatagctcat ttcattaagt ttttccctcc aaggtagaat ttgcaagagt      6060
gacagtggat tgcatttctt ttggggaagc tttcttttgg tggttttgtt tattatacct      6120
tcttaagttt tcaaccaagg tttgcttttg ttttgagtta ctggggttat ttttgtttta      6180
aataaaaata agtgtacaat aagtgttttt gtattgaaag cttttgttat caagattttc      6240
atacttttac cttccatggc tcttttaag attgatactt ttaagaggtg gctgatattc      6300
tgcaacactg tacacataaa aaatacggta aggatacttt acatggttaa ggtaaagtaa      6360
gtctccagtt ggccaccatt agctataatg gcactttgtt tgtgttgttg gaaaagtca      6420 cattgccatt aaactttcct tgtctgtcta gttaatattg tgaagaaaaa taagtacag      6480 tgtgagatac tg                                                         6492

<210> SEQ ID NO 2
<211> LENGTH: 1207
<212> TYPE: DNA
<213> ORGANISM: Homo sapiens

<400> SEQUENCE: 2
tttctgtgaa gcagaagtct gggaatcgat ctggaaatcc tcctaatttt tactccctct        60
```

```
cccccgcgact cctgattcat tgggaagttt caaatcagct ataactggag agtgctgaag      120
attgatggga tcgttgcctt atgcatttgt tttggtttta caaaaaggaa acttgacaga      180
ggatcatgct gtacttaaaa aatacaacat cacagaggaa gtagactgat attaacaata      240
cttactaata ataacgtgcc tcatgaaata aagatccgaa aggaattgga ataaaaattt      300
cctgcatctc atgccaaggg ggaaacacca gaatcaagtg ttccgcgtga ttgaagacac      360
cccctcgtcc aagaatgcaa agcacatcca ataaaatagc tggattataa ctcctcttct      420
ttctctgggg gccgtggggt gggagctggg gcgagaggtg ccgttggccc ccgttgcttt      480
tcctctggga aggatggcgc acgctgggag aacagggtac gataaccggg agatagtgat      540
gaagtacatc cattataagc tgtcgcagag gggctacgag tgggatgcgg agatgtggg      600 cgccgcgccc ccgggggccg ccccccgcacc gggcatcttc cctcccagc ccgggcacac      660 gccccatcca gccgcatccc gggacccggt cgccaggacc tcgccgctgc agaccccggc      720
tgcccccggc gccgccgcgg ggcctgcgct cagcccggtg ccacctgtgg tccacctgac      780
cctccgccag gccggcgacg acttctcccg ccgctaccgc cgcgacttcg ccgagatgtc      840
cagccagctg cacctgacgc ccttcaccgc gcggggacgc tttgccacgg tggtggagga      900
gctcttcagg gacggggtga actggggagag gattgtggcc ttctttgagt tcggtggggt      960
catgtgtgtg gagagcgtca accgggagat gtcgccctg gtggacaaca tcgccctgtg     1020
gatgactgag tacctgaacc ggcacctgca cacctggatc caggataacg gaggctgggt     1080
aggtgcactt ggtgatgtga gtctgggctg aggccacagg tccgagatgc ggggggttgga     1140 gtgcgggtgg gctcctgggg caatgggagg ctgtggagcc ggcgaaataa aatcagagtt     1200
gttgcta                                                                1207
```

<210> SEQ ID NO 3
<211> LENGTH: 239
<212> TYPE: PRT
<213> ORGANISM: Homo sapiens

<400> SEQUENCE: 3

```
Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160
```

| Ser | Val | Asn | Arg | Glu | Met | Ser | Pro | Leu | Val | Asp | Asn | Ile | Ala | Leu | Trp |
|---|---|---|---|---|---|---|---|---|---|---|---|---|---|---|---|
| | | | 165 | | | | 170 | | | | | 175 | | | |

Met Thr Glu Tyr Leu Asn Arg His Leu His Thr Trp Ile Gln Asp Asn
           180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235

<210> SEQ ID NO 4
<211> LENGTH: 205
<212> TYPE: PRT
<213> ORGANISM: Homo sapiens

<400> SEQUENCE: 4

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Val Gly Ala Leu Gly Asp Val Ser Leu Gly
        195                 200                 205

<210> SEQ ID NO 5
<211> LENGTH: 926
<212> TYPE: DNA
<213> ORGANISM: Homo sapiens

<400> SEQUENCE: 5
gaatctcttt ctctcccttc agaatcttat cttggctttg gatcttagaa gagaatcact      60
aaccagagac gagactcagt gagtgagcag gtgttttgga caatggactg gttgagccca     120
tccctattat aaaaatgtct cagagcaacc gggagctggt ggttgacttt ctctcctaca     180
agctttccca gaaggatac agctggagtc agtttagtga tgtggaagag aacaggactg      240
aggccccaga agggactgaa tcggagatgg agacccccag tgccatcaat ggcaacccat     300

-continued

```
cctggcacct ggcagacagc cccgcggtga atggagccac tgcgcacagc agcagtttgg      360
atgcccggga ggtgatcccc atggcagcag taaagcaagc gctgagggag gcaggcgacg      420
agtttgaact gcggtaccgg cgggcattca gtgacctgac atcccagctc cacatcaccc      480
cagggacagc atatcagagc tttgaacagg tagtgaatga actcttccgg gatgggtaa       540 actggggtcg cattgtggcc ttttctcct cggcggggc actgtgcgtg aaagcgtag         600 acaaggagat gcaggtattg gtgagtcgga tcgcagcttg gatggccact tacctgaatg     660
accacctaga gccttggatc caggagaacg gcggctggga tactttttgtg gaactctatg   720 ggaacaatgc agcagccgag agccgaaagg gccaggaacg cttcaaccgc tggttcctga    780
cgggcatgac tgtggccggc gtggttctgc tgggctcact cttcagtcgg aaatgaccag    840
acactgacca tccactctac cctcccaccc ccttctctgc tccaccacat cctccgtcca     900
gccgccattg ccaccaggag aaccccg                                         926
```

<210> SEQ ID NO 6
<211> LENGTH: 233
<212> TYPE: PRT
<213> ORGANISM: Homo sapiens

<400> SEQUENCE: 6

```
Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
                20                  25                  30

Asn Arg Thr Glu Ala Pro Glu Gly Thr Glu Ser Glu Met Glu Thr Pro
            35                  40                  45

Ser Ala Ile Asn Gly Asn Pro Ser Trp His Leu Ala Asp Ser Pro Ala
        50                  55                  60

Val Asn Gly Ala Thr Ala His Ser Ser Ser Leu Asp Ala Arg Glu Val
    65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
    130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
            180                 185                 190

Glu Leu Tyr Gly Asn Asn Ala Ala Ala Glu Ser Arg Lys Gly Gln Glu
        195                 200                 205

Arg Phe Asn Arg Trp Phe Leu Thr Gly Met Thr Val Ala Gly Val Val
    210                 215                 220

Leu Leu Gly Ser Leu Phe Ser Arg Lys
225                 230
```

<210> SEQ ID NO 7
<211> LENGTH: 18

```
<212> TYPE: DNA
<213> ORGANISM: Artificial Sequence
<220> FEATURE:
<223> OTHER INFORMATION: BH3 mimetic compound

<400> SEQUENCE: 7
tctcccagcg tgcgccat                                                   18

<210> SEQ ID NO 8
<211> LENGTH: 1911
<212> TYPE: DNA
<213> ORGANISM: Homo sapiens

<400> SEQUENCE: 8
cggcggtgct gcgaggtcgg cgcgcacgtc cgccgcgggt cgctcgggcg ctgtccaggc       60
ggagccggcc ccgcccgggc tgcagccatg atcaagcgtt tcctggagga caccacggat      120
gatggagaac tgagcaagtt cgtgaaggat ttctcaggaa atgcgagctg ccacccacca      180
gaggctaaga cctgggcatc caggcccaa gtcccggagc caaggcccca ggccccggac       240
ctctatgatg atgacctgga gttcagaccc ccctcgcggc cccagtcctc tgacaaccag      300
cagtacttct gtgccccagc ccctctcagc ccatctgcca ggccccgcag cccatggggc      360
aagcttgatc cctatgattc ctctgaggat gacaaggagt atgtgggctt gcaacccctc      420
cccaaccaag tccaccgaaa gtccgtgaag aaaggctttg actttaccct catggtggca      480
ggagagtctg gcctgggcaa atccacactt gtcaatagcc tcttcctcac tgatctgtac      540
cgggaccgga aacttcttgg tgctgaagag aggatcatgc aaactgtgga gatcactaag      600
catgcagtgg acatagaaga aagggtgtg aggctgcggc tcaccattgt ggacacacca      660
ggttttgggg atgcagtcaa caacacagag tgctggaagc tgtggcaga atacattgat      720 cagcagtttg agcagtattt ccgagacgag agtggcctga accgaaagaa catccaagac      780
aacagggtgc actgctgcct gtacttcatc tcacccttcg ccatgggta tggtccaagc      840 ctgaggctcc tggcaccacc gggtgctgtc aagggaacag ccaagagca ccaggggcag      900 ggctgccact agcaggtggt cacaggttcc tgttccccag gctccggcca ttggatgttg      960
aattcatgaa ggccctgcat cagcgggtca acatcgtgcc tatcctggct aaggcagaca     1020
cactgacacc tcccgaagtg gaccacaaga acgcaaaat ccgggaggag attgagcatt      1080
ttggaatcaa gatctatcaa ttcccagact gtgactctga tgaggatgag gacttcaaat     1140
tgcaggacca agccctaaag gaaagcatcc catttgcagt aattggcagc aacactgtag     1200
tagaggccag agggcggcga gttcggggtc gactctaccc ctgggcatc gtggaagtgg      1260 aaaacccagg gcactgcgac tttgtgaagc tgaggacaat gctggtacgt acccacatgc     1320
aggacctgaa ggatgtgaca cgggagacac attatgagaa ctaccgggca cagtgcatcc     1380
agagcatgac ccgcctggtg gtgaaggaac ggaatcgcaa gtatgaccag aagccaggac     1440
aaagctggca gggggagatc ccaagcctag ccttgggtga gaccaagccc acttttgtt      1500 cttctatagg ccctgggctc aatctaagcg ggtgctgggg tcctcctcgc cttatcaacc     1560
cttttctccc tttagcaaac tgactcggga agtggtacc gacttcccca tccctgctgt      1620
cccaccaggg acagatccag aaactgagaa gcttatccga gagaaagatg aggagctgcg     1680
gcggatgcag gagatgctac acaaaataca aaaacagatg aaggagaact attaactggc     1740 tttcagcccct ggatatttaa atctcctcct cttcttcctg tccatgccgg ccctcccag     1800 caccagctct gctcaggccc cttcagctac tgccacttcg ccttacatcc ctgctgactg     1860
```
cccagagact cagaggaaat aaagtttaat aaatctgtag gtggctaaaa a    1911

<210> SEQ ID NO 9
<211> LENGTH: 274
<212> TYPE: PRT
<213> ORGANISM: Homo sapiens

<400> SEQUENCE: 9

Met Ile Lys Arg Phe Leu Glu Asp Thr Thr Asp Asp Gly Glu Leu Ser
1               5                   10                  15

Lys Phe Val Lys Asp Phe Ser Gly Asn Ala Ser Cys His Pro Pro Glu
            20                  25                  30

Ala Lys Thr Trp Ala Ser Arg Pro Gln Val Pro Glu Pro Arg Pro Gln
        35                  40                  45

Ala Pro Asp Leu Tyr Asp Asp Leu Glu Phe Arg Pro Pro Ser Arg
    50                  55                  60

Pro Gln Ser Ser Asp Asn Gln Gln Tyr Phe Cys Ala Pro Ala Pro Leu
65                  70                  75                  80

Ser Pro Ser Ala Arg Pro Arg Ser Pro Trp Gly Lys Leu Asp Pro Tyr
                85                  90                  95

Asp Ser Ser Glu Asp Asp Lys Glu Tyr Val Gly Phe Ala Thr Leu Pro
            100                 105                 110

Asn Gln Val His Arg Lys Ser Val Lys Lys Gly Phe Asp Phe Thr Leu
        115                 120                 125

Met Val Ala Gly Glu Ser Gly Leu Gly Lys Ser Thr Leu Val Asn Ser
130                 135                 140

Leu Phe Leu Thr Asp Leu Tyr Arg Asp Arg Lys Leu Leu Gly Ala Glu
145                 150                 155                 160

Glu Arg Ile Met Gln Thr Val Glu Ile Thr Lys His Ala Val Asp Ile
                165                 170                 175

Glu Glu Lys Gly Val Arg Leu Arg Leu Thr Ile Val Asp Thr Pro Gly
            180                 185                 190

Phe Gly Asp Ala Val Asn Asn Thr Glu Cys Trp Lys Pro Val Ala Glu
        195                 200                 205

Tyr Ile Asp Gln Gln Phe Glu Gln Tyr Phe Arg Asp Glu Ser Gly Leu
    210                 215                 220

Asn Arg Lys Asn Ile Gln Asp Asn Arg Val His Cys Cys Leu Tyr Phe
225                 230                 235                 240

Ile Ser Pro Phe Gly His Gly Tyr Gly Pro Ser Leu Arg Leu Leu Ala
                245                 250                 255

Pro Pro Gly Ala Val Lys Gly Thr Gly Gln Glu His Gly Gln Gly
            260                 265                 270

Cys His

<210> SEQ ID NO 10
<211> LENGTH: 128
<212> TYPE: PRT
<213> ORGANISM: Homo sapiens

<400> SEQUENCE: 10

Met Ile Lys Arg Phe Leu Glu Asp Thr Thr Asp Asp Gly Glu Leu Ser
1               5                   10                  15

Lys Phe Val Lys Asp Phe Ser Gly Asn Ala Ser Cys His Pro Pro Glu
            20                  25                  30

Ala Lys Thr Trp Ala Ser Arg Pro Gln Val Pro Glu Pro Arg Pro Gln
        35                  40                  45

Ala Pro Asp Leu Tyr Asp Asp Leu Glu Phe Arg Pro Pro Ser Arg
 50                  55                  60

Pro Gln Ser Ser Asp Asn Gln Gln Tyr Phe Cys Ala Pro Ala Pro Leu
 65                  70                  75                  80

Ser Pro Ser Ala Arg Pro Arg Ser Pro Trp Gly Lys Leu Asp Pro Tyr
                 85                  90                  95

Asp Ser Ser Glu Asp Asp Lys Glu Tyr Val Gly Phe Ala Thr Leu Pro
                100                 105                 110

Asn Gln Val His Arg Lys Ser Val Lys Lys Gly Phe Asp Phe Thr Leu
                115                 120                 125

<210> SEQ ID NO 11
<211> LENGTH: 148
<212> TYPE: PRT
<213> ORGANISM: Homo sapiens

<400> SEQUENCE: 11

Met Ile Lys Arg Phe Leu Glu Asp Thr Thr Asp Asp Gly Glu Leu Ser
 1               5                  10                  15

Lys Phe Val Lys Asp Phe Ser Gly Asn Ala Ser Cys His Pro Pro Glu
                20                  25                  30

Ala Lys Thr Trp Ala Ser Arg Pro Gln Val Pro Glu Pro Arg Pro Gln
                35                  40                  45

Ala Pro Asp Leu Tyr Asp Asp Leu Glu Phe Arg Pro Pro Ser Arg
 50                  55                  60

Pro Gln Ser Ser Asp Asn Gln Gln Tyr Phe Cys Ala Pro Ala Pro Leu
 65                  70                  75                  80

Ser Pro Ser Ala Arg Pro Arg Ser Pro Trp Gly Lys Leu Asp Pro Tyr
                 85                  90                  95

Asp Ser Ser Glu Asp Asp Lys Glu Tyr Val Gly Phe Ala Thr Leu Pro
                100                 105                 110

Asn Gln Val His Arg Lys Ser Val Lys Lys Gly Phe Asp Phe Thr Leu
                115                 120                 125

Met Val Ala Gly Glu Ser Gly Leu Gly Lys Ser Thr Leu Val Asn Ser
                130                 135                 140

Leu Phe Leu Thr
145

<210> SEQ ID NO 12
<211> LENGTH: 43
<212> TYPE: PRT
<213> ORGANISM: Homo sapiens

<400> SEQUENCE: 12

Val Gly Phe Ala Thr Leu Pro Asn Gln Val His Arg Lys Ser Val Lys
 1               5                  10                  15

Lys Gly Phe Asp Phe Thr Leu Met Val Ala Gly Glu Ser Gly Leu Gly
                20                  25                  30

Lys Ser Thr Leu Val Asn Ser Leu Phe Leu Thr
                35                  40

<210> SEQ ID NO 13
<211> LENGTH: 28
<212> TYPE: PRT
<213> ORGANISM: Homo sapiens

<400> SEQUENCE: 13

Val Gly Phe Ala Thr Leu Pro Asn Gln Val His Arg Lys Ser Val Lys
1               5                   10                  15

Lys Gly Phe Asp Phe Thr Leu Met Val Ala Gly Glu
            20                  25

<210> SEQ ID NO 14
<211> LENGTH: 23
<212> TYPE: PRT
<213> ORGANISM: Homo sapiens

<400> SEQUENCE: 14

Val Gly Phe Ala Thr Leu Pro Asn Gln Val His Arg Lys Ser Val Lys
1               5                   10                  15

Lys Gly Phe Asp Phe Thr Leu
            20

<210> SEQ ID NO 15
<211> LENGTH: 37
<212> TYPE: PRT
<213> ORGANISM: Homo sapiens

<400> SEQUENCE: 15

Pro Asn Gln Val His Arg Lys Ser Val Lys Lys Gly Phe Asp Phe Thr
1               5                   10                  15

Leu Met Val Ala Gly Glu Ser Gly Leu Gly Lys Ser Thr Leu Val Asn
            20                  25                  30

Ser Leu Phe Leu Thr
        35

<210> SEQ ID NO 16
<211> LENGTH: 22
<212> TYPE: PRT
<213> ORGANISM: Homo sapiens

<400> SEQUENCE: 16

Pro Asn Gln Val His Arg Lys Ser Val Lys Lys Gly Phe Asp Phe Thr
1               5                   10                  15

Leu Met Val Ala Gly Glu
            20

<210> SEQ ID NO 17
<211> LENGTH: 17
<212> TYPE: PRT
<213> ORGANISM: Homo sapiens

<400> SEQUENCE: 17

Pro Asn Gln Val His Arg Lys Ser Val Lys Lys Gly Phe Asp Phe Thr
1               5                   10                  15

Leu

<210> SEQ ID NO 18
<211> LENGTH: 23
<212> TYPE: PRT
<213> ORGANISM: Homo sapiens

<400> SEQUENCE: 18

Ala Ala Gln Arg Tyr Gly Arg Glu Leu Arg Arg Met Ser Asp Glu Phe
1               5                   10                  15

Val Asp Ser Phe Lys Lys Gly
            20

```
<210> SEQ ID NO 19
<211> LENGTH: 23
<212> TYPE: PRT
<213> ORGANISM: Homo sapiens

<400> SEQUENCE: 19

Thr Met Gly Gln Val Gly Arg Gln Leu Ala Ile Ile Gly Asp Asp Ile
1               5                   10                  15

Asn Arg Arg Tyr Asp Ser Glu
            20

<210> SEQ ID NO 20
<211> LENGTH: 23
<212> TYPE: PRT
<213> ORGANISM: Homo sapiens

<400> SEQUENCE: 20

Ser Thr Lys Lys Leu Ser Glu Cys Leu Lys Arg Ile Gly Asp Glu Leu
1               5                   10                  15

Asp Ser Asn Met Glu Leu Gln
            20

<210> SEQ ID NO 21
<211> LENGTH: 23
<212> TYPE: PRT
<213> ORGANISM: Homo sapiens

<400> SEQUENCE: 21

Ile Ile Arg Asn Ile Ala Arg His Leu Ala Gln Val Gly Asp Ser Met
1               5                   10                  15

Asp Arg Ser Ile Pro Pro Gly
            20

<210> SEQ ID NO 22
<211> LENGTH: 23
<212> TYPE: PRT
<213> ORGANISM: Homo sapiens

<400> SEQUENCE: 22

Gly Ser Asp Ala Leu Ala Leu Arg Leu Ala Cys Ile Gly Asp Glu Met
1               5                   10                  15

Asp Val Ser Leu Arg Ala Pro
            20

<210> SEQ ID NO 23
<211> LENGTH: 23
<212> TYPE: PRT
<213> ORGANISM: Homo sapiens

<400> SEQUENCE: 23

Pro Glu Ile Trp Ile Ala Gln Glu Leu Arg Arg Ile Gly Asp Glu Phe
1               5                   10                  15

Asn Ala Tyr Tyr Ala Arg Arg
            20

<210> SEQ ID NO 24
<211> LENGTH: 23
<212> TYPE: PRT
<213> ORGANISM: Homo sapiens

<400> SEQUENCE: 24

Arg Leu Ala Glu Val Cys Thr Val Leu Leu Glu Leu Gly Asp Glu Leu
1               5                   10                  15
```

```
Glu Gln Ile Arg Pro Ser Val
            20

<210> SEQ ID NO 25
<211> LENGTH: 23
<212> TYPE: PRT
<213> ORGANISM: Homo sapiens

<400> SEQUENCE: 25

Ala Ala Gln Leu Thr Ala Ala Arg Leu Lys Ala Leu Gly Asp Glu Leu
1               5                   10                  15

His Gln Arg Thr Met Trp Arg
            20

<210> SEQ ID NO 26
<211> LENGTH: 23
<212> TYPE: PRT
<213> ORGANISM: Homo sapiens

<400> SEQUENCE: 26

Val Pro Pro Val Val His Leu Thr Leu Arg Gln Ala Gly Asp Asp Phe
1               5                   10                  15

Ser Arg Arg Tyr Arg Arg Asp
            20

<210> SEQ ID NO 27
<211> LENGTH: 23
<212> TYPE: PRT
<213> ORGANISM: Homo sapiens

<400> SEQUENCE: 27

Pro Met Ala Ala Val Lys Gln Ala Leu Arg Glu Ala Gly Asp Glu Phe
1               5                   10                  15

Glu Leu Arg Tyr Arg Arg Ala
            20

<210> SEQ ID NO 28
<211> LENGTH: 23
<212> TYPE: PRT
<213> ORGANISM: Homo sapiens

<400> SEQUENCE: 28

Ala Ala Asp Pro Leu His Gln Ala Met Arg Ala Ala Gly Asp Glu Phe
1               5                   10                  15

Glu Thr Arg Phe Arg Arg Thr
            20

<210> SEQ ID NO 29
<211> LENGTH: 23
<212> TYPE: PRT
<213> ORGANISM: Homo sapiens

<400> SEQUENCE: 29

Thr Ser Arg Lys Ala Leu Glu Thr Leu Arg Arg Val Gly Asp Gly Val
1               5                   10                  15

Gln Arg Asn His Glu Thr Val
            20

<210> SEQ ID NO 30
<211> LENGTH: 68
<212> TYPE: PRT
<213> ORGANISM: Homo sapiens
```

```
<400> SEQUENCE: 30

Ala Glu Tyr Ile Asp Gln Gln Phe Glu Gln Tyr Phe Arg Asp Glu Ser
1               5                   10                  15

Gly Leu Asn Arg Lys Asn Ile Gln Asp Asn Arg Val His Cys Cys Leu
            20                  25                  30

Tyr Phe Ile Ser Pro Phe Gly His Gly Tyr Gly Pro Ser Leu Arg Leu
        35                  40                  45

Leu Ala Pro Pro Gly Ala Val Lys Gly Thr Gly Gln Glu His Gln Gly
    50                  55                  60

Gln Gly Cys His
65

<210> SEQ ID NO 31
<211> LENGTH: 27
<212> TYPE: PRT
<213> ORGANISM: Homo sapiens

<400> SEQUENCE: 31

Tyr Gly Pro Ser Leu Arg Leu Leu Ala Pro Pro Gly Ala Val Lys Gly
1               5                   10                  15

Thr Gly Gln Glu His Gln Gly Gln Gly Cys His
            20                  25

<210> SEQ ID NO 32
<211> LENGTH: 9
<212> TYPE: PRT
<213> ORGANISM: Homo sapiens

<400> SEQUENCE: 32

Gln Glu His Gln Gly Gln Gly Cys His
1               5

<210> SEQ ID NO 33
<211> LENGTH: 9
<212> TYPE: PRT
<213> ORGANISM: Homo sapiens

<400> SEQUENCE: 33

Tyr Gly Pro Ser Leu Arg Leu Leu Ala
1               5

<210> SEQ ID NO 34
<211> LENGTH: 9
<212> TYPE: PRT
<213> ORGANISM: Homo sapiens

<400> SEQUENCE: 34

Pro Pro Gly Ala Val Lys Gly Thr Gly
1               5

<210> SEQ ID NO 35
<211> LENGTH: 35
<212> TYPE: PRT
<213> ORGANISM: Homo sapiens

<400> SEQUENCE: 35

Val Gly Phe Ala Thr Leu Pro Asn Gln Val His Arg Lys Ser Val Lys
1               5                   10                  15

Lys Gly Phe Asp Phe Thr Leu Met Val Ala Gly Glu Ser Gly Leu Gly
            20                  25                  30
```

Lys Ser Thr
        35

<210> SEQ ID NO 36
<211> LENGTH: 15
<212> TYPE: PRT
<213> ORGANISM: Homo sapiens

<400> SEQUENCE: 36

Pro Asn Gln Val His Arg Lys Ser Val Lys Lys Gly Phe Asp Phe
1               5                   10                  15

<210> SEQ ID NO 37
<211> LENGTH: 8
<212> TYPE: PRT
<213> ORGANISM: Homo sapiens

<400> SEQUENCE: 37

Leu Arg Gln Ala Gly Asp Asp Phe
1               5

<210> SEQ ID NO 38
<211> LENGTH: 41
<212> TYPE: PRT
<213> ORGANISM: Homo sapiens

<400> SEQUENCE: 38

Pro Ala Leu Ser Pro Val Pro Val Val His Leu Thr Leu Arg Gln
1               5                   10                  15

Ala Gly Asp Asp Phe Ser Arg Arg Tyr Arg Arg Asp Phe Ala Glu Met
                20                  25                  30

Ser Ser Gln Leu His Leu Thr Pro Phe
        35                  40

<210> SEQ ID NO 39
<211> LENGTH: 28
<212> TYPE: PRT
<213> ORGANISM: Homo sapiens

<400> SEQUENCE: 39

Pro Ala Leu Ser Pro Val Pro Val Val His Leu Thr Leu Arg Gln
1               5                   10                  15

Ala Gly Asp Asp Phe Ser Arg Arg Tyr Arg Arg Asp
                20                  25

<210> SEQ ID NO 40
<211> LENGTH: 50
<212> TYPE: PRT
<213> ORGANISM: Homo sapiens

<400> SEQUENCE: 40

Asp Asp Lys Glu Tyr Val Gly Phe Ala Thr Leu Pro Asn Gln Val His
1               5                   10                  15

Arg Lys Ser Val Lys Lys Gly Phe Asp Phe Thr Leu Met Val Ala Gly
                20                  25                  30

Glu Ser Gly Leu Gly Lys Ser Thr Leu Val Asn Ser Leu Phe Leu Thr
        35                  40                  45

Asp Leu
    50

METHOD OF TREATING BCL-2 OVER-EXPRESSING DISORDERS USING ARTS CONTAINING A BH3-LIKE DOMAIN

SEQUENCE LISTING

This application contains a Sequence Listing submitted electronically as an ASCII text file and is hereby incorporated by reference in its entirety. Said ASCII text file, created Dec. 8, 2016, is named 2016-12-08SequenceListing-LARISCH2A.txt and is 34,083 bytes in size.

PRIOR ART

References considered to be relevant as background to the presently disclosed subject matter are listed below:
Fuchs, Y., and H. Steller. *Cell.* 147:1-17 (2011).
Gottfried, Y., A. et al., *EMBO J.* 23:1627-35 (2004).
Larisch, S., et al., *Nat Cell Biol.* 2:915-21 (2000).
Edison, N., D. et al. *Cell Death Differ.* 19:356-68 (2012b).
Bornstein, B., Y. et al., *Apoptosis* 16:869-881 (2011).
Reingewertz, T. H., et al., *PLoS One.* 6:e24655 (2011).
Adams, J. M., and S. Cory. *Trends Biochem Sci.* 26:61-6 (2001).
Youle, R. J., and A. Strasser. *Nat Rev Mol Cell Biol.* 9:47-59 (2008).
Happo, L., A. et al., *J Cell Sci.* 125:1081-7 (2012).
Robertson, L. E., et al., *Leukemia.* 10:456-9 (1996).
Oltersdorf, T. S. W. et al., *Nature.* 435:677-81 (2005).
Schile, A. J., M. *Genes Dev.* 22:2256-66 (2008).
Lotan, R., A. et al., *J Biol Chem.* 280:25802-10 (2005).
Kerppola, T. K. *Nat Protoc.* 1:1278-86 (2006).
Bader, M., and H. Steller. *Curr Opin Cell Biol.* 21:878-84 (2009).
Kaufmann, T., S. et al. *J Cell Biol.* 160:53-64 (2003).
Garcia-Fernandez, M., H. et al., *Genes Dev.* 24:2282-93 (2010).
Kissel, H., M. M. *Dev Cell.* 8:353-64 (2005).
Edison, N., T. H. et al., *Clin Cancer Res* (2012a).
Garrison, J. B., et al., *Mol Cell.* 41:107-16 (2010).
Bornstein, B. N., et al., *Int J Biochem Cell Biol.* 44:489-95 (2012).
Gandhi L, et al., *Journal of Clinical Oncology.* 29 (7): 909-16 (2011).

Acknowledgement of the above references herein is not to be inferred as meaning that these are in any way relevant to the patentability of the presently disclosed subject matter.

BACKGROUND OF THE INVENTION

Apoptosis is a process of programmed cell death that plays a major role in tissue development, tissue homeostasis, and as a defense mechanism against unwanted and potentially dangerous cells.

Apoptosis is controlled by a diverse range of cell signals which can originate either from extrinsic inducers thus activating the extrinsic, apoptotic signaling pathway or from intrinsic inducers, which activate the intrinsic, mitochondrial signaling pathway.

The control of apoptosis is achieved through the activity of pro- and anti-apoptotic proteins. For example, caspases, are a family of cysteine proteases that play a central executioners of apoptosis and the action of activators and inhibitors of caspases affect apoptosis. Inhibition of the caspases activity was reported to occur through the action of the inhibitor of apoptosis (IAP) proteins. Apoptosis has been reported to have a critical role in a variety of diseases. It has been shown that deregulation of the apoptosis pathway can result in various pathologic conditions, including cancer (Fuchs and Steller, 2011). Involvement of an abnormal ratio of pro- and anti-apoptotic proteins have been also associated with neurodegenerative diseases such as schizophrenia as well as in immune-related disorders To potentiate apoptosis the function of IAPB needs to be overcome. This is achieved by IAP-antagonists such as Smac/Diablo, Omi/HtrA2 and ARTS (Gottfried et al., 2004; Larisch et al., 2000).

ARTS is localized at mitochondrial outer membrane (MOM) (Edison et al., 2012b). Upon induction of apoptosis, ARTS translocates from the mitochondria to the cytosol, directly binds and antagonizes XIAP, causing activation of caspases and cell death (Bornstein et al., 2011; Edison et al., 2012b; Reingewertz et al., 2011). XIAP, the best studied IAP, can directly bind and inhibit caspases 3, 7 and 9 via its three Baculoviral IAP Repeats (BIR) domains.

The intrinsic pathway of apoptosis is regulated by Bcl-2 family members (Adams and Cory, 2001). This family is composed of pro- and anti-apoptotic proteins that share up to four conserved Bcl-2 homology (BH) domains (Youle and Strasser, 2008). The pro-apoptotic members can be separated into the "multidomain" proteins and to "BH3 only" proteins. Bax and Bak "multidomain" proteins which share three BH regions and structurally similar to the antiapoptotic proteins. The "BH3-only" proteins, which include Bnip3, Nix/Bnip3L, Bid, Noxa, Puma, and Bad, share only the BH3 domain and are structurally diverse (Happo et al., 2012.

The BH3-only proteins are thought to function as death signal sensors and play a major role in transducing signals from the cytosol to the mitochondria). Anti-apoptotic members such as Bcl-2, Bcl-XL and Mcl-1 contain all four subtypes of BH domains and have been reported to protect cells from many different apoptotic stimuli and are thus important for cell survival (Youle and Strasser, 2008). Importantly, many hematologic malignancies (lymphoma, leukemia) as well as certain solid cancers including, prostate, colorectal, lung, gastric, renal and neuroblastoma, are characterized by high levels of Bcl-2 Robertson et al., 1996).

Therefore, Bcl-2 antagonists may be useful as anti-cancer drugs. For example, a BH3 mimetics, ABT-737 (Oltersdorf et al., 2005) and its orally active derivative ABT-263 (Gandhi L, et al., 2011), can bind with high affinity to Bcl-2, Bcl-XL and Bcl-W and kill cells through a Bax- and Bak-dependent mechanism (Oltersdorf et al., 2005).

Thus, there is need for compounds that target and inhibit both classes of pro-apoptotic proteins, the XIAP and Bcl-2. These compounds would be better and more effective inducers of apoptosis in pathologies over-expressing XIAP or Bcl-2, or both.

GENERAL DESCRIPTION OF THE INVENTION

According to a first aspect, the invention relates to an antagonist of a Bcl-2 prosurvival protein. The antagonist of the invention comprises ARTS and any fragment, peptide, analogues and derivatives thereof. It should be noted that the fragment or peptide of ARTS comprises a Bcl-2 homology domain 3 (BH3)-like domain.

Another aspect of the invention relates to a composition comprising the antagonist of the invention. The invention further provides combined compositions comprising the antagonists of the invention and a BH3-mimetic compound.

Still further aspect relates to a method for treating, inhibiting, preventing, ameliorating or delaying the onset of a Bcl-2 over-expressing pathological disorder. The method of the invention comprises the step of administering to a subject in need thereof a therapeutically effective amount of at least one of the antagonists according to the invention. In certain embodiments the method of the invention further comprises a diagnostic step for determining the appropriate subjects that should be treated.

The invention further provides a kit comprising the antagonists of the invention and a BH3-mimetic compound.

In yet another aspect, the invention provides the use of the antagonists of the invention for treating Bcl-2 over-expressing disorders in subjects being treated with BH3-mimetic compounds.

A further aspect of the invention provides a prognostic method for determining the efficacy and assessing responsiveness of a mammalian subject suffering from a Bcl-2 over-expressing disorder, to a BH3 mimetics treatment using ARTS as a marker.

Another aspect of the invention provides a method using ARTS as a marker, for determining a BH3 mimetics treatment regimen for a subject suffering from a Bcl-2 over expressing pathological disorder.

These and other aspect of the invention will become apparent by the hand of the following drawings.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 1A-1L. Apoptotic induction leads to down-regulation of Bcl-2 levels

FIGS. 1A-1K. show western blots analysis showing the effect of apoptosis induced by staurosporin (STS) or etoposide (Etopo) on Bcl-2 levels in different cell lines. FIGS. 1A to 1D STS treatment in BT-549 cells (FIG. 1A), in COS-7 (FIG. 1B), HeLa (FIG. 1C) and immortalized MEFs (FIG. 1D). FIGS. 1E to 1I show Etopo treatment in COS-7 (FIGS. 1E, 1F), HeLa (FIG. 1G), BT-549 (FIG. 1H) and primary MEFs (FIG. 1I). FIGS. 1J to 1L show densitometry analyses of the results shown in FIGS. 1G to 1I, respectively were performed using Total Lab software.

FIG. 2A. is a western blot analysis of COS-7 cells transiently transfected with Bcl-2 or co-transfected with Bcl-2 and ARTS constructs and incubated with the 20 μM of proteasome inhibitor MG132 for 6 h. FIG. 2B. shows the respective densitometry analyses of the data. FIG. 2C. shows data from Immortalized WT MEFs transiently transfected with Bcl-2, XIAP and ubiquitin and treated with 20 μM MG132 for 6 h. Apoptosis was induced using 1.5 μM of STS for indicated time periods.

FIGS. 3A-3M. ARTS is required for down-regulation of Bcl-2 levels

FIGS. 3A-3C are fluorescence images showing the localization of Bcl-2 and ARTS and corresponding analysis graphs from HeLa cells. Mitochondria was detected using MitoTracker, Bcl-2—FITC, Nuclear—DAPI. FIG. 3D. Western blot analysis showing that Bcl-2 is released to the cytosol prior MOMP upon apoptotic induction in BT-549 cells. Apoptosis was induced in BT-549 cells using 0.6 μM STS for different time periods. Cell fractionation was performed by syringe-based method as described in methods section.

FIGS. 3E-3F. Western blot analysis showing that ARTS is required for proper release of Bcl-2. Apoptosis was induced in HeLa cells using 1.75 μM STS for different time periods. Cell fractionation was performed using digitonin technique as described in methods section. ARTS KD HeLa cells revealed a delayed release of Bcl-2 from mitochondria (FIG. 3F).

FIG. 3G-3H. are Western blot analysis showing that transfection with pro-apoptotic protein ARTS leads to down-regulation of exogenous Bcl-2 in COS-7 cells. COS-7 cell were transiently transfected with ARTS, Bcl-2 or empty vector or co-transfected with both constructs. Densitometry analyses of Bcl-2 levels versus actin were performed using Total Lab software.

FIG. 3I-3J Western blot analysis and corresponding densitometry showing that COS-7 cells with exogenous ARTS revealed lower levels of Bcl-2. COS-7 cells were transiently transfected with Bcl-2 or co-transfected with Bcl-2 and ARTS constructs. Apoptotic induction was performed using different concentrations of Etoposide for 16 h. Western blot analysis of the whole cell lysate was conducted using the indicated antibodies (FIG. 3I). Densitometry analyses of Bcl-2 levels versus actin were performed using Total Lab software (FIG. 3J).

FIG. 3K. is a Western bolt analysis showing that ARTS is important for regulation of Bcl-2 levels. A stable ARTS knockdown (ARTS KD) cell line in which ARTS expression was knocked down by short hairpin RNAs (shRNAs) was established in HeLa cells. Western blot analyses of whole cell lysates from ARTS KD HeLa cells demonstrate increased levels of Bcl-2 when compared with WT HeLa cells.

FIG. 3L. Western blot analysis of MEFs from WT and Sept4/ARTS KO mice showing that Sept4/ARTS knockout MEFs exhibit a strong increase in Bcl-2 levels.

FIG. 3M. Western blot analysis showing that ARTS is required for down-regulation of Bcl-2 levels. Apoptosis was induced in ARTS KD HeLa and in control WT HeLa cells using 1.75 μM STS for indicated periods of time. Western blot analyses demonstrate that during apoptosis in WT HeLa cells Bcl-2 levels were reduced, while in cells with knocked-down ARTS Bcl-2 levels remained unchanged.

FIGS. 4A-4E. Bcl-2, ARTS and XIAP act as a complex

FIG. 4A. is a blot showing that ARTS binds to Bcl-2 in living COS-7 cells. Binding of ARTS to Bcl-2 was tested in COS-7 cells which were co-transfected with Bcl-2 and ARTS expression vectors. Pull-down assays performed using agarose anti-myc beads followed by Western blot analysis using mouse anti-ARTS and anti-Bcl-2 antibodies.

FIG. 4B. Western blot analyses showing that in COS-7, HeLa and BT-549 cells endogenous ARTS, Bcl-2 and XIAP are found in the complex. ARTS was immunoprecipitated from HeLa, BT-549 and transiently transfected with 6-Myc-ARTS construct COS-7 cells. FIG. 4C. is an IP followed by Western blot showing that Endogenous ARTS and Bcl-2 coimmunoprecipitated with XIAP in living cells and under apoptotic conditions. Apoptotic induction in HeLa cells was performed using 1.75 μM STS for 2 h. The cells were lysed using Ripa buffer (without SDS) and equal protein concentrations were subjected to immunoprecipitation (IP) using anti-XIAP antibody. The precipitate was analyzed by Western blotting.

FIG. 4D. is an IP followed by Western blot showing that endogenous XIAP and Bcl-2 coimmunoprecipitated with ARTS in living cells and under apoptotic conditions. Apoptotic induction in HeLa cells was performed using 1.75 μM STS for 2 h. The cells were lysed and equal protein concentrations were subjected to immunoprecipitation using anti-ARTS antibody. The precipitate was analyzed by Western blotting.

FIG. 4E. is an IP followed by Western blot showing that XIAP and Bcl-2 coimmunoprecipitated with ARTS in living cells and under apoptotic conditions. Mitochondrial fraction was immunoprecipitated using anti-Bcl-2 antibody. The precipitate was analyzed by Western blotting.

FIGS. 5A-5B. ARTS is required for the binding of XIAP to Bcl-2

FIGS. 5A and 5B. are blots from COS-7 cells transiently co-transfected with combinations of ARTS, flag-Bcl-2, and myc-XIAP constructs. Pull-down of XIAP was performed using anti-myc beads, and the precipitate was subjected to Western blot analyses.

FIG. 6A-6B. Western blot analysis and corresponding densitometry showing that loss of E3-ligase ability of XIAP resulted in accumulation of Bcl-2. HeLa cells were transiently transfected with Bcl-2 or co-transfected with Bcl-2 and XIAP or Bcl-2 and XIAPdRING, a construct with impaired E3-ligase ability. Western blot and densitometry analyses demonstrate an accumulation of Bcl-2 protein levels during co-transfection with XIAPdRING suggesting involvement of XIAP in Bcl-2 down-regulation. FIG. 6C-6D. Western blot analysis and corresponding densitometry showing that catalytic activity of XIAP is necessary to reduce Bcl-2 levels in MEFs. MEFs were produced from WT and XIAPdRING 14-day old mouse embryos. Whole cell lysates were subjected to Western blot analyses. Densitometry analyses of three independent experiments were performed using Total Lab software. FIG. 6E. In vivo ubiquitination assay performed in WT and XIAPdRING MEFs following co-transfection with ARTS, Bcl-2 and ubiquitin. Apoptotic induction was performed using 1.75 µM STS for 0, 0.5 and 4 h. Cells were treated with 20 µM of proteasome inhibitor MG132 for 6 h. Immunoprecipitation assay was carried out with anti-Bcl-2 antibody, followed by immune-blotting with anti-ubiquitin antibody. FIG. 6F. In vivo ubiquitination assay was performed with WT and XIAP knock-out (KO) MEFs. MEFs were co-transfected with ARTS, Bcl-2 and HA-ubiquitin. Cells were treated with 15 µM of the proteasome inhibitor MG-132 for 6 h and 1.5 µM STS for 30 and 180 minutes. IP assay was carried out with anti-Bcl-2 antibody. Western blot analysis was performed using anti-HA, anti-Bcl-2 and anti-XIAP. Strong ubiquitination of Bcl-2 is seen 180 min following STS induction in MEFs but not in XIAP KO MEFs.

FIG. 6G. is a gel micrograph showing that XIAP is responsible for the drop in Bcl-2 level.

FIG. 7A-7B. shows that ARTS as well as XIAP are necessary for Bcl-2 down-regulation. HeLa or ARTS KD HeLa cells were co-transfected with Bcl-2 and XIAP or with Bcl-2 and XIAPdRING constructs. Bcl-2 levels were normalized to actin. Densitometry analyses of three independent experiments were performed using Total Lab software (FIG. 7B). FIG. 7C. shows ARTS is required for the ubiquitination of Bcl-2. HeLa or ARTS KD HeLa cells were transiently transfected with Bcl-2, XIAP and ubiquitin and treated with 20 µM MG132 for 6 h. Apoptosis was induced using 1.5 µM of STS for 0.5 h. The cells were harvested and subjected to immunoprecipitation (IP) using anti-Bcl-2 antibodies, followed by immune-blotting (IB) with anti-Bcl-2 antibodies.

FIGS. 8B-8D. show graphical presentation of the levels of Bcl-2 (FIG. 8B), c-PARP (FIG. 8C), c-Caspase 3 (FIG. 8D) and XIAP (FIG. 8E).

HeLa wt cells were treated with ABT-263 25 µM for 24 h. 750 µg of total proteins were subjected to Immunoprecipitation (IP) assay using monoclonal mouse anti ARTS Antibody (Ab). Western Blot analysis was performed using Bcl-2, Bcl-xL, ARTS, and Actin antibodies.

Figure 10:
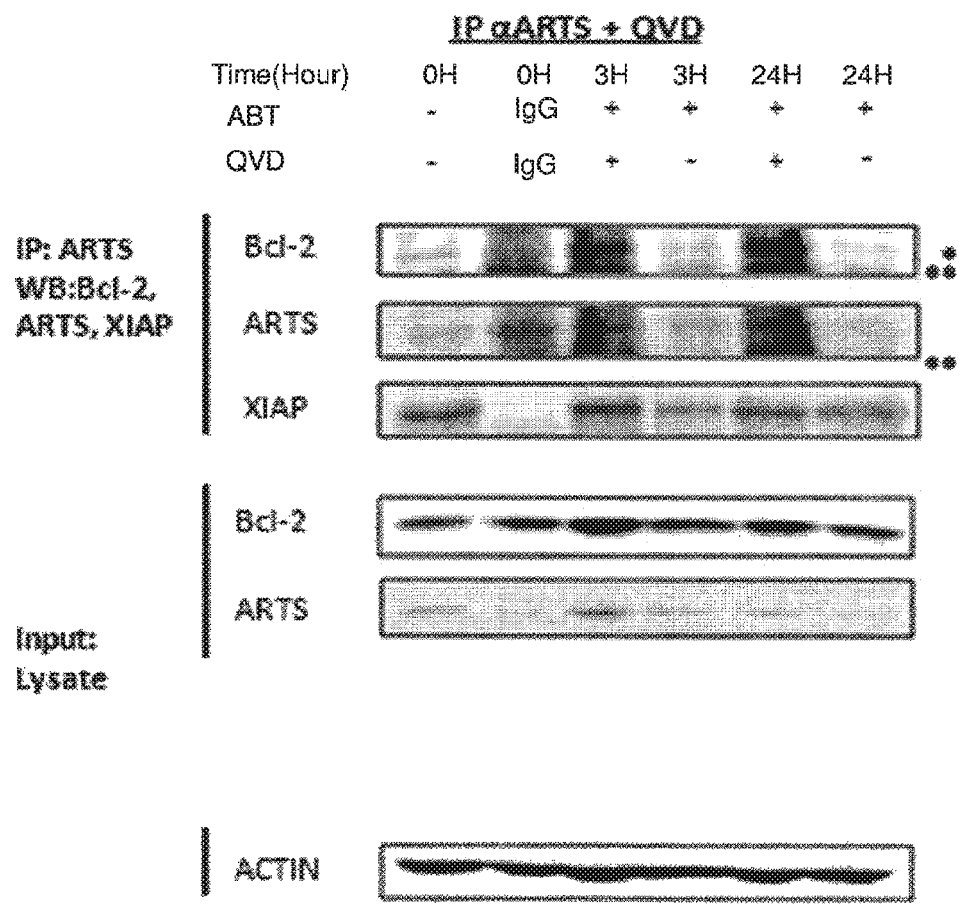

FIG. 10. ARTS binds to Bcl-2 via a different domain than BH3

The ability of ARTS to bind to Bcl-2 was tested after treatment with 25 µM ABT-263 for 3 and 24 hours, in presence or absence of caspase Inhibitor (QVD). 400 µg of total proteins were subjected to an IP assay using monoclonal mouse anti ARTS Ab. Western Blot analysis was performed by using Bcl-2, ARTS and Actin antibodies. **IgG light chain none specific band.

Figures 11A, 11B:
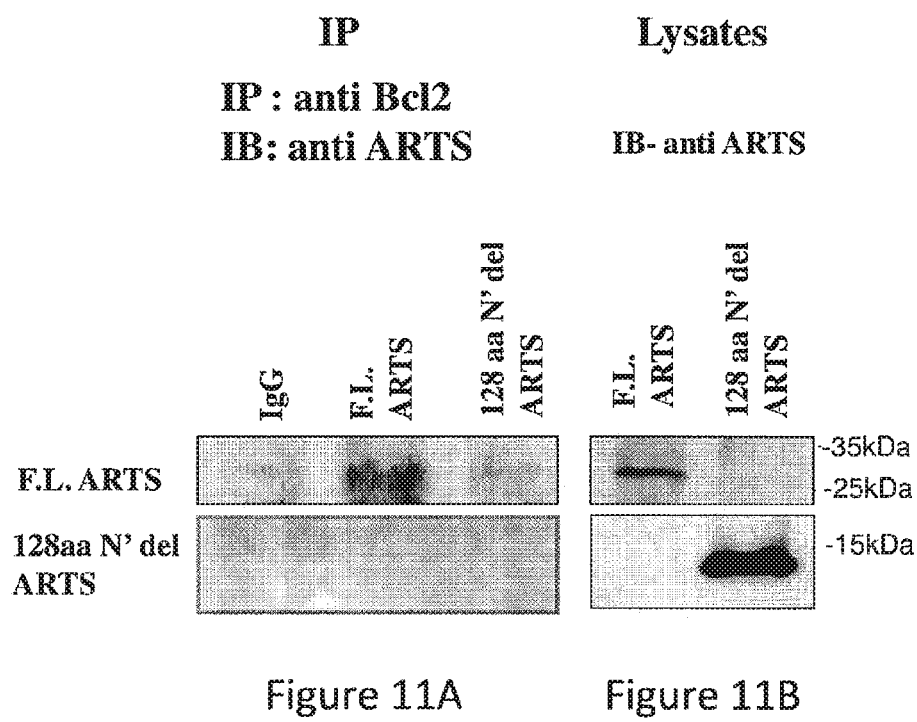

FIGS. 11A-11B. N-terminal fragment of ARTS is required for Bcl-2 binding

The ability of ARTS and a fragment of ARTS lacking the N' terminal 128 amino acid residues to Bcl-2 was tested in HeLa cells transfected with the Full length ARTS plasmid and 128 amino acids N' terminus deletion mutated ARTS.

FIG. 11A. shows a Western blot analysis Lysates of transfected cells that were pulled-down using Bcl-2 antibodies followed by Western-blot using anti-ARTS antibodies.

FIG. 11B. shows Western blot analysis of lysates of the transfected cells.

Figures 12A, 12B:
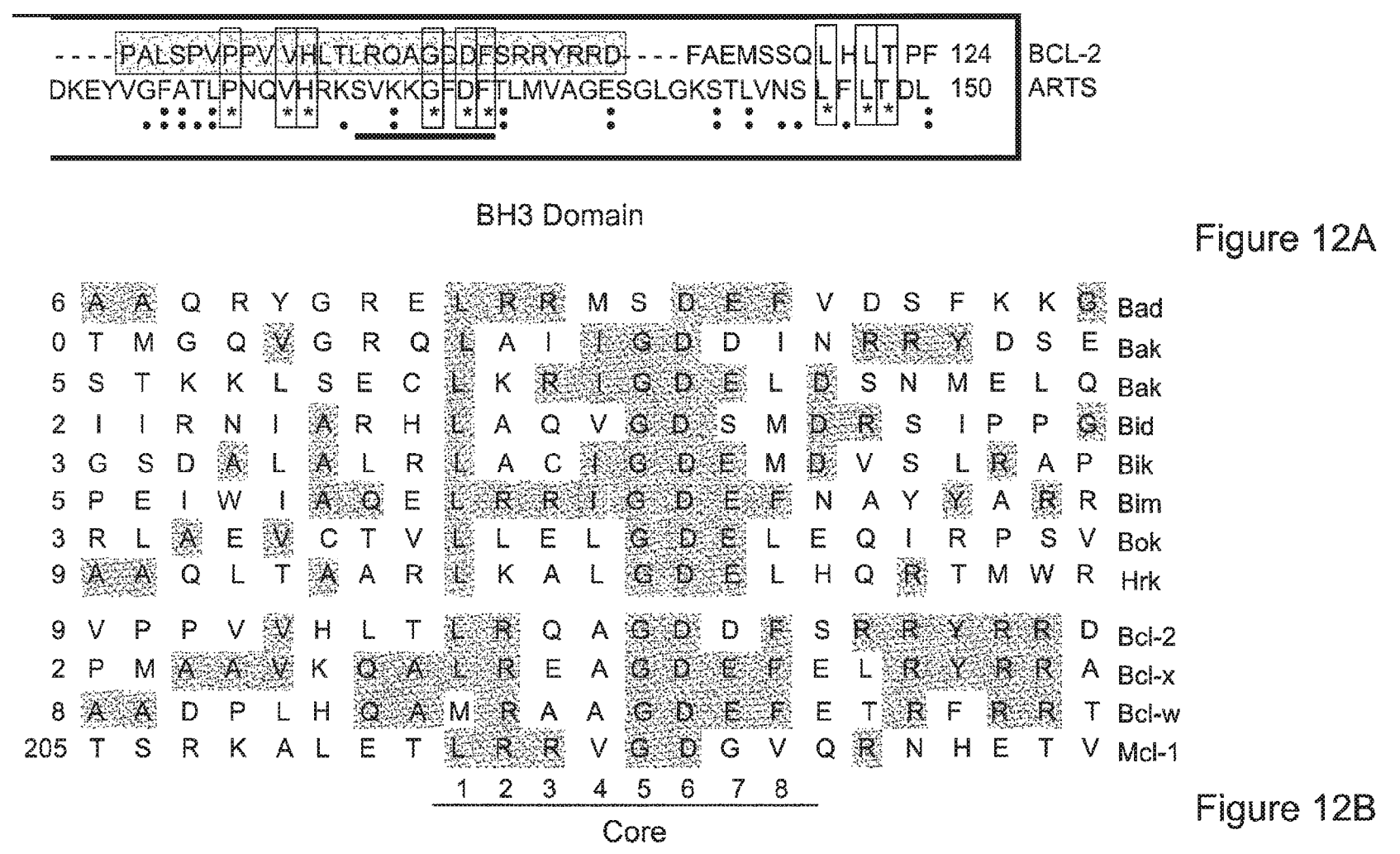

FIGS. 12A-12B. Homology between ARTS and Bcl-2

FIG. 12A. shows sequence alignment between amino acid residues 100-150 (SEQ ID NO: 40) of ARTS and residues 84 to 124 (SEQ ID NO: 38) of Bcl-2 indicating that the ARTS include a BH3-like domain. FIG. 12B. shows sequence alignment of BH3 domains in different Bcl-2 protein family members. The BH3 domains are characterized by the following sequence numbers: Bad is denoted by SEQ ID NO: 18, Bak is denoted by SEQ ID NO: 19, Bax is denoted by SEQ ID NO: 20, Bid is denoted by SEQ ID NO: 21, Bik is denoted by SEQ ID NO: 22, Bim is denoted by SEQ ID NO: 23, Bom is denoted by SEQ ID NO: 24, Hrk is denoted by SEQ ID NO: 25, Bcl-2 is denoted by SEQ ID NO: 26, Bcl-$X_L$ is denoted by SEQ ID NO: 27, Bcl-w is denoted by SEQ ID NO: 28, Mcl-1 is denoted by SEQ ID NO:29.

DETAILED DESCRIPTION OF THE INVENTION

The apoptotic pathway is an ordered process of programmed cell death that is often altered in various pathologic conditions associated with either an increased apoptosis or with a decreased apoptosis.

Modulating apoptosis by external means provides an important and promising approach that paves the way for a variety of therapeutically opportunities. For example, cancer is a condition associated with deregulated apoptosis, resulting in cells that displaying increased survival. Thus, inducing apoptosis is valuable as a defense mechanism against hyper proliferating cells. It was shown that Bcl-2 proteins that are anti-apoptotic proteins govern the pro-survival pathway and are over expressed in a variety of tumor types such small cell lung cancer, melanoma, prostate and breast cancer.

Cancer treatment is among others aimed in restoring the apoptotic capabilities of cancer cells. Further, inhibitors of Bcl-2 anti-apoptotic proteins are needed in order to revert to normal apoptotic processes and thus trigger tumor cell death.

The inventors have surprisingly found that upon induction of apoptosis, ARTS binds directly to both XIAP and Bcl-2, acting as a scaffold to bring these proteins together. This binding leads to a UPS mediated degradation of Bcl-2. Moreover, the inventors have unexpectedly found that ARTS comprise a BH3-like domain, acting as a Bcl-2 antagonist and as such, inhibits the anti-apoptotic activity of Bcl-2.

These surprising finding of the inventors is highly valuable and may lead to the development of new therapeutic strategies which target Bcl-2 and are directed towards the novel BH3-like domain in ARTS.

Furthermore, the inventors have found that treating cancer cells with a combination of the BH3-like Bcl-2 antagonist of the invention together with a BH3-mimetic compound, results in a synergetic effect. Moreover, the inventors have surprisingly found that for inducing apoptosis, BH3-mimetics antagonists of Bcl-2 require the antagonist of the invention that comprises ARTS and any fragments or peptides thereof that comprise a BH3-like domain.

The inventors have concluded that pathological conditions associated with deregulation of apoptosis and specifically, with Bcl-2 over-expression may be efficiently treated by combining BH3-mimetic antagonists of Bcl-2 with the BH3-like antagonists of the invention.

Thus, according to a first aspect, the invention relates to an antagonist of a Bcl-2 (B-cell lymphoma 2) prosurvival protein. The antagonist of the invention comprises ARTS (Apoptosis Related Protein in the TGF-beta Signaling Pathway) and any fragment, peptide, analogues and derivatives thereof. It should be noted that the fragment or peptide of ARTS comprises a Bcl-2 homology domain 3 (BH3)-like domain.

The invention provides a novel antagonist for Bcl-2 protein. As used herein the term Bcl-2 prosurvival protein refers to a proto-oncogenic protein known as an apoptosis inhibitor. The Bcl-2 protein forms the basis of a growing family of related proteins collectively denoted herein as Bcl-2 family of proteins. These proteins are known to control apoptotic cell death by the mitochondrial pathway.

As appreciated in the art, the members of the Bcl-2 family are either pro-survival or pro-apoptotic but regardless of their activity, they all share significant sequence and structural homology. Specifically, the Bcl-2 family of proteins is characterized by up to four regions of sequence homology, known as the Bcl-2 homology (BH) domains.

As such, the term "BH" as used herein refers to a Bcl-2 homology domain. This homology domain is part of a family formed by four types of sequence homology domains: BH1, BH2, BH3 and BH4.

As previously described in the art, the Bcl-2 family of proteins includes three different groups of proteins: the first group is a pro-survival or anti-apoptotic group denoted herein as "Bcl-2 pro-survival proteins", the second group is a pro-apoptotic group including BAX and BAK; and a third group denoted herein as BH3-only proteins that exhibit a pro-apoptotic activity.

The antagonist of the invention antagonizes the anti-apoptotic activity of the pro-survival Bcl-2 protein. The "Bcl-2 pro-survival proteins" or "anti-apoptotic" or "Bcl-2 like" as used herein denotes a group of proteins responsible for protecting cells from apoptotic stimuli and are sequentially characterized by containing all four BH domains.

It was previously shown that in response to an apoptotic stimulus, the balance of prosurvival and pro-apoptotic Bcl-2 proteins, and the specific interactions between them, determines the activity of the protein family. For example, as opposed to the Bcl-2 prosurvival proteins, the BH3-only proteins initiate apoptosis in response to diverse cellular stresses including DNA damage, growth factor deprivation, and endoplasmic reticulum stress. Activation of the BH3-only proteins may involve transcriptional up regulation or modification.

Several mechanisms have been suggested in the art to account for the diverse activity and tight control of apoptosis in the Bcl-2 family, some of which involve the Bax, Bak. Irrespective of the exact means it has become clear that the balance of prosurvival and pro-apoptotic (BH3-only) proteins is the key to this activation.

It has been previously suggested that the BH3 only proteins bind the Bcl-2 prosurvival proteins through their BH3-domain, inhibiting Bcl-2 proteins and thus promoting apoptosis. The structural basis of the interactions was shown to be associated with the ability of a BH3 domain to bind to a hydrophobic binding groove in the multidomain proteins, for example Bcl-2 prosurvival proteins. The term "hydrophobic binding groove" as used herein denotes a structural region in the surface of Bcl-2 prosurvival proteins. The hydrophobic groove comprises the BH3, BH1 and BH2 domains of these proteins. Further, the hydrophobic groove serves as a docking site for the BH3 domain of BH3-only proteins or any BH3-mimetics antagonist.

The term "BH3 mimetics antagonist" as used herein denotes compounds that mimic BH3 only proteins by binding of the hydrophobic grove of the Bcl-2 prosurvival proteins and antagonizing their activity. The term "BH3 mimetics antagonist" as used herein encompasses small molecules, peptides, oligonucleotides, aptamers and antibodies or any fragments thereof that target said domain.

As shown by the Examples, the antagonist of the invention, namely, ARTS and functional fragments and peptides thereof, bind directly to Bcl-2 in a manner that does not compete with compounds, known as BH3-mimetics that are directed towards the hydrophilic binding groove of Bcl-2 proteins. Therefore, it seems that the antagonist of the invention targets a different domain in the Bcl-2 molecule Moreover, the inventors have now found a novel BH3-like domain of ARTS that most likely, participates in the observed interaction with Bcl-2. The inventors have further showed that a fragment comprising residues 1-128 (the N-terminal portion) of ARTS (SEQ ID NO. 10), contains said BH3-like domain of ARTS is essential for Bcl-2 binding.

According to some other embodiments, the antagonist targets and binds a portion or a fragment of Bcl-2 that may be the "hydrophobic binding groove" sequence or any part thereof. However, the possibility that ARTS targets a different domain in Bcl-2 is also optional.

A "BH3 domain" as used herein is a domain comprised within Bcl-2 family members forming amphipathic alpha-helices. it should be noted that BIB-domains in pro-apoptotic Bcl-2 proteins bind tightly to hydrophobic grooves present in survival Bcl-2 proteins. As shown by FIG. 12B, the BH3 domain of different Bcl-2 family members comprise a core sequence of about eight conserved amino acid residues, including Leu and Arg (positions 1 and 2, Gly and Asp (positions 5 and 6) and Glu and Phe (positions 7 and 8). The core sequence of the BH3 domain of Bcl-2 comprises residues Leu-Arg-Gln-Ala-Gly-Asp-Asp-Phe (as denoted by SEQ ID NO. 37). As indicated by Example 8, alignment of the BH3 domain of Bcl-2 with the N-terminal portion of ARTS revealed a domain having residues that are similar to the residues of the BH3 domain of Bcl-2 (presenting the canonical sequence). Moreover, several residues were also found to be identical in domains that flank the BH3 core sequence. Therefore, as used herein "BH3-like domain" is a fragment or peptide of ARTS that comprises at least three out of eight residues that are identical to the BH3-core sequence of Bcl-2. According to one specific embodiment, these residues include the Gly residue in position 123 of ARTS, the Asp residue in position 125 of ARTS and Phe residue in position 126 of ARTS. it should be therefore appreciated that in certain embodiments, a fragment or peptide of ARTS that comprises a BH3-like domain, is meant a peptide of ARTS comprising at least one of Gly residue in position 123 of ARTS, the Asp residue in position 125 of ARTS and Phe residue in position 126 of ARTS. In yet another embodiment, the alignment performed by the inventors showed further identity in domains that flank the BH3-core domain. These residues include residue Pro in position 112 of ARTS, Val in position 115 of arts and His in position 116 of ARTS. Thus, in other specific embodiments, a fragment or peptide of ARTS that comprises the BH3-like domain of ARTS may comprise at least one of Pro in position 112 of ARTS, Val in position 115 of arts and His in position 116 of ARTS. Still further, the region that flank the C' terminal portion of the BH3-core sequence includes three residues that are identical to the residues in the Bcl-2 BH3 domain. These residues include Leu in position 145 of ARTS, Leu in position 147 of arts and Thr in position 148 of ARTS. Thus, in certain specific embodiments, a fragment or peptide of ARTS that comprises the BH3-like domain of ARTS may comprise at least one of Leu in position 145 of ARTS, Leu in position 147 of arts and Thr in position. 148 of ARTS.

As indicated above, the present invention relates to an antagonist of Bcl-2. An antagonist is a compound that competes with a specific protein, a ligand for example, on binding to another protein, a receptor for example. Such binding usually, induces a specific biological response or action that is blocked by the competing antagonist. Antagonists have affinity but no efficacy for their cognate binding protein and binding will disrupt the interaction and inhibit the function of such cognate protein. Antagonists mediate their effects by binding to the active (orthosteric=right place) site or to allosteric (=other place) sites on any cognate protein (or receptor, in case applicable), or they may interact at unique binding sites not normally involved in the biological regulation of the cognate protein.

According to another specific embodiment, the BH3-like antagonist of the invention may be a fragment or a peptide of ARTS comprising the amino acid sequence of any one of residues 1-128, 1-148, 106-148, 106-133, 112-148, 106-128, 112-128, 112-133, 106-140 and 112-126 of ARTS.

As used herein "ARTS" (apoptosis-related protein in the TGF-β signaling pathway) is a septin-like mitochondrial protein derived from alternative splicing of the H5/PNUTL2/hCDCrel2a/2b gene. ARTS acts as a tumor suppressor protein that functions as an antagonist of XIAP and thereby promotes apoptosis.

It should be appreciated that in certain embodiments, as used herein in the specification and in the claim section below, ARTS protein refers to the human ARTS (as denoted by SEQ ID NO. 9). More specifically, the human ARTS protein comprises an amino acid sequence of 274 amino acid residues as denoted by GenBank Accession No. AF176379, encoded by a nucleic acid sequence of SEQ ID NO. 8.

According to one specific embodiment, the antagonist of the invention may be a functional fragment of ARTS comprising an amino-acid sequence as denoted by any one of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 35 and SEQ ID NO: 36 respectively.

According to one specific embodiment, the antagonist of the invention may be a functional fragment of ARTS comprising amino-acid residues 1-128 of ARTS. More specifically, in certain embodiments this peptide comprises the amino acid sequence MIKRFLEDTTDDGELSKFVKDFS-GNASCHPPEAKTWASRPQVPEPRPQAPDLYD DDLE-FRPPSRPQSSDNQQYFCAPAPLSPSARPR-SPWGKLDPYDSSEDDKEYVGF ATLPNQVHRKSVKKGFDFTL as denoted by SEQ ID NO: 10.

According to one specific embodiment, the antagonist of the invention may be a functional fragment of ARTS comprising amino-acid residues 1-148 of ARTS. More specifically, in certain embodiments this peptide comprises the amino acid sequence MIKRFLEDTTDDGELSKFVKDFS-GNASCHPPEAKTWASRPQVPEPRPQAPDLYD DDLE-FRPPSRPQSSDNQQYFCAPAPLSPSARPR-SPWGKLDPYDSSEDDKEYVGF ATLPNQVHRKSVKKGFDFTLMVAGESGLGK-STLVNSLFLT, such fragment or peptide is denoted by SEQ ID NO: 11.

According to one specific embodiment, the antagonist of the invention may be a functional fragment of ARTS comprising amino-acid residues 106-148 of ARTS. More specifically, in certain embodiments this peptide comprises the amino acid sequence VGFATLPNQVHRKSVKKGFDFTLMVAGESGLGK-STLVNSLFLT, such fragment or peptide is denoted by SEQ ID NO: 12.

According to one specific embodiment, the antagonist of the invention may be a functional fragment of ARTS comprising amino-acid residues 106-133 of ARTS. More specifically, in certain embodiments this peptide comprises the amino acid sequence VGFATLPNQVHRKSVKKGFDFTLMVAGE, such fragment or peptide is denoted by SEQ ID NO. 13.

According to one specific embodiment, the antagonist of the invention may be a functional fragment of ARTS comprising amino-acid residues 106-128 of ARTS. More specifically, in certain embodiments this peptide comprises the amino acid sequence VGFATLPNQVHRKSVKKGFDFTL, such fragment or peptide is denoted by SEQ ID NO. 14.

According to one specific embodiment, the antagonist of the invention may be a functional fragment of ARTS comprising amino-acid residues 112-148 of ARTS. More specifically, such fragment or peptide comprises the amino acid sequence PNQVHRKSVKKGFDFTLMVAGESGLGK-STLVNSLFLT as denoted by SEQ ID NO. 15.

According to one specific embodiment, the antagonist of the invention may be a functional fragment of ARTS comprising amino-acid residues 112-133 of ARTS. More specifically, in certain embodiments this peptide comprises the amino acid sequence PNQVHRKSVKKGFDFTLMVAGE, such fragment or peptide is denoted by SEQ ID NO: 16.

According to one specific embodiment, the antagonist of the invention may be a functional fragment of ARTS comprising amino-acid residues 112-128 of ARTS. More specifically, in certain embodiments this peptide comprises the amino acid sequence PNQVHRKSVKKGFDFTL such fragment or peptide is denoted by SEQ ID NO. 17.

According to one specific embodiment, the antagonist of the invention may be a functional fragment of ARTS comprising amino-acid residues 106-140 of ARTS. More specifically, in certain embodiments this peptide comprises the amino acid sequence VGFATLPNQVHRKSVKKGFDFTLMVAGESGLGKST, such fragment or peptide is denoted by SEQ ID NO. 35.

According to one specific embodiment, the antagonist of the invention may be a functional fragment of ARTS comprising amino-acid residues 112-126 of ARTS. More specifically, in certain embodiments this peptide comprises the amino acid sequence PNQVHRKSVKKGFDF, such fragment or peptide is denoted by SEQ ID NO. 36.

It should be noted that according to one particular embodiment, the antagonist of the invention may comprise any fragment of ARTS provided that said fragment is not a fragment comprising the C' terminal 68 amino acid residues as denoted by SEQ ID NO. 30. In yet another particular embodiment, the antagonist of the invention may comprise any fragment of ARTS with the proviso that said fragment is not a fragment comprising the C' terminal 27 amino acid residues as denoted by SEQ ID NO. 31. Still further, according to another embodiment, the antagonist of the invention may comprise any fragment of ARTS provided that said fragment is not a fragment comprising the C' terminal 9 amino acid residues 266-274 as denoted by SEQ ID NO. 32. According to another embodiment, the antagonist of the invention may comprise any fragment of ARTS provided that said fragment is not a fragment comprising the C' terminal 9 amino acid residues 248-256 as denoted by SEQ ID NO. 33. And according to another embodiment, the antagonist of the invention may comprise any fragment of ARTS provided that said fragment is not a fragment comprising the C' terminal 9 amino acid residues 257-265 as denoted by SEQ ID NO. 34.

According to another embodiment, the antagonist of the invention may antagonize any Bcl-2 prosurvival protein, for example, at least one of Bcl-2, Bcl-xL, Mcl-1, Bcl-w, A1/Bfl-1 and Bcl-B/Bcl2L10.

More specifically, in some embodiments the antagonist of the invention binds and antagonizes Bcl-2. Bcl-2 (B-cell CLL/lymphoma 2) as used herein, is an integral outer mitochondrial membrane protein that blocks the apoptotic death of some cells such as lymphocytes. Bcl-2 suppresses apoptosis in a variety of cell systems including factor-dependent lympho-hematopoietic and neural cells. It regulates cell death by controlling the mitochondrial membrane permeability. Bcl-2 appears to function in a feedback loop system with caspases, it inhibits caspase activity either by preventing the release of cytochrome c from the mitochondria and/or by binding to the apoptosis-activating factor (APAF-1). It should be noted that in certain embodiments, the invention refers to the human Bcl-2 protein as denoted by GenBank Accession No. NP_000624 and SEQ ID NO: 3 and NP_000648 of SEQ ID NO:4), encoded by the Bcl-2 gene of GenBank Accession No. NM_000633 of SEQ ID NO: 1 and NM_000657 of SEQ ID NO:2.

In yet another embodiment, the antagonist of the invention binds and antagonizes Bcl-xL. B-cell lymphoma-extra large (Bcl-xL) as used herein, is a transmembrane molecule in the mitochondria. It is a member of the Bcl-2 family of proteins, and acts as a pro-survival protein by preventing the release of mitochondrial contents such as cytochrome c, which would lead to caspase activation. In certain embodiments the invention relates to the human Bcl-xL protein (GenBank Accession No. CAA80661 SEQ ID NO: 6), encoded by the Bcl-xL gene as denoted by GenBank Accession No. Z23115 and SEQ ID NO: 5.

In yet another embodiment, the antagonist of the invention binds and antagonizes any one of the human Bcl-2 pro-survival proteins Mcl-1, Bcl-w, A1/Bfl-1 and Bcl-B/Bcl2L10 as denoted by accession number: AAF64255, AAB09055, NP_033872 and NP_065129, respectively.

As shown in Example 1 provided herein below (FIGS. 2A and 2B), down regulation of Bcl-2 protein levels was observed during induction of apoptosis. Further, induction of apoptosis results in accumulation of polyubiquitinated forms of Bcl-2. Interestingly, an accumulation of Bcl-2 levels was found during induction of apoptosis in cells that were treated with proteasome inhibitor, namely, during proteasome inactivation. This suggests that the down-regulation of Bcl-2 levels observed during apoptosis may be mediated by the ubiquitin-proteasome machinery (UPS).

Thus, in certain embodiments, the antagonist of the invention comprising ARTS and any BH3-like containing fragments or peptides thereof, mediates ubiquitin proteasome system (UPS) degradation of said Bcl-2 prosurvival protein, thereby enhancing and inducing apoptosis.

As used herein the term "ubiquitin proteasome system" denotes a multi component system that identifies and degrades unneeded, damaged or misfolded proteins by breaking peptide bonds (proteolysis) of the protein in the cytoplasm of cells. As appreciated in the art, degradation of a protein via the UPS involves two discrete and successive steps. In the first step, proteins are tagged for degradation with a small protein called ubiquitin. The tagging reaction is catalyzed by enzymes called ubiquitin ligases. Once a protein is tagged with a single ubiquitin molecule, this is a signal to other ligases to attach additional ubiquitin molecules.

More specifically, conjugation of ubiquitin, a highly evolutionarily conserved 76 amino acid residue polypeptide, to the protein substrate proceeds via a three-step cascade mechanism involving E1, E2 and E3 enzymes. By successively adding activated ubiquitin moieties to internal lysine residues on the previously conjugated ubiquitin molecule, a polyubiquitin chain is synthesized that is subsequently recognized by the downstream 26S proteasome complex.

In the second step, degradation of polyubiquitinated substrates is carried out by a large, protease complex, referred to as the 26S proteasome that does not recognize nonmodified substrates. The proteasomes are multicatalytic protease protein complexes found in all cells that degrades polyubiquitinated proteins to short peptides by breaking peptide bonds (proteolysis). Following degradation of the substrate, short peptides derived from the substrate are released, along with reusable ubiquitin.

It should be noted that the ubiquitin-proteasome system (UPS) plays a central and complex role in regulating apoptosis by directly targeting key cell death proteins, including caspases.

In this connection it is interesting to note that the antagonist of the invention serves as a scaffold, and by binding both, Bcl-2 and XIAP, that is a known E3 ligase, facilitates UPS mediated degradation of the anti-apoptotic Bcl-2. Degradation of said pro-survival protein leads to and enhances apoptosis.

Thus, in some embodiments, the degradation of Bcl-2 prosurvival proteins is induced during onset of apoptosis. In some other embodiments, the antagonist according to the invention mediates ubiquitin proteasome system (UPS) degradation of said Bcl-2 prosurvival protein, thereby enhancing and inducing apoptosis.

The term "apoptosis" refers to a regulated network of biochemical events which lead to a selective form of cell suicide and is characterized by readily observable morphological and biochemical phenomena. Cells undergoing apoptosis show characteristic morphological and biochemical features. These features include chromatin aggregation or condensation, DNA fragmentation, nuclear and cytoplasmic condensation, partition of cytoplasm and nucleus into membrane bound vesicles (apoptotic bodies) which contain ribosomes, morphologically intact mitochondria and nuclear material. Cytochrome C release from mitochondria is seen as an indication of mitochondrial dysfunction accompanying apoptosis.

As indicated above, apoptosis is a tightly controlled form of active cell death that is necessary for development and organismal homeostasis. Death by the apoptotic pathway is achieved among others, by the activation of a family of highly potent and specific proteases, termed caspases (for cysteine-aspartate protease).

The activity of caspases is tightly regulated and the cell maintains several "checkpoints" to control their activity. The first level of regulation is intrinsic to caspases themselves. Caspases are initially transcribed as weakly active zymogens, which only upon proper stimulation are cleaved to form the active enzyme.

The second level of caspase regulation is achieved by inhibitors, namely by a family of proteins called IAPs (Inhibitor of Apoptosis Protein).

As mentioned above, the antagonist of the invention is a dual antagonist that binds both, the X-linked-Inhibitor of Apoptosis (XIAP) protein and Bcl-2, thereby mediating the UPS degradation of both anti-apoptotic proteins and induce or enhance apoptosis.

As used herein the term "IAPs" denotes a family of proteins that harbor between one to three copies of a baculovirus IAP repeat (BIR) domain that enable interaction with activated caspases. It was previously suggested that the BIR domains of certain IAPs, in particular XIAP, have the ability to directly inhibit caspase activity in vitro.

X-linked inhibitor of apoptosis protein (XIAP), also known as inhibitor of apoptosis protein 3 (IAP3) and baculoviral IAP repeat-containing protein 4 (BIRC) denotes a protein known to stop an apoptotic process and thus inhibit cell death. In human, XIAP is produced by a gene named XIAP gene located on the X chromosome. XIAP is also called human IAP-like Protein (hILP), because it is not as well conserved as the human LAPS: hIAP-1 and hIAP-2. XIAP is the most potent human IAP protein currently identified.

XIAP belongs to a family of apoptotic suppressor proteins. Members of this family share a conserved motif termed, baculovirus IAP repeat (BIR domain), which is necessary for their anti-apoptotic function. XIAP acts as a direct caspase inhibitor by directly binding to the active site pocket of CASP3 and CASP7 and obstructs substrate entry. It further inactivates CASP9 by keeping it in a monomeric, inactive state.

It should be noted that in certain embodiments, the invention relates to the human XIAP protein (GenBank Accession Nos. NP_001158, NP_001191330) encoded by the XIAP gene (GenBank Accession Nos. NM_001167, NM_001204401).

As recently shown by the inventors, ARTS binds to XIAP through a domain comprising 27 residues covering the C-terminus of ARTS. This interaction induces auto degradation of XIAP. It is therefore interesting to note that ARTS is firstly shown by the present invention as playing an essential role in inhibiting both apoptotic pathways governed by IAP on one hand and by Bcl-2 on the other hand, thereby enhancing apoptosis more effectively.

The inventors have shown that administration of the antagonist of the invention with a BH3-mimetic compound enhances the pro-apoptotic effect thereof. Therefore, similar interaction of the antagonist of the invention with any BH3-containing pro-apoptotic protein, may result in enhancement of apoptosis. Thus, according to certain embodiments, the antagonist of the invention enhances apoptosis, in certain embodiments, mediated by Bcl-2 family members having a pro-apoptotic activity. Such Bcl-2 pro-apoptotic protein may be for example any one of Bax, Bak, Bnip3, Nix/Bnip3L, Bid, Noxa, Puma and Bad.

It should be noted that by facilitating Bcl-2 degradation mediated by XIAP, the BH3 antagonist of the invention, ARTS and any fragments or peptides thereof comprising a BH3-like domain, inhibits the pro-survival or anti-apoptotic effect of Bcl-2 protein. The terms "inhibition", "moderation" or "attenuation" as referred to herein, relate to the retardation, restraining or reduction of the anti-apoptotic activity of a Bcl-2 pro-survival protein. Such inhibition may be of about 1% to 99.9%, specifically, about 1% to about 95%, about 5% to 90%, about 10% to 85%, about 15% to 80%, about 20% to 75%, about 25% to 70%, about 30% to 65%, about 35% to 60%, about 40% to 55%, about 45% to 50%. More specifically, about 5%, 10%, 15%, 20%, 25%, 30%, 35%, 40%, 45%, 50%, 55%, 60%, 65%, 70%, 75%, 80%, 85%, 90%, 95% or 99.9%.

It should be further noted that by inhibiting the anti-apoptotic action of Bcl-2 proteins, the BH3-like antagonist of the invention induces or enhances apoptosis. More specifically, antagonists of the invention, specifically, ARTS and any fragments or peptides thereof comprising the BH3-like domain, as well as any of the compositions and methods of the invention described herein after, may lead to an increase, enhancement, induction or elevation in apoptosis of treated cells, said increase, induction or elevation of apoptosis may be an increase by about 1% to 99.9%, specifically, about 1% to about 95%, about 5% to 90%, about 10% to 85%, about 15% to 80%, about 20% to 75%, about 25% to 70%, about 30% to 65%, about 35% to 60%, about 40% to 55%, about 45% to 50%. More specifically, about 5%, 10%, 15%, 20%, 25%, 30%, 35%, 40%, 45%, 50%, 55%, 60%, 65%, 70%, 75%, 80%, 85%, 90%, 95% or 99.9%. More specifically, an increase of about 5%, 10%, 15%, 20%, 25%, 30%, 35%, 40%, 45%, 50%, 55%, 60%, 65%, 70%, 75%, 80%, 85%, 90%, 95% or 99% as compared to untreated control.

With regards to the above, it is to be understood that, where provided, percentage values such as, for example, 10%, 50%, 120%, 500%, etc., are interchangeable with "fold change" values, i.e., 0.1, 0.5, 1.2, 5, 10, 20, 30, 40, 50, 60, 70, 80, 90, 100 etc., respectively.

Certain embodiments of the invention involve the use of ARTS and peptides thereof for the methods and compositions as will be described herein after. It should be appreciated that such peptides or amino acid sequences are preferably isolated and purified molecules, as defined herein. The term "purified" or "isolated" refers to molecules, such as amino acid sequences, or peptides that are removed from their natural environment, isolated or separated. An "isolated peptide" is therefore a purified amino acid sequence. "Substantially purified" molecules are at least 60% free, preferably at least 75% free, and more preferably at least 90% free from other components with which they are naturally associated. As used herein, the term "purified" or "to purify" also refers to the removal of contaminants from a sample.

As noted above, the present invention provides Bcl-2 antagonists comprising ARTS polypeptide or any fragment or peptide thereof. The term "polypeptide" as used herein refers to amino acid residues, connected by peptide bonds. A polypeptide sequence is generally reported from the N-terminal end containing free amino group to the C-terminal end containing free carboxyl group.

More specifically, "Amino acid molecule", "Amino acid sequence" or "peptide sequence" is the order in which amino acid residues connected by peptide bonds, lie in the chain in peptides and proteins. The sequence is generally reported from the N-terminal end containing free amino group to the C-terminal end containing amide. Amino acid sequence is often called peptide, protein sequence if it represents the primary structure of a protein, however one must discern between the terms "Amino acid sequence" or "peptide sequence" and "protein", since a protein is defined as an amino acid sequence folded into a specific three-dimensional configuration and that had typically undergone post-translational modifications, such as phosphorylation, acetylation, glycosylation, manosylation, amidation, carboxylation, sulfhydryl bond formation, cleavage and the like.

Amino acids, as used herein refer to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. "Amino acid analogs" refers to compounds that have the same fundamental chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid Amino acids may be referred to herein by either their commonly known three letter symbols or by the one-letter symbols recommended by the IUPAC-IUB Biochemical Nomenclature Commission.

It should be noted that in addition to any of the ARTS derived fragments or peptides described herein, the invention further encompasses any derivatives, analogues, variants or homologues of any of the peptides. The term "derivative" is used to define amino acid sequences (polypeptide), with any insertions, deletions, substitutions and modifications to the amino acid sequences (polypeptide) that do not alter the activity of the original polypeptides. By the term "derivative" it is also referred to homologues, variants and analogues thereof, as well as covalent modifications of a polypeptides made according to the present invention.

It should be further noted that the polypeptides according to the invention can be produced synthetically, or by recombinant DNA technology. Methods for producing polypeptides peptides are well known in the art.

In some embodiments, derivatives include, but are not limited to, polypeptides that differ in one or more amino acids in their overall sequence from the polypeptides defined herein (either the ARTS protein or any fragment or peptide derived therefrom according to the invention), polypeptides that have deletions, substitutions, inversions or additions.

In some embodiments, derivatives refer to polypeptides, which differ from the polypeptides specifically defined in the present invention by insertions of amino acid residues. It should be appreciated that by the terms "insertions" or "deletions", as used herein it is meant any addition or deletion, respectively, of amino acid residues to the polypeptides used by the invention, of between 1 to 50 amino acid residues, between 20 to 1 amino acid residues, and specifically, between 1 to 10 amino acid residues. More particularly, insertions or deletions may be of any one of 1, 2, 3, 4, 5, 6, 7, 8, 9, or 10 amino acids. It should be noted that the insertions or deletions encompassed by the invention may occur in any position of the modified peptide, as well as in any of the N' or C' termini thereof.

The peptides of the invention may all be positively charged, negatively charged or neutral. In addition, they may be in the form of a dimer, a multimer or in a constrained conformation, which can be attained by internal bridges, short-range cyclizations, extension or other chemical modifications.

The polypeptides of the invention can be coupled (conjugated) through any of their residues to another peptide or agent. For example, the polypeptides of the invention can be coupled through their N-terminus to a lauryl-cysteine (LC) residue and/or through their C-terminus to a cysteine (C) residue.

Further, the peptides may be extended at the N-terminus and/or C-terminus thereof with various identical or different amino acid residues. As an example for such extension, the peptide may be extended at the N-terminus and/or C-terminus thereof with identical or different amino acid residue/s, which may be naturally occurring or synthetic amino acid residue/s. An additional example for such an extension may be provided by peptides extended both at the N-terminus and/or C-terminus thereof with a cysteine residue. Naturally, such an extension may lead to a constrained conformation due to Cys-Cys cyclization resulting from the formation of a disulfide bond. Another example may be the incorporation of an N-terminal lysyl-palmitoyl tail, the lysine serving as linker and the palmitic acid as a hydrophobic anchor. In addition, the peptides may be extended by aromatic amino acid residue/s, which may be naturally occurring or synthetic amino acid residue/s, for example, a specific aromatic amino acid residue may be tryptophan. The peptides may be extended at the N-terminus and/or C-terminus thereof with various identical or different organic moieties, which are not naturally occurring or synthetic amino acids. As an example for such extension, the peptide may be extended at the N-terminus and/or C-terminus thereof with an N-acetyl group.

For every single peptide sequence defined by the invention and disclosed herein, this invention includes the corresponding retro-inverse sequence wherein the direction of the peptide chain has been inverted and wherein all the amino acids belong to the D-series.

The invention also encompasses any homologues of the polypeptides (either the ARTS protein or any fragments or peptides thereof) specifically defined by their amino acid sequence according to the invention. The term "homologues" is used to define amino acid sequences (polypeptide) which maintain a minimal homology to the amino acid sequences defined by the invention, e.g. preferably have at least about 65%, more preferably at least about 75%, even more preferably at least about 85%, most preferably at least about 95% overall sequence homology with the amino acid sequence of any of the polypeptide as structurally defined above, e.g. of a specified sequence, more specifically, an amino acid sequence of the polypeptides as denoted by any one of SEQ ID NO. 9, 10, 11, 12, 13, 14, 15, 16, 17, 35 and 36.

More specifically, "Homology" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Neither N-nor C-terminal extensions nor insertions or deletions shall be construed as reducing identity or homology. Methods and computer programs for the alignment are well known in the art.

In some embodiments, the present invention also encompasses polypeptides which are variants of, or analogues to, the polypeptides specifically defined in the invention by their amino acid sequence. With respect to amino acid sequences, one of skill will recognize that individual substitutions, deletions or additions to peptide, polypeptide, or protein sequence thereby altering, adding or deleting a single amino acid or a small percentage of amino acids in the encoded sequence is a "conservatively modified variant", where the alteration results in the substitution of an amino acid with a chemically similar amino acid.

Conservative substitution tables providing functionally similar amino acids are well known in the art. Such conservatively modified variants are in addition to and do not exclude polymorphic variants, interspecies homologues, and alleles and analogous peptides of the invention.

For example, substitutions may be made wherein an aliphatic amino acid (G, A, I, L, or V) is substituted with another member of the group, or substitution such as the substitution of one polar residue for another, such as arginine for lysine, glutamic for aspartic acid, or glutamine for asparagine. Each of the following eight groups contains other exemplary amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

More specifically, amino acid "substitutions" are the result of replacing one amino acid with another amino acid having similar structural and/or chemical properties, i.e., conservative amino acid replacements Amino acid substitutions may be made on the basis of similarity in polarity, charge, solubility, hydrophobicity, hydrophilicity, and/or the amphipathic nature of the residues involved. For example, nonpolar "hydrophobic" amino acids are selected from the group consisting of Valine (V), Isoleucine (I), Leucine (L), Methionine (M), Phenylalanine (F), Tryptophan (W), Cysteine (C), Alanine (A), Tyrosine (Y), Histidine (H), Threonine (T), Serine (S), Proline (P), Glycine (G), Arginine (R) and Lysine (K); "polar" amino acids are selected from the group consisting of Arginine (R), Lysine (K), Aspartic acid (D), Glutamic acid (E), Asparagine (N), Glutamine (Q); "positively charged" amino acids are selected form the group consisting of Arginine (R), Lysine (K) and Histidine (H) and wherein "acidic" amino acids are selected from the group consisting of Aspartic acid (D), Asparagine (N), Glutamic acid (E) and Glutamine (Q).

The derivatives of any of the polypeptides according to the present invention, e.g. of a specified sequence of any one of the polypeptides of SEQ ID NO. 9 to 17 and 35-36, may vary in their size and may comprise the full length polypeptide or any fragment thereof.

In certain embodiments the peptide compounds of the invention may comprise one or more amino acid residue surrogate. An "amino acid residue surrogate" as herein defined is an amino acid residue or peptide employed to produce mimetics of critical function domains of peptides.

Examples of amino acid surrogate include, but are not limited to chemical modifications and derivatives of amino acids, stereoisomers and modifications of naturally occurring amino acids, non-protein amino acids, post-translationally modified amino acids, enzymatically modified amino acids, and the like. Examples also include dimers or multimers of peptides. An amino acid surrogate may also include any modification made in a side chain moiety of an amino acid. This thus includes the side chain moiety present in naturally occurring amino acids, side chain moieties in modified naturally occurring amino acids, such as glycosylated amino acids. It further includes side chain moieties in stereoisomers and modifications of naturally occurring protein amino acids, non-protein amino acids, post-translationally modified amino acids, enzymatically synthesized amino acids, derivatized amino acids, constructs or structures designed to mimic amino acids, and the like.

It should be appreciated that the invention further encompass any of the peptides of the invention any serogates thereof, any salt, base, ester or amide thereof, any enantiomer, stereoisomer or disterioisomer thereof, or any combination or mixture thereof. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts.

It should be noted that the invention further encompasses any peptidomimetic compound mimicking the BH3-like antagonist of the invention and any fragment or peptide thereof. When referring to peptidomimetics, what is meant is a compound that mimics the conformation and desirable features of a particular natural peptide but avoids the undesirable features, e.g., flexibility and bond breakdown. From chemical point of view, peptidomimetics can have a structure without any peptide bonds, nevertheless, the compound is peptidomimetic due to its chemical properties and not due to chemical structure. Peptidoinimetics (both peptide and non-peptidyl analogues) may have improved properties (e.g., decreased proteolysis, increased retention or increased bioavailability). It should be noted that peptidomimetics may or may not have similar two-dimensional chemical structures, but share common three-dimensional structural features and geometry. Each peptidomimetic may further have one or more unique additional binding elements.

The antagonist provided by the invention may be formulated in a composition.

Thus, according to a second aspect, the invention provides a composition comprising an effective amount of at least one antagonist of a Bcl-2 prosurvival protein. More specifically, such antagonist comprises ARTS or any fragment, peptide, analogues and derivatives thereof. It must be noted that such fragments or peptides of ARTS comprise a BH3-like domain.

According to certain embodiments, the composition of the invention comprises an ARTS fragment or peptide comprising the amino acid sequence of any one of residues 1-128, 1-148, 106-148, 106-133, 112-148, 112-128, 112-133, 106-140 and 112-126 of ARTS.

According to more specific embodiments, the ARTS fragment or peptide used for the composition of the invention may comprise an amino acid sequence as denoted by any one of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 35 and SEQ ID NO: 36, respectively.

In yet other embodiments, the BH3-like containing fragments of ARTS of the invention may antagonize any Bcl-2 family member with prosurvival activity, specifically, any one of Bcl-2, Bcl-xL, Mcl-1, Bcl-w, A1/Bfl-1 and Bcl-B/Bcl2L10.

Further embodiments of the invention provide a composition comprising an antagonist that mediates UPS degradation of said Bcl-2 prosurvival protein, thereby enhancing or inducing apoptosis.

In yet other embodiments, the BH3-like containing fragments of ARTS of the invention may interact with any Bcl-2 family member having a pro-apoptotic activity thereby enhancing or inducing apoptosis. In certain embodiments, such pro-apoptotic Bcl-2 family member may include any one of Bax, Bak, Bnip3, Nix/Bnip3L, Bid, Noxa, Puma, and Bad.

According to another embodiment, the composition of the invention may be a pharmaceutical composition for treating, inhibiting, preventing, ameliorating or delaying the onset of a Bcl-2 over-expressing pathological disorder. Such composition optionally may further comprise at least one pharmaceutically acceptable carrier, diluent or excipient.

The phrases "Bcl-2-over-expressing-disorder" and "Bcl-2-mediated disorder" refer to pathological and disease conditions in which a Bcl-2 protein is over-expressed as indicated herein above. Moreover, this term also encompasses conditions in which Bcl-2 plays a role. Such roles can be directly related to the pathological condition or can be indirectly related to the condition. The feature common to this class of conditions is that they can be ameliorated by inhibiting the expression of activity of, function of, or association with Bcl-2 proteins.

The term "over expressed" refers to an increase in the measurable expression level of Bcl-2 gene as measured by the amount of RNA and/or the amount of protein in a sample as compared with the measurable expression level of Bcl-2 gene in a second sample, specifically, a control sample. "Over expressed Bcl-2" can be measured and evaluated using the ratio of the level of expression of Bcl-2 in a sample as compared with the mean expression level of Bcl-2 of a control sample wherein the ratio is not equal and specifically, is above 1.0. When determining over expression on the basis of the ratio, an RNA or protein is over expressed if the ratio of the level of expression in a first sample as compared with a second sample is greater than 1.0. For example, a ratio of greater than 1.2, 1.5, 1.7, 2, 3, 4, 5, 6, 7, 8, 9, 10, 20, 30, 40, 50, 60, 70, 80, 90, 100 or more.

More specifically, disorders displaying "over or increased expression" or "up regulation" of Bcl-2 refer to disorders which demonstrate at least 10% or more, for example, 20%, 30%, 40%, or 50%, 60%, 70%, 80%, 90% or more, or 1.1 fold, 1.2 fold, 1.4 fold, 1.6 fold, 1.8, 1.9, 2, 3, 4, 5, 6, 7, 8, 9, 10, 20, 30, 40, 50, 60, 70, 80, 90, 100 fold, or more increase in Bcl-2 expression (as measured by RNA expression or protein expression), relative to a control sample.

Thus, a Bcl-2 over-expressing pathological disorder is meant a disorder characterized by over-expression of Bcl-2 in said subject or in a diseased tissue of said subject as compared to a healthy subject or a healthy tissue of the same subject.

It should be noted that the Bcl-2 over-expressing disorder may be caused by chromosomal translocation, hypo-methylation and down regulation of the microRNAs that target Bcl-2.

In yet another embodiment, the pharmaceutical composition of the invention is specifically applicable for treating Bcl-2 over-expressing proliferative disorders.

As shown by the invention, contacting cells with both, the BH3-mimetic antagonist ABT 263 and the antagonist of the invention ARTS, that comprises a BH3-like domain, increased binding of Bcl-2 to ARTS, and enhanced apoptosis. Therefore, a combined therapy is further established by the invention.

Thus, according to certain embodiments, the pharmaceutical composition of the invention may be adapted for use before, simultaneously with, after or any combination thereof at least one BH3 mimetics compound. In yet another embodiment, the composition of the invention may be adapted for use before, simultaneously with, after or any combination thereof at least one Bcl-2 pro-apoptotic protein or any combinations thereof.

Moreover, further embodiments of the invention encompass the option of combining a further active therapeutic compound in the pharmaceutical composition of the invention. In some specific embodiments, such compound may be at least one BH3 mimetics compound antagonist, or alternatively or additionally, at least one Bcl-2 pro-apoptotic protein or any combinations thereof.

According to one embodiment, the BH3 mimetics mimic at least part of BH3-only proteins. More specifically, the BH3-only protein may be any one of Bid, Bim, Puma, Noxa, Bad, Bmf, Hrk and Bik and any fragments analogues, derivatives or combinations thereof.

As shown in the Example 7 herein below, incubating cells with the antagonist according to the invention together with a BH3-mimetics antagonist (ABT-263) showed enhanced Bcl-2 binding and therefore suggest that ABT-263 is not competing with the antagonist of the invention ARTS, on binding to Bcl-2. Analysis of the structure of the N-terminal portion of ARTS showed a BH3-like domain. Interestingly, this portion of ARTS was shown as necessary for the observed interaction with Bcl-2.

These results indicate that the antagonist described inhere targets and binds a region in the Bcl-2 prosurvival proteins that according to some embodiments, may include at least part of the "hydrophobic binding groove", in a manner that cannot interfere with binding of the BH3 mimetic drug ABT 263 to its specific target.

Thus, combined therapy provided by the invention encompasses combining of the antagonist of the invention ARTS with ABT 263. It should be noted that ABT-263 as used herein, is a small molecule that inhibits Bcl-2 and Bcl-XL and marketed by Abbott laboratories under the generic name of Navitoclax. ABT-263 inhibits the anti-intrinsic apoptotic pathway via the BH3 domain. ABT-263 Bcl-2 inhibitor has been demonstrated to be effective against small cell lung cancer xenographs, acute lymphoblastic leukemia and hematologic tumors. ABT-263 appears to most effective in combination therapy with other small molecule inhibitors or with more traditional chemotherapy. Synergistic effects have been documented with YM155, rapamycin, taxanes, etoposide, vincristine, VAP, ritximab, bortezomib and cyclophosphamide. In a panel of pediatric tumors ABT-263 was not effective as a single agent against solid tumors but was highly significant against acute lymphocytic leukemia.

In yet another embodiment, the BH3-mimetic compound may be ABT 737, and therefore, the invention further provide a combined therapy using the antagonist of the invention ARTS, with ABT 263. It should be noted that ABT-737 as used herein is a Bcl-2 inhibitor and is used to mimic the efficiency of molecules targeting the BH3 domain. ABT-737 has been shown to have no effect in tumor types with an over expression of Mcl-1. ABT-737 has been reported as been effecting in the inhibition of hematopoietic cell lines, in overcoming resistance in Burkitt's Lymphoma, overcoming resistance in solid tumors, in small cell lung carcinoma and also in malignant glioma's. Interestingly, it was shown that ABT-737 appears to as effective in Hypoxia conditions compared to normoxia conditions; which has far reach consequences in the treatment of pancreatic and solid tumor cancer. ABT-737 has been investigated in combination with a wide variety of chemotherapy agents and other small molecule inhibitors. It has been reported that ABT-737 is synergistic when combined with a JAK-1 inhibitor. In addition ABT-737 has sensitized resistant cell lines to the action of GDC-0941, Sorafenib, Fenretinide, gemcitabine, actinomycin D and ABT-263 to name but a few of the combinations tested. To date no phase 1 or phase 2 trials have been reported for the single use of ABT-737 but in combination treatments it has demonstrated potent anti-myeloma activity with Melphalan and Dexamethasone.

In further embodiments, the BH3 mimetic compound that may be applicable for the invention may include at least one of the following BH3 mimetics compounds or any combinations thereof, 4-[4-[[2-(4-Chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonylbenzamide (ABT-263), (R)-4-(4-((4'-chloro-[1,1'-biphenyl]-2-yl) methyl)piperazin-1-yl)-N-((4-((4-(dimethylamino)-1-(phenylthio)butan-2-yl)amino)-3-nitrophenyl)sulfonyl)benzamide (ABT-737), 1,1',6,6',7,7'-hexahydroxy-5,5'-diisopropyl-3,3'-dimethyl-[2,2'-binaphthalene]-8,8'-dicarbaldehyde (AT-101), (Z)-2-(2-((3,5-dimethyl-1H-pyrrol-2-yl)methylene)-3-methoxy-2H-pyrrol-5-yl)-1H-indole methane sulfonate (GX15-070), 5-(2-isopropylbenzyl)-N-(4-(2-tert-butylphenylsulfonyl)phenyl)-2,3,4-trihydroxybenzamide (TW-37) or DNA, d(P-thio)(T-C-T-C-C-C-A-G-C-G-T-G-C-G-C-C-A-T, as denoted by SEQ ID NO. 7) (oblimersen sodium).

The enhancing effect of ARTS and BH3-like fragments thereof on the pro-apoptotic activity of BH3-mimetic compounds may be also applicable for the native BH3 containing pro-apoptotic proteins. Therefore, in other embodiments, the invention provides combined use of the BH3-like antagonists of the invention and a member of the Bcl-2 having a pro-apoptotic activity. In more specific embodiments, such pro-apoptotic protein may be any one of Bax, Bak, Bnip3, Nix/Bnip3L, Bid, Noxa, Puma and Bad.

The invention provides pharmaceutical compositions comprising an effective amount of the antagonist of the invention or any combinations thereof with BH3-mimetic compounds or with any pro-apoptotic protein member of the Bcl-2 family. In certain embodiments, the compositions of the present invention can be administered for prophylactic and/or therapeutic treatments. In therapeutic application, compositions are administered to a patient already affected by a Bcl-2 over-expressing disorder (e.g., a Bcl-2 over-expressing proliferative disorder such as lymphoma and leukemia) in an amount sufficient to cure or at least partially arrest the condition and its complications. An amount adequate to accomplish this is defined as a "therapeutically effective dose." Amounts effective for this use will depend upon the severity of the condition and the general state of the patient's own immune system, but generally range from about 0.001 to about 1000 mg/Kg. Single or multiple administrations on a daily, weekly or monthly schedule can be carried out with dose levels and pattern being selected by the treating physician. Additionally, the administration of the compositions of the invention, may be periodic, for example, the periodic administration may be effected twice daily, three time daily, or at least one daily for at least about three days to three months. The advantages of lower doses are evident to those of skill in the art. These include, inter alia, a lower risk of side effects, especially in long-term use, and a lower risk of the patients becoming desensitized to the treatment. In another embodiment, treatment using the compositions of the invention, may be effected following at least 1, 2, 3, 4, 5, 6, 7, 8, 9, 10, 14, 30, 60, 90 days of treatment, and proceeding on to treatment for life.

It should be noted that the treatment of different Bcl-2 over-expressing conditions may indicate the use of different doses or different time periods, these will be evident to the skilled medical practitioner.

For prophylactic applications, the compositions of the invention may include a prophylactic effective amount of the active ingredient. The term "prophylactically effective amount" is intended to mean that amount of a pharmaceutical composition that will prevent or reduce the risk of occurrence or recurrence of the biological or medical event that is sought to be prevented in a tissue, a system, animal or human by a researcher, veterinarian, medical doctor or other clinician. In prophylactic applications, the compositions of the invention are administered to a patient who is at risk of developing the disease state to enhance the patient's resistance. Such an amount is defined to be a "prophylactically effective dose". In this use, the precise amounts again depend upon the patient's state of health and general level of immunity, but generally range from 0.001 to 1000 mg per dose.

As mentioned herein before, the compositions provided by the invention optionally further comprise at least one pharmaceutically acceptable excipient or carrier. As used herein "pharmaceutically acceptable carrier" includes any and all solvents, dispersion media, coatings and the like. The use of such media and agents for pharmaceutical active substances is well known in the art. Except as any conventional media or agent is incompatible with the active ingredient, its use in the therapeutic composition is contemplated.

The pharmaceutical composition of the invention can be administered and dosed by the methods of the invention, in accordance with good medical practice. More specifically, the compositions used in the methods and kits of the invention, described herein after, may be adapted for administration by systemic, parenteral, intraperitoneal, transdermal, oral (including buccal or sublingual), rectal, topical (including buccal or sublingual), vaginal, intranasal and any other appropriate routes. Such formulations may be prepared by any method known in the art of pharmacy, for example by bringing into association the active ingredient with the carrier(s) or excipient(s).

The phrases "systemic administration," "administered systemically," "peripheral administration" and "administered peripherally" as used herein mean the administration of a compound, drug or other material other than directly into the central blood system, such that it enters the patients system and, thus, is subject to metabolism and other like processes. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

The pharmaceutical forms suitable for injection use include sterile aqueous solutions or dispersions and sterile powders for the extemporaneous preparation of sterile injectable solutions or dispersions. In all cases the form must be sterile and must be fluid to the extent that easy syringeability exists. It must be stable under the conditions of manufacture and storage and must be preserved against the contaminating action of microorganisms, such as bacteria and fungi.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above.

In the case of sterile powders for the preparation of the sterile injectable solutions, the preferred method of preparation are vacuum-drying and freeze drying techniques which yield a powder of the active ingredient plus any additional desired ingredient from a previously sterile-filtered solution thereof.

Pharmaceutical compositions used to treat subjects in need thereof according to the invention generally comprise a buffering agent, an agent who adjusts the osmolarity thereof, and optionally, one or more pharmaceutically acceptable carriers, excipients and/or additives as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof; and vegetable oils. The proper fluidity can be maintained, for example, by the use of a coating, such as lecithin, by the maintenance of the required particle size in the case of dispersion and by the use of surfactants.

Local administration to the area in need of treatment may be achieved by, for example, local infusion during surgery, topical application, direct injection into the specific organ, etc.

Compositions and formulations for oral administration include powders or granules, suspensions or solutions in water or non-aqueous media, capsules, sachets, lozenges (including liquid-filled), chews, multi- and nano-particulates, gels, solid solution, liposome, films, ovules, sprays or tablets. Thickeners, flavoring agents, diluents, emulsifiers, dispersing aids or binders may be desirable.

Pharmaceutical compositions used to treat subjects in need thereof according to the invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general formulations are prepared by uniformly and intimately bringing into association the active ingredients with liquid carriers or finely divided solid carriers or both, and then, if necessary, shaping the product. The compositions may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers. The pharmaceutical compositions of the present invention also include, but are not limited to, emulsions and liposome-containing formulations.

It should be understood that in addition to the ingredients particularly mentioned above, the formulations may also include other agents conventional in the art having regard to the type of formulation in question, for example those suitable for oral administration may include flavoring agents.

In particular embodiments, the unit dosage formulations are those containing a daily dose or sub-dose, as herein above recited, or an appropriate fraction thereof, of an active ingredient.

Enhancing apoptosis by leading to Bcl-2 degradation as shown by the antagonist of the invention, ARTS, have therefore therapeutic applications, specifically for Bcl-2 over-expressing disorders.

Thus, another aspect of the invention relates to a method for treating, inhibiting, preventing, ameliorating or delaying the onset of a Bcl-2 over-expressing pathological disorder. The method of the invention comprises the step of administering to a subject in need thereof a therapeutically effective amount of at least one antagonist of a Bcl-2 prosurvival protein comprising ARTS or any fragment, peptide, analogues and derivatives thereof or any composition comprising the same. It should be noted that a functional fragment or peptide of ARTS that may be used as antagonist of the invention comprises a BH3-like domain.

According to one embodiment, the antagonist used by the method of the invention may comprise ARTS fragment or peptide comprising an amino acid sequence of any one of residues 1-128, 1-148, 106-148, 106-133, 112-148, 106-128, 112-128, 112-133, 106-140 and 1112-126 of ARTS. In more specific embodiments, such BH3-like domain containing fragments or peptides of ARTS used by the invention may comprise the amino acid sequence as denoted by any one of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 35 and SEQ ID NO: 36, respectively.

According to another embodiment such BH3-like antagonist of the invention may antagonize any Bcl-2 prosurvival protein, for example, at least one of Bcl-2, Bcl-xL, Mcl-1, Bcl-w, A1/Bfl-1 and Bcl-B/Bcl2L10.

In yet other embodiments, the BH3-like antagonist of the invention may interact with at least one pro-apoptotic protein member of the Bcl-2 family, thereby enhancing apoptosis. More specifically, such pro-apoptotic member of the Bcl-2 family may be any one of Bax, Bak, Bnip3, Nix/Bnip3L, Bid, Noxa, Puma and Bad.

In certain embodiments, the BH3-like antagonist used by the method of the invention mediates ubiquitin proteasome system (UPS) degradation of said Bcl-2 prosurvival protein, thereby enhancing and inducing apoptosis.

By specifically leading to degradation of Bcl-2, the antagonist of the invention may be specifically applicable for treating disorders characterized by increased expression of Bcl-2. To specifically identify the appropriate sub-population of the patients that may benefit from treatment with the antagonist of the invention (namely, ARTS and fragments thereof comprising a BH3-like domain), the therapeutic method of the invention may further comprise an additional diagnostic step required for the identification of specific subjects (sub-population) suffering from a specific pathologic disorder, leukemia or breast cancer for example, that specifically displaying over-expression of Bcl-2.

Thus, in certain embodiments, the method of the invention may further comprise an additional determination of the Bcl-2 levels in the affected subject, such diagnostic step comprise (a) determining the level of expression of at least one Bcl-2 prosurvival protein in at least one biological sample of the subject to obtain an expression value. The next step (b) involves determining if the expression value obtained in step (a) is any one of, positive or negative with respect to a predetermined standard expression value or to an expression value of said Bcl-2 in a control sample. It should be noted that a positive expression value of said Bcl-2 may indicate that the examined subjects may display a beneficial effect in response to compounds that reduce Bcl-2 levels and therefore, may be administered with the BH3-like antagonist of the invention.

Thus, in more specific embodiments, the invention further provides a method for treating, inhibiting, preventing, ameliorating or delaying the onset of a Bcl-2 over-expressing pathological disorder comprising the step of:

First (a) determining the level of expression of at least one Bcl-2 prosurvival protein in at least one biological sample of said subject to obtain an expression value. In the second step (b) determining if the expression value obtained in step (a) is any one of, positive or negative with respect to a predetermined standard expression value or to an expression value of said Bcl-2 in a control sample. Finally, in step (c) administering to a subject displaying a positive expression value of Bcl-2 as determined in step (b), a therapeutically effective amount of at least one antagonist of a Bcl-2 prosurvival protein comprising ARTS or any BH3-like containing fragment, peptide, analogues and derivatives thereof, or any composition comprising the same.

It should be further noted that optionally, the method of the invention may further comprises the step of determining also the expression level of ARTS. Such information may assist the practitioner in determining the amount of the therapeutic compounds needed for an optimal treatment. This issue will be discussed in more detail herein after. It should be appreciated that the method of the invention may use any of the BH3-like antagonists or any of the compositions described herein.

According to certain embodiments, the methods provided by the invention are applicable for treating any Bcl-2 over-expressing disorder or condition. In specific embodiments, the methods of the invention may be particularly suitable for treating Bcl-2 over-expressing proliferative disorders.

As used herein, "proliferative disorder" is a disorder displaying hyper proliferation. This term means cell division and growth that is not part of normal cellular turnover, metabolism, growth, or propagation of the whole organism. Unwanted proliferation of cells is seen in tumors and other pathological proliferation of cells, does not serve normal function, and for the most part will continue unbridled at a growth rate exceeding that of cells of a normal tissue in the absence of outside intervention. A pathological state that ensues because of the unwanted proliferation of cells is referred herein as a "hyper proliferative disease" or "hyper proliferative disorder." It should be noted that the term "proliferative disorder", "cancer", "tumor" and "malignancy" all relate equivalently to a hyperplasia of a tissue or organ. In general, the compositions and methods of the present invention may be used in the treatment of non-solid and solid tumors.

Malignancy, as contemplated in the present invention may be any one of lymphomas, leukemias, carcinomas, melanomas, myeloma and sarcomas.

Lymphoma is a cancer in the lymphatic cells of the immune system. Typically, lymphomas present as a solid tumor of lymphoid cells. These malignant cells often originate in lymph nodes, presenting as an enlargement of the node (a tumor). It can also affect other organs in which case it is referred to as extranodal lymphoma. Non limiting examples for lymphoma include Hodgkin's disease, non-Hodgkin's lymphomas and Burkitt's lymphoma.

Leukemia refers to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number of abnormal cells in the blood-leukemic or aleukemic (subleukemic).

Carcinoma as used herein refers to an invasive malignant tumor consisting of transformed epithelial cells. Alternatively, it refers to a malignant tumor composed of transformed cells of unknown histogenesis, but which possess specific molecular or histological characteristics that are associated with epithelial cells, such as the production of cytokeratins or intercellular bridges.

Melanoma as used herein is a malignant tumor of melanocytes. Melanocytes are cells that produce the dark pigment, melanin, which is responsible for the color of skin. They predominantly occur in skin, but are also found in other parts of the body, including the bowel and the eye. Melanoma can occur in any part of the body that contains melanocytes.

Sarcoma is a cancer that arises from transformed connective tissue cells. These cells originate from embryonic mesoderm, or middle layer, which forms the bone, cartilage, and fat tissues. This is in contrast to carcinomas, which originate in the epithelium. The epithelium lines the surface of structures throughout the body, and is the origin of cancers in the breast, colon, and pancreas.

Myeloma as mentioned herein is a cancer of plasma cells, a type of white blood cell normally responsible for the production of antibodies. Collections of abnormal cells accumulate in bones, where they cause bone lesions, and in the bone marrow where they interfere with the production of normal blood cells. Most cases of myeloma also feature the production of a paraprotein, an abnormal antibody that can cause kidney problems and interferes with the production of normal antibodies leading to immunodeficiency. Hypercalcemia (high calcium levels) is often encountered.

Further malignancies that may find utility in the present invention can comprise but are not limited to hematological malignancies (including lymphoma, leukemia and myeloproliferative disorders), hypoplastic and aplastic anemia (both virally induced and idiopathic), myelodysplastic syndromes, all types of paraneoplastic syndromes (both immune mediated and idiopathic) and solid tumors (including GI tract, colon, lung, liver, breast, prostate, pancreas and Kaposi's sarcoma. More particularly, the malignant disorder may be lymphoma. Non-limiting examples of cancers treatable according to the invention include hematopoietic malignancies such as all types of lymphomas, leukemia, e.g. acute lymphocytic leukemia (ALL), acute myelogenous leukemia (AML), chronic lymphocytic leukemia (CLL), chronic myelogenous leukemia (CML), myelodysplastic syndrome (MDS), mast cell leukemia, hairy cell leukemia, Hodgkin's disease, non-Hodgkin's lymphomas, Burkitt's lymphoma and multiple myeloma, as well as for the treatment or inhibition of solid tumors such as tumors in lip and oral cavity, pharynx, larynx, paranasal sinuses, major salivary glands, thyroid gland, esophagus, stomach, small intestine, colon, colorectum, anal canal, liver, gallbladder, extraliepatic bile ducts, ampulla of vater, exocrine pancreas, lung, pleural mesothelioma, bone, soft tissue sarcoma, carcinoma and malignant melanoma of the skin, breast, vulva, vagina, cervix uteri, corpus uteri, ovary, fallopian tube, gestational trophoblastic tumors, penis, prostate, testis, kidney, renal pelvis, ureter, urinary bladder, urethra, carcinoma of the eyelid, carcinoma of the conjunctiva, malignant melanoma of the conjunctiva, malignant melanoma of the uvea, retinoblastoma, carcinoma of the lacrimal gland, sarcoma of the orbit, brain, spinal cord, vascular system, hemangiosarcoma and Kaposi's sarcoma.

It must be understood that in certain embodiments, the compositions and methods of the invention may be applicable for any of the proliferative disorders disclosed herein, provided that the specific subject afflicted by the specific disorder over-expresses at least one of the Bcl-2 pro-survival proteins, specifically, Bcl-2. Identification of such specific Bcl-2 over-expressing patients (that form a sub-population of a specific cancerous disease), is provided by the additional diagnostic step discussed herein above.

The methods provided herein involve administration of the antagonist of the invention in a therapeutically effective amount. The term "effective amount" as used herein is that determined by such considerations as are known to the man of skill in the art. The amount must be sufficient to prevent or ameliorate tissue damage caused by Bcl-2 over-expressing proliferative disorders. Dosing is dependent on the severity of the symptoms and on the responsiveness of the subject to the active drug, specifically, the antagonist of the invention. Medically trained professionals can easily determine the optimum dosage, dosing methodology and repetition rates. In any case, the attending physician, taking into consideration the age, sex, weight and state of the disease of the subject to be treated, will determine the dose. Optimal dosing schedules can be calculated from measurements of drug accumulation in the body of the patient. Persons of ordinary skill can easily determine optimum dosages, dosing methodologies and repetition rates. In general, dosage is calculated according to body weight, and may be given once or more daily, weekly, monthly or yearly, or even once every 2 to 20 years. Persons of ordinary skill in the art can easily estimate repetition rates for dosing based on measured residence times and concentrations of the compositions and combined composition of the invention in bodily fluids or tissues. Following successful treatment, it may be desirable to have the patient undergo maintenance therapy to prevent the recurrence of the disease state, wherein the BH3-like antagonist used by the method of the invention is administered in maintenance doses, once or more daily. As use herein "therapeutically effective amount" means an amount of the ARTS or any fragment or peptide thereof comprising the BH3-like domain, a composition comprising the same which provides a medical benefit as noted by the clinician or other qualified observer. Regression of a tumor in a patient is typically measured with reference to the diameter of a tumor. Decrease in the diameter of a tumor indicates regression. Complete regression is also indicated by failure of tumors to reoccur after treatment has stopped.

The present invention provides methods for treating Bcl-2 over-expressing proliferative disorder. The term "treatment or prevention" refers to the complete range of therapeutically positive effects of administering to a subject including inhibition, reduction of, alleviation of, and relief from, proliferative disorder symptoms or undesired side effects of such proliferative disorder related disorders. More specifically, treatment or prevention includes the prevention or postponement of development of the disease, prevention or postponement of development of symptoms and/or a reduction in the severity of such symptoms that will or are expected to develop. These further include ameliorating existing symptoms, preventing-additional symptoms and ameliorating or preventing the underlying metabolic causes of symptoms.

As used herein, "disease", "disorder", "condition" and the like, as they relate to a subject's health, are used interchangeably and have meanings ascribed to each and all of such terms.

The present invention relates to the treatment of subjects, or patients, in need thereof. By "patient" or "subject in need" it is meant any organism who may be affected by the above-mentioned conditions, and to whom the treatment methods herein described are desired, including humans, domestic and non-domestic mammals such as canine and feline subjects, bovine, simian, equine and murine subjects, rodents, domestic birds, aquaculture, fish and exotic aquarium fish. It should be appreciated that the treated subject may be also any reptile or zoo animal. More specifically, the methods and compositions of the invention are intended for mammals. By "mammalian subject" is meant any mammal for which the proposed therapy is desired, including human, equine, canine, and feline subjects, most specifically humans. It should be noted that specifically in cases of non-human subjects, the method of the invention may be performed using administration via injection, drinking water, feed, spraying, oral gavage and directly into the digestive tract of subjects in need thereof. It should be further noted that particularly in case of human subject, administering of the compositions of the invention to the patient includes both self-administration and administration to the patient by another person.

The invention provides methods for treating Bcl-2 overexpressing disorders, and further relates to disorders associated or related to Bcl-2 over-expression. It is understood that the interchangeably used terms "associated" and "related", when referring to pathologies herein, mean diseases, disorders, conditions, or any pathologies which at least one of share causalities, co-exist at a higher than coincidental frequency, or where at least one disease, disorder condition or pathology causes the second disease, disorder, condition or pathology.

Another aspect of the invention relates to the use of a therapeutically effective amount of at least one BH3-like antagonist of a Bcl-2 prosurvival protein comprising ARTS or any fragment, peptide, analogues and derivatives thereof comprising a BH3-like domain, in the preparation of a composition for the treatment of a Bcl-2 over-expressing pathological disorder.

Still further, the invention provides at least one antagonist of a Bcl-2 prosurvival protein comprising ARTS or any fragment, peptide, analogues and derivatives thereof that comprise a BH3-like domain, for use in the treatment of a Bcl-2 over expressing pathological disorder.

It should be noted that any fragment or peptide of ARTS comprising the BH3-like domain of the invention may be used by the invention. More specific embodiments relate to a fragment or peptide of ARTS that comprise the amino-acid sequence as denoted by any one of SEQ ID NO. 10 to 17 and 35 to 36.

Furthermore, it must be understood that any fragment or peptide of ARTS containing the BH3-like domain described herein, may be also considered as a functional fragment. Functional fragment as used herein refers to a fragment or peptide capable of binding to Bcl-2 pro-survival protein. In yet another embodiment, a functional fragment is capable of mediating Bcl-2 degradation and thereby enhancing apoptosis. Such functional fragments or peptides of ARTS may be used for any of the compositions, combined compositions, methods, uses and kits disclosed by the invention.

In addition to extensive side-effects, treatment with chemotherapy alone is limited in that cancer cells often become resistant to a broad spectrum of structurally unrelated chemotherapeutic agents. Such resistance, termed "multidrug resistance" (MDR), is a common problem in the treatment of patients with cancer, and the resistance of tumor cells to chemotherapeutic drugs represents a major problem in clinical oncology. Apoptosis is an important component of the sequence of events during which chemotherapeutic drugs induce an antitumor response, and studies have implicated Bcl2 as having a critical role in anticancer drug-induced apoptosis.

More specifically, over-expression of Bcl-2 and Bcl-$x_L$ confers resistance to multiple chemotherapeutic agents, including alkylating agents, antimetabolites, topoisomerase inhibitors, microtubule inhibitors and anti-tumor antibiotics, and may constitute a mechanism of clinical chemoresistance in certain tumors. Therefore, the compositions and methods of the invention may further be applicable for sensitizing cancerous cells to chemotherapy, Thus, the invention further encompasses compositions and methods enhancing sensitivity of Bcl-2 over-expressing drug-resistant proliferative disorder and thereby, reducing the amount of a chemotherapeutic agent required for treating a patient.

In addition to the optional combination with chemotherapeutic agents, the antagonists of the invention were shown to act sinergestically with the BH3 mimetic compound ABT 263 and thus, may be also useful in combination with BH3-containing pro-apoptic proteins, for example, any member of the Bcl-2 pro-apoptotic family.

Therefore, another aspect of the invention relates to a combined composition comprising a therapeutically effective amount of: (a) any one of at least one BH3 mimetics compound and at least one pro-apoptotic protein member of the Bcl-2 family; and (b) at least one antagonist of a Bcl-2 prosurvival protein comprising ARTS or any BH3-like containing fragment, peptide, analogues and derivatives thereof. It should be appreciated that the combined composition of the invention may comprise further therapeutic agent.

According to one embodiment, the combined composition of the invention may comprise any of the BH3-like antagonists described by the invention.

More specifically, such antagonist used for the combined composition of the invention may comprise ARTS, or any fragment or peptide thereof comprising the amino acid sequence of any one of residues 1-128, 1-148, 106-148, 106-133, 112-148, 106-128, 112-128, 112-133, 106-140 and 112-126 of ARTS.

In more specific embodiments, the ARTS fragment or peptide may comprise an amino acid sequence as denoted by any one of SEQ ID NO: 10, SEQ ID NO: 11, SEQ ID NO: 12, SEQ ID NO: 13, SEQ ID NO: 14, SEQ ID NO: 15, SEQ ID NO: 16 and SEQ ID NO: 17, SEQ ID NO: 35 and SEQ ID NO: 36, respectively.

According to another embodiment such BH3-like antagonist of the invention may antagonize any Bcl-2 prosurvival protein, for example, at least one of Bcl-2, Bcl-xL, Mcl-1, Bcl-w, A1/Bfl-1 and Bcl-B/Bcl2L 10. Moreover, in certain embodiments, the BH3-like antagonists of the invention may enhance apoptosis mediated by a pro-apoptotic protein member of the Bcl-2 family In certain embodiments, the BH3-like antagonist comprised within the combined composition of the invention mediates ubiquitin proteasome system (UPS) degradation of said Bcl-2 prosurvival protein, thereby enhancing/inducing apoptosis.

In certain embodiments, the combined composition of the invention may comprise at least one BH3-mimetics compound. More specifically, such BH3-mimetic compound may be any one of 4-[4-[[2-(4-Chlorophenyl)-5,5-dimethyl-1-cyclohexen-1-yl]methyl]-1-piperazinyl]-N-[[4-[[(1R)-3-(4-morpholinyl)-1-[(phenylthio)methyl] propyl]amino]-3-[(trifluoromethyl) sulfonyl]phenyl] sulfonyl] benzamide (ABT-263), (R)-4-(4-((4'-chloro-[1,1'-biphenyl]-2-yl) methyl)piperazin-1-yl)-N-((4-((4-(dimethylamino)-1-(phenylthio)butan-2-yl)amino)-3-nitrophenyl)sulfonyl)benzamide (ABT-737), 1,1',6,6',7,7'-hexahydroxy-5,5'-diisopropyl-3,3'-dimethyl-[2,2'-binaphthalene]-8,8'-dicarbaldehyde (AT-101), (Z)-2-(2-((3,5-dimethyl-1H-pyrrol-2-yl)methylene)-3-methoxy-2H-pyrrol-5-yl)-1H-indole methanesulfonate (GX15-070), 5-(2-isopropylbenzyl)-N-(4-(2-tert-butylphenylsulfonyl)phenyl)-2,3,4-trihydroxybenzamide (TW-37) or DNA, d(P-thio)(T-C-T-C-C-C-A-G-C-G-T-G-C-G-C-C-A-T, as denoted by SEQ ID NO. 7) (oblimersen sodium).

In yet another embodiment, the combined composition of the invention may comprise at least one Bcl-2 pro-apoptotic protein. Such protein may be any one of Bax, Bak, Bnip3, Nix/Bnip3L, Bid, Noxa, Puma and Bad.

According to some embodiments, the combined composition of the invention may be a pharmaceutical composition for treating, inhibiting, preventing, ameliorating or delaying the onset of a Bcl-2 over-expressing pathological disorder. Such composition optionally further comprises at least one pharmaceutically acceptable carrier, diluent or excipient.

The phrase "combination therapy" or "adjunct therapy" or in defining use of a compound described herein, specifically, the antagonist of the invention that comprises ARTS or any fragments thereof that comprise a BH3-like domain, and one or more other active pharmaceutical agents, specifically, the BH3-mimetic compounds and/or Bcl-2 pro-apoptotic proteins, is intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations for each agent.

Another aspect of the invention further relates to a method for treating, inhibiting, preventing, ameliorating or delaying the onset of a Bcl-2 over-expressing pathological disorder combining the therapeutic use of the antagonists of the invention with BH3-mimetics compounds or BH3-containing pro-apoptotic protein member of the Bcl-2 family. Thus, such method comprises the step of administering to a subject being treated with at least one BH3-mimetics compound a therapeutically effective amount of at least one antagonist of a Bcl-2 prosurvival protein comprising ARTS or any fragment, peptide, analogues and derivatives thereof that comprise a BH3-like domain.

Still further, the invention provides the use of a therapeutically effective amount of at least one BH3-like antagonist of a Bcl-2 prosurvival protein comprising ARTS or any fragment, peptide, analogues and derivatives thereof for the preparation of a composition for the treatment of a Bcl-2 over-expressing pathological disorder in a subject being treated with at least one BH3-mimetics compound.

It should be noted that according to some embodiments, ARTS and any fragments or peptides thereof used by the invention comprise a BH3-like domain. Non-limiting examples for peptides or fragments of ATRS are provided by the peptides of any one of SEQ ID NO. 9 to 17, 35 and 36.

In certain embodiments, the invention further encompasses the use of the BH3-like antagonists of the invention for treating patients treated with at least one BH3-containing pro-apoptotic protein member of the Bcl-2 family, for example, any one of Bax, Bak, Bnip3, Nix/Bnip3L, Bid, Noxa, Puma and Bad.

The invention further provides at least one BH3-like antagonist of a Bcl-2 prosurvival protein comprising ARTS or any fragment or peptide thereof that comprises a BH3-like domain or any analogues and derivatives thereof for use in the treatment of a Bcl-2 over expressing pathological disorder in a subject being treated with at least one BH3 mimetics compound or with at least one BH3-containing Bcl-2 pro-apoptotic protein.

As noted above, the present invention involves the use of different active ingredients, for example, the BH3-like antagonist of the invention, specifically ARTS and any fragments or peptides thereof that comprises a BH3-like domain, and at least one BH3-mimetic agent or Bcl-2 pro-apoptotic protein that may be administered through different routes, dosages and combinations. More specifically, the treatment of Bcl-2 over-expressing diseases and conditions with a combination of active ingredients may involve separate administration of each active ingredient. Therefore, a kit providing a convenient modular format of the antagonist of the invention, specifically, ARTS and different peptide thereof comprising a BH3-like domain and agents required for treatment would allow the required flexibility in the above parameters.

Thus, in another aspect, the invention provides a kit. In some embodiments, the kit of the invention may include at least two separate pharmaceutical compositions that are required for modulating, and specifically enhancing apoptotic process. According to certain embodiments, the kit of the invention may comprise (a) at least one antagonist of a Bcl-2 prosurvival protein comprising ARTS or any fragment or peptide thereof that comprises a BH3-like domain or analogues and derivatives thereof, optionally, in a first unit dosage form; and (b) any one of at least one BH3 mimetics compound, at least one pro-apoptotic protein member of the Bcl-2 family and any combinations thereof, and a pharmaceutically acceptable carrier or diluent, optionally, in a second unit dosage form.

According to one embodiment, the BH3-like antagonist used for the kit of the invention may comprise ARTS fragment or peptide comprising an amino acid sequence of any one of residues 1-128, 1-148, 106-148, 106-133, 112-148, 106-128, 112-128, 112-133, 106-140 and 112-126 of ARTS. According to another specific embodiment, the antagonist used for the kit of the invention may comprise peptide or fragments of ARTS comprising an amino acid sequence as denoted by any one of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 35 and SEQ ID NO: 36, respectively, and any derivatives thereof.

According to another embodiment, the BH3 mimetics agent used for the kit of the invention may comprise at least one of the following BH3 mimetics compounds or any combinations thereof, 4-[4-[[2-(4-Chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl] benzamide (ABT-263), (R)-4-(4-((4'-chloro-[1,1'-biphenyl]-2-yl)methyl)piperazin-1-yl)-N-((4-((4-(dimethylamino)-1-(phenylthio)butan-2-yl)amino)-3-nitrophenyl)sulfonyl) benzamide (ABT-737), 1,1',6,6',7,7'-hexahydroxy-5,5'-diisopropyl-3,3'-dimethyl-[2,2'-binaphthalene]-8,8'-dicarbaldehyde (AT-101), (Z)-2-(2-((3,5-dimethyl-1H-pyrrol-2-yl)methylene)-3-methoxy-2H-pyrrol-5-yl)-1H-indole methane sulfonate (GX15-070), 5-(2-isopropylbenzyl)-N-(4-(2-tert-butylphenylsulfonyl)phenyl)-2,3,4-trihydroxybenzamide (TW-37) or DNA, d(P-thio)(T-C-T-C-C-C-A-G-C-G-T-G-C-G-C-C-A-T, as denoted by SEQ ID NO. 7) (oblimersen sodium).

In yet another embodiment, the pro-apoptotic protein member of the Bcl-2 family used for the kit of the invention may comprise at least one of Bax, Bak, Bnip3, Nix/Bnip3L, Bid, Noxa, Puma and Bad.

It should be appreciated that each of the multiple components of the kit may be administered simultaneously.

Alternatively, each of said multiple dosage forms may be administered sequentially in either order.

More specifically, the kits described herein can include a composition as described, or in separate multiple dosage unit forms, as an already prepared liquid topical, nasal or oral dosage form ready for administration or, alternatively, can include the composition as described as a solid pharmaceutical composition that can be reconstituted with a solvent to provide a liquid dosage form. When the kit includes a solid pharmaceutical composition that can be reconstituted with a solvent to provide a liquid dosage form (e.g., for oral administration), the kit may optionally include a reconstituting solvent. In this case, the constituting or reconstituting solvent is combined with the active ingredient to provide liquid dosage forms of each of the active ingredients or of a combination thereof. Typically, the active ingredients are soluble in so the solvent and forms a solution. The solvent can be, e.g., water, a non-aqueous liquid, or a combination of a non-aqueous component and an aqueous component. Suitable non-aqueous components include, but are not limited to oils, alcohols, such as ethanol, glycerin, and glycols, such as polyethylene glycol and propylene glycol. In some embodiments, the solvent is phosphate buffered saline (PBS).

As shown by Example 7, ARTS is required for induction of apoptosis by ABT-263 that is a known BH3-mimetic antagonist of Bcl-2. More specifically, as shown by the invention, in the absence of ARTS, ABT263 was not able to induce apoptosis. Thus, by using ARTS as a diagnostic marker, the potential responsiveness of a certain subject to a specific BH3-mimetic may be evaluated and assist determination of a personalized treatment specific for a certain subject. More specifically, subjects that express ARTS may respond to BH3-mimetic compounds, whereas subjects that do not express ARTS may not respond to BH3-mimetic treatment. The method of the invention provides therefore the use of ARTS as a biomarker for predicting and evaluating the effect of a BH3 mimetic agent, specifically, the ABT antagonists (i.e., ABT 263, ABT 737), on a patient and thereby determining the efficacy of a suggested treatment on a particular patient.

Thus, a further aspect of the invention provides a prognostic method for determining the efficacy and assessing responsiveness of a mammalian subject to a BH3 mimetics treatment. The prognostic method of the invention may comprise the following steps. First step (a), involves determining the level of expression of ARTS in at least one biological sample of said subject to obtain an expression value.

The next second step (b), involves determining if the expression value obtained in step (a) is any one of, positive or negative with respect to a predetermined standard expression value or to an expression value of ARTS in at least one control sample. It should be noted that a positive expression value of ARTS indicates that said subject belongs to a pre-established population associated with responsiveness to BH3 mimetics treatment.

In yet another embodiment, ARTS may be also used as a diagnostic tool for predicting and evaluating responsiveness of treatment with BH3-containing Bcl-2 pro-apoptotic proteins.

Determination of a positive or negative expression value may be performed by comparing the expression value obtained in step (a) to a predetermined standard expression value (also referred to herein as a cutoff value) or to an expression value of ARTS in a control sample. Such a step involves calculating and measuring the difference between the expression values of the examined sample and the cutoff value and determining whether the examined sample can be defined as positive or negative. More specifically, as used herein the term "comparing" denotes any examination of the expression level and/or expression values obtained in the samples of the invention as detailed throughout in order to discover similarities or differences between at least two different samples. It should be noted that comparing according to the present invention encompasses the possibility to use a computer based approach.

It should be noted that in certain embodiments, a positive expression value of ARTS in the tested sample indicates that the subject may respond to treatment with a BH3-mimetic antagonist and moreover, may exhibit a beneficial response to the treatment. More specifically, it should be noted that in certain embodiments, the predetermined standard values (cutoff values) are calculated and obtained from populations of subjects suffering from the same Bcl-2 over-expressing condition, specifically, a Bcl-2 over-expressing proliferative condition that responded well to the same BH3-mimetic therapeutic agent, subjects not responding, healthy subjects and untreated subjects. Similarly, where control samples are used instead of, or in addition to predetermined cutoff values, such controls may include subjects suffering from the same proliferative condition that responded well to the same therapeutic agent, subjects not responding, healthy subjects and untreated subjects. Therefore, a positive expression value (when compared to cutoff representing the responder population), reflect ARTS expression (or in some embodiments, high or moderate expression), and indicates that the examined subject belongs to a pre-established population associated with a beneficial response to the specific BH3-mimetic treatment that induces or enhances apoptosis.

In contrast, a negative expression value, that may be a repressed, inhibited, non-existing or low-expression of ARTS, indicates that the examined subject may not respond to said BH3-mimetic treatment and more specifically, may not exhibit a beneficial response to such BH-3 mimetic treatment. Thereby, the method of the invention provides determination of the efficacy of a specific BH-3 mimetic treatment on a specific subject that suffers from a Bcl-2 over-expressing condition, specifically, a Bcl-2 over-expressing proliferative condition.

It should be appreciated that in certain embodiments, the method of the invention may further involve the step of determining Bcl-2 expression levels in a sample. This additional step provides identification of the specific subpopulation of patients that may benefit from such Bcl-2 antagonizing treatment.

As mentioned above, the methods of the invention are based on determining the expression level of a specific biomarker, ARTS, in a sample. The terms "level of expression" or "expression level" are used interchangeably and generally refer to the amount of a polynucleotide or a protein in a biological sample. "Expression" generally refers to the process by which gene-encoded information is converted into the structures present and operating in the cell. Therefore, according to the invention "expression" of a gene, specifically, a gene encoding ARTS may refer to transcription into a polynucleotide, translation into a protein, or even posttranslational modification of the protein. Fragments of the transcribed polynucleotide, the translated protein, or the post-translationally modified protein shall also be regarded as expressed whether they originate from a transcript generated by alternative splicing or a degraded transcript, or from a post-translational processing of the protein, e.g., by proteolysis.

It should be noted that the expression level is reflected by measurement and determination of an expression value. As used herein, the term "expression value", "level of expression" or "expression level" refers to numerical representation of a quantity of a gene product, which herein is a protein, but may also be an mRNA.

The expression value measured for the sample is being determined as "positive" or "negative" with respect to a standard value. "Standard" or a "predetermined standard" as used herein, denotes either a single standard value or a plurality of standards with which the level of ARTS expression from the tested sample is compared. The standards may be provided, for example, in the form of discrete numeric values or is calorimetric in the form of a chart with different colors or shadings for different levels of expression; or they may be provided in the form of a comparative curve prepared on the basis of such standards (standard curve). The standards may be prepared by determining the level of expression of ARTS present in a sample obtained from a plurality of patients that were diagnosed or determined (by other means, for example by a physician, by histological techniques etc.) as performing a beneficial response ("responders") to a certain BH3-mimetic treatment and a population of patients that do not respond well to the same therapeutic agent (non-responders, being correlated with a low level of expression of ARTS). The level of expression for the preparation of the standards may also be determined by various conventional methods known in the art. The methods of the invention may be carried out in parallel to a number of standards of healthy subjects and subjects of different proliferative condition states that respond or not respond to a certain BH3-mimetic treatment and the level determined in the assayed sample is then compared to such standards. After such standards are prepared, it is possible to compare the level of ARTS expression obtained from a specific tested subject to the corresponding value of the standards, and thus obtain an assaying tool.

It should be noted that the term "response", "responsiveness", "responsive" or "responder" to treatment with a specific BH3-mimetic agent refers to an improvement in at least one relevant clinical parameter as compared to an untreated subject diagnosed with the same pathology (e.g., the same type, stage, degree and/or classification of the Bcl-2 over-expressing pathologic condition, specifically, Bcl-2 over-expressing proliferative condition), or as compared to the clinical parameters of the same subject prior to said treatment.

The term "non responder" or "non-responsive" to treatment using a specific BH3-mimetic agent, refers to a patient not experiencing an improvement in at least one of the clinical parameter and is diagnosed with the same condition as an untreated subject diagnosed with the same pathology (e.g., the same type, stage, degree and/or classification of the Bcl-2 over-expressing condition), or experiencing the clinical parameters of the same subject prior to such treatment.

As used herein the phrase "predicting or evaluating efficacy of a treatment" refers to determining the likelihood that a specific treatment using a therapeutic agent is efficient or non-efficient in treating the Bcl-2 over-expressing condition, e.g., the success or failure of the treatment in treating the proliferative condition in a subject in need thereof.

The term "efficacy" as used herein refers to the extent to which the BH3-mimetic treatment produces a beneficial result, e.g., an improvement in one or more symptoms of the pathology (caused by the Bcl-2 over-expressing condition) and/or clinical parameters related to the pathology.

As indicated above, the present aspect of the invention relates to a prognostic method. Prognosis is defined as a forecast of the future course of a disease or disorder, based on medical knowledge. This highlights the major advantage of the instant invention over prior art, namely, the ability to predict the potential responsiveness of a certain subject to a specific BH3-mimetic compound, even prior to treatment. This early prognosis facilitates the selection of appropriate treatment regimens that may minimize undesired non-successful treatment (that in some specific cases involves combined therapy of a BH3-mimetic compound with a chemotherapeutic agent), individually to each patient, as part of a personalized medicine.

Thus, another aspect of the invention relates to a method for determining a BH3 mimetics treatment regimen for a subject suffering from a Bcl-2 over expressing pathological disorder. In certain embodiments, such method comprises the steps of: First in step (a), determining the level of expression of ARTS in at least one biological sample of said subject, to obtain an expression value. Second in step (b), determining if the expression value obtained in step (a) is any one of, positive or negative with respect to a predetermined standard expression value or to an expression value of ARTS in a control sample.

It should be noted that a negative expression value of said ARTS indicates that at least one BH3-like antagonist of the invention comprising ARTS or any fragment or peptide comprising the BH3-like domain, or any analogues and derivatives thereof or any composition comprising the same, may be required for successful treatment in addition to said BH3-mimetics treatment for said subject.

According to one specific embodiment, the BH3-like antagonist of the invention, specifically, ARTS or any fragment thereof comprising a BH3-like domain, may be administered before, after, simultaneously with or any combinations thereof at least one BH3 mimetics compound.

The method of the invention involves determination of the expression levels of ARTS or Bcl-2 in a tested sample. Reference to "determining" as used by the methods of the present invention, includes estimating, quantifying, calculating or otherwise deriving a level of expression of ARTS by measuring an end point indication that may be for example, the appearance of a detectable product.

It should be appreciated that determination of the level of ARTS expression in the biological sample can be effected at the transcriptional level (i.e., mRNA) using detecting molecules that are based on nucleic acids (an oligonucleotide probe or primer), or alternatively, at the translational level (i.e. protein) using amino acid based detecting molecules (such as antibodies), as also demonstrated by the present invention.

In yet further specific embodiments of the invention, the determination of the level of expression of ARTS in a biological sample of the tested subject may be performed by a method comprising the step of contacting detecting molecules specific for ARTS with a biological sample of said subject, or with any nucleic acid or protein product obtained there from.

Thus, according to one specific embodiment, the detecting molecules used by the method of the invention may be isolated detecting amino acid molecules, for example, antibodies, or isolated detecting nucleic acid molecules such as primers or probes or any combinations thereof.

The term "contacting" means to bring, put, incubates or mix together. As such, a first item is contacted with a second item when the two items are brought or put together, e.g., by touching them to each other or combining them. In the context of the present invention, the term "contacting" includes all measures or steps which allow interaction between ARTS and the at least one of the detection molecules specific for ARTS.

It should be noted that certain embodiments of the invention contemplate the use of different biological samples. The term "sample" in the present specification and claims is meant to include biological samples. Biological samples may be obtained from mammal, specifically, a human subject, include fluid, solid (e.g., stool) or tissues. The term "sample" may also include body fluids such as whole blood sample, blood cells, bone marrow, lymph fluid, serum, plasma, urine, sputum, saliva, faeces, semen, spinal fluid or CSF, the external secretions of the skin, respiratory, intestinal, and genitourinary tracts, tears, milk, any human organ or tissue, any biopsy, for example, lymph node or spleen biopsies, any sample taken from any tissue or tissue extract, any sample obtained by lavage optionally of the breast ductal system, plural effusion, samples of in vitro or ex vivo cell culture and cell culture constituents. Some samples that are a priori not liquid are contacted with a liquid buffers which are then used according to the diagnostic method of the invention.

All scientific and technical terms used herein have meanings commonly used in the art unless otherwise specified. The definitions provided herein are to facilitate understanding of certain terms used frequently herein and are not meant to limit the scope of the present disclosure.

As used herein the term "about" refers to ±10% The terms "comprises", "comprising", "includes", "including", "having" and their conjugates mean "including but not limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range. As used herein the term "about" refers to ±10%.

The terms "comprises", "comprising", "includes", "including", "having" and their conjugates mean "including but not limited to". This term encompasses the terms "consisting of" and "consisting essentially of". The phrase "consisting essentially of" means that the composition or method may include additional ingredients and/or steps, but only if the additional ingredients and/or steps do not materially alter the basic and novel characteristics of the claimed composition or method. Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

It should be noted that various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Reagents

Antibodies

The antibodies to the various proteins used herein were purchased from companies as indicated below, and used as instructed by the manufacture. Unless noted otherwise, in all the assays a monoclonal anti-ARTS antibody (Sigma, St. Louis) directed against the unique 27aa C-terminus domain of ARTS was used.

Additionally, anti-Bcl-2 (N-19, sc-492, Santa Cruz), anti-ubiquitin (sc-8017, Santa Cruz), anti-XIAP (#610716, BD), anti-SMAC (#567365, Calbiochem), anti flag (F1804, Sigma), anti-actin (c4, #691001, MP) and matching secondary antibodies were purchased from Jackson laboratories and were used as instructed.

Mammalian Cell Cultures and Treatments

COS-7 and HeLa cells were grown in Dulbecco's modified Eagle medium (DMEM) with 4.5 g/l D-glucose. Media were supplemented with 10% heat inactivated fetal calf serum (FCS), penicillin 100 U/ml, streptomycin 100 µg/ml, sodium pyruvate 1 mM and glutamine 2 mM (Biological Industries, Israel). Knocked-down (KD) ARTS HeLa cells were generated as previously described (Edison et al., 2012b) and grown in the presence of 0.5 mg/ml G418 (Sigma).

The WT and XIAPdRING deficient MEFs were prepared from 14-day old WT and XIAPdRING deficient mouse embryos as previously described (Schile et al., 2008). The WT and XIAP knock-out MEFs were kindly provided by Hermann Steller. (Schile et al, 2008).

Constructs pEF1-AU5 and pEF1-AU5-ARTS constructs containing an AU5 tag attached to the N-terminus of ARTS were designed as previously described (Larisch et al., 2000). The pSC2-6Myc ARTS was generated using PCR as described (Edison et al., 2012b).

The pEBG mammalian expression constructs encoding N-terminus GST fusion proteins together with XIAP or XIAPdelRING were a kind gift from Colin Duckett. HA-8Xubiquitin construct was a kind gift from Aaron Ciechanover (Lotan et al, 2005).

Experimental Procedures

Induction of Apoptosis

To induce apoptosis, COS-7 cells, HeLa cells, MEFs and BT-549 cells were incubated with staurosporine (STS) (Sigma) at the following concentrations 1.75 µM for HeLa, 0.6 µM for BT-549, 1.5 µM for MEFs and 1.25 µM for COS-7 for different time periods. Alternatively, cells were incubated with Etoposide (Sigma) at the following concentrations 200 µM for HeLa, BT-549, COS-7, and immortalized MEFs and 100 µM for primary MEFs for different time periods.

For the proteasome inhibition studies the cells were incubated with MG132 (20 µM) for 6 hours.

Transient Transfection of Cells

For transient transfections jetPEI™ (Polyplus Transfection) and Transfectol (GeneChoice) reagents were used according to the manufacturers' instructions.

Western Blot Analysis

Western blot analysis was performed as described (Lotan et al., 2005). Visualization was performed using LAS4000 luminescent image analyzer (Fujifilm) and densitometry analysis was performed by TotalLab TL100 graphic software.

Binding Assays

Myc Beads Pull-Down Binding Studies

COS-7 cells were co-transfected with different constructs as detailed herein. The cells were lysed in RIPA buffer (150 mM NaCl, 50 mM Tris-HCl (pH 8), 1% NP-40, 0.5% deoxycholate acid containing protease inhibitors (mini Complete, Roche)). The samples were left rotating overnight at 4° C. with the anti-Myc-beads (Santa Cruz). Samples were centrifuged at 4000 rpm, 4° C. for 5 min and washed four times in PBS. Proteins were eluted from beads following 5 min of boiling in sample buffer. Proteins were separate on 12.5% SDS-PAGE gel, followed by Western blot analysis.

Co-Immunoprecipitation

Co immunoprecipitation was performed as previously described (Gottfried et al., 2004). Briefly, 10 µg of anti-ARTS antibody or 2 µg of anti-Bcl-2 or anti-XIAP antibody were added to the protein lysate and the samples were left rotating overnight at 4° C. On the following day, agarose beads conjugated to protein A/G (Santa Cruz) were added for 4 h. Samples were centrifuged at 4000 rpm, 4° C. for 5 min and washed three times with PBS. Proteins were eluted from beads following 5 min of boiling in sample buffer and separated on 12.5% SDS-PAGE gel, followed by Western blot analysis.

Functional-Structural Pull-Down Assays

HeLa cells were transiently transfected with Full length ARTS plasmid and 128 amino acids N' terminus deletion of ARTS plasmid, for 24 hrs. The cells were extracted using RIPA-SDS lysis buffer. Immunoprecipitation was done by incubation of lysates overnight with anti Bcl2 antibody (BD), followed by precipitation done with protein A/G beads (Santa Cruz). Western blot analysis was performed using monoclonal anti ARTS antibody directed against its unique C terminus (Sigma).

Sequence alignment was conducted by using the NCBI web site.

In Vivo Ubiquitination Assay

Cells were transiently transfected with different constructs as detailed herein and treated with MG132 (20 µM, Alexis) for 6 hours. The medium was aspirated and the cells were washed with 1×PBS at room temperature. The cells were scraped at room temperature in 100 µl of denaturation buffer (1% SDS, 140 mM NaCl, 50 mM Tris-HCl pH 7.4) containing protease inhibitor cocktail (Complete, Roche) and 10 mM NEM to preserve ubiquitine chains. The solution was transferred to 2 ml eppendorf tube. The cells were homogenized by passing through a 25-gauge needle (20 times), and boiled for 10 min after vigorous vortexing. An amount of 400 µl of renaturation buffer (2% TritonX-100, 140 mM NaCl, 50 mM Tris-HCl pH 7.4) containing protease inhibitor cocktail (Complete, Roche) and 10 mM NEM was added to the lysate. After 15 min of centrifugation (10,000 g, 4°), the supernatant was transferred into a clean eppendorf tube. The protein concentration was determined using BCA Protein Assay Kit (Pierce). Western blot analyses were performed following immunoprecipitation with particular antibody.

Cell Fractionation Assays

Syringe-Based Subcellular Fractionation

Cells were re-suspended in homogenization buffer [20 mM HEPES-KOH, pH 7.5, 10 mM KCl, 1.5 mM MgCl2, 1 mM sodium EDTA, 1 mM sodium EGTA and 1 mM DTT in the presence of 250 mM sucrose and protease inhibitors (Mini-Complete™, Roche)]. Cell homogenization was performed using a 26 G needle (Sterican® 0.45'25 mm, 26 G'1", Gr.18, B. Braun #46507683) and 1 mL syringe (1 mL HSW NORMJECT®, Henke-Sass, Wolf GmbH #4010.200V0) using 20 strokes. Homogenates were centrifuged at 500×g for 5 min at 4° C., and the supernatant was centrifuged at 10000×g for 20 min to obtain mitochondria. The supernatant was considered as a cytosolic fraction.

Digitonin-Based Subcellular Fractionation

Following induction of apoptosis, cytosolic fraction was generated using a digitonin-based subcellular fractionation technique. Briefly, cells were harvested and centrifuged at 300×g for 10 min, washed in TBS 2.5 mM pH 7.5, and re-pelletted. Cells were permeabilized for 5 min on ice with cytosolic extraction buffer (250 mM sucrose, 70 mM KCl, 137 mM NaCl, 4.3 mM Na2HPO4, 1.4 mM KH2PO4 pH 7.2, 1× complete protease inhibitor cocktail, Roche) containing freshly prepared digitonin (200 μg/ml, D-5628, Sigma). Cytosolic fraction was isolated by collecting the supernatant after centrifugation at 1000×g for 5 min at 4° C. Cytosolic fraction was separated on a 12% acrylamide gel and transferred to nitrocellulose membranes.

Bimolecular Fluorescence Complementation (BiFC) Assay

The Bimolecular Fluorescence Complementation (BiFC) assay, provides a simple and direct way to visualize protein-protein interactions in real-time and in living cells. The method is based on formation of a fluorescent complex through the association of two fragments of a fluorescent protein, brought together by an interaction between proteins fused to the fragments. This method is especially attractive because the Green fluorescent protein (GFP) or Yellow fluorescent protein (YFP) chromophore forms spontaneously on protein folding in virtually every cell type tested (Kerppola, 2006).

Direct binding between [ARTS and Bcl-2] and [XIAP and Bcl-2] was examined using the BiFC system. XIAP was cloned into pBiFC-VN173 (1-172) cloning vector containing part of Venus (a brighter and more photostable variant of YFP). ARTS was cloned into pBiFC-VC155 (155-238) vector containing a completing part of YFP-Venus. Bcl-2 was cloned into pBiFC-VN173 and pBiFC-VC155 vectors to examine the binding with XIAP and ARTS respectively.

Flow Cytometry Analysis

Transfection was performed using 200 ng of each plasmid together with 50 ng of pdsRED plasmid which served as control for transfection efficiency. Thirty six hours later, 1.75 μM STS was added to HeLa cells for the indicated time periods. Cells were trypsinized, washed with PBS and suspended in 0.5 ml PBS/sample. Flow cytometry analyses of cell suspensions were performed using a fluorescence-activated cell sorter (FACSCantoII; BD Biosciences) equipped with an argon laser emitting at 488 nm. Analysis was restricted to live cells. Results were analyzed using FACSDIVA software (BD Biosciences). A ratio between YFP fluorescence and Red fluorescence was calculated for each time point. To determine whether BiFC signal represents specific interactions, the YFP/RFP ration of each time point was compared to that without STS.

Example 1

Bcl-2 Protein Levels are Down-Regulated During Apoptosis Induced by STS and Etoposide Bcl-2 is an anti-apoptiotic factor and thus at the onset of apoptosis, the anti-apoptotic function of Bcl-2 has to be overcome. This usually occurs through interactions between Bcl-2 and the pro-apoptotic members of the Bcl-2 family (Youle and Strasser, 2008).

Figures 1A, 1B:
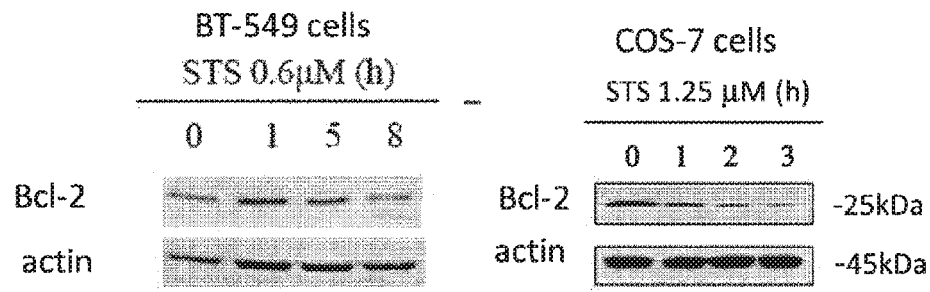

The role of Bcl-2 during apoptosis was studied in different cell lines and under various apoptotic conditions. The results presented in FIG. 1 show that Bcl-2 levels are down regulated upon induction of apoptosis with Staurosporine (STS) or Etoposide in different cell lines and mouse embryonic fibroblasts (MEFs).

These results are in accordance with previous data showing that Bcl-2 levels are down regulated during apoptosis induced by treatment with cisplatin, ursolic acid, Se-methylselenocystein, TNFα and ROS.

Figures 1C, 1D:
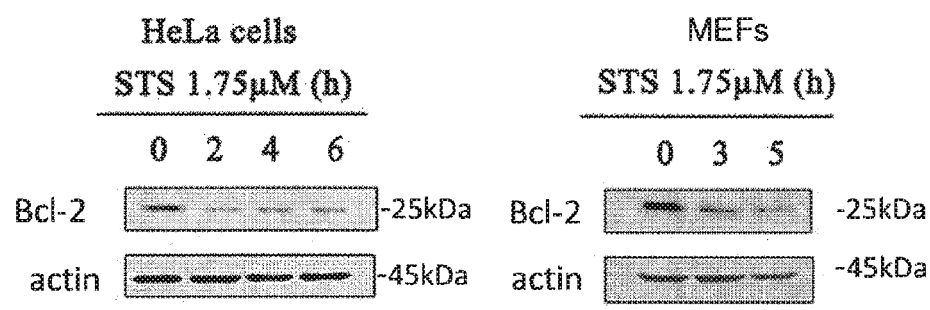
Figures 1E, 1F:
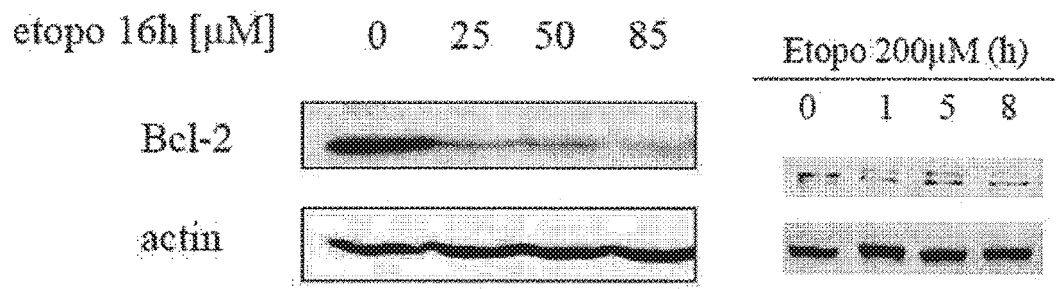

Specifically, FIGS. 1A to 1I display western blots of whole cell lysate using Bcl-2 antibodies. The levels of Bcl-2 that correspond to band at a molecular weight of 25 kDa, were measured and normalized to actin, which serves as an equal loading control and is shown at a molecular weight of 45 kDa. FIGS. 1A to 1D show the effect of Staurosporine (STS) treatment on Bcl-2 levels in BT-549 cells (FIG. 1A), COS-7 cells transiently transfected with Bcl-2 (FIG. 1B), HeLa cells (FIG. 1C) and immortalized MEFs (FIG. 1D).

FIGS. 1E to 1I show the effect of apoptotic induction by Etoposide on the Bcl-1 level in COS-7 cells (FIGS. 1E and 1F), HeLa cells (FIG. 1G), BT-549 cells (FIG. 1H) and primary MEFs (FIG. 1I).

The data presented in FIGS. 1G to 1I was further quantitated by densitometry analyses using Total Lab software, the results of which are shown in FIGS. 1J to 1L, respectively.

Taken together, the results presented in FIG. 1 show a reduction of Bcl-2 levels upon apoptotic induction in all the tested cell lines or MEF. The decrease in Bcl-2 level is observed as early as 1-2 hour following STS and Etoposide treatment and is progression with time.

Bcl-2 Protein Levels are Down-Regulated Via the Ubiquitin-Proteasome System (UPS) During Apoptosis Induced by STS and Etoposide As was previously shown, the ubiquitin-proteasome system (UPS) plays a role in the regulation of apoptosis (reviewed in (Bader and Steller, 2009); Therefore, the inventors next examined whether the observed reduction in Bcl-2 levels involved degradation via UPS.

COS-7 cells transiently transfected with Bcl-2 or co-transfected with Bcl-2 and ARTS constructs were incubated with a potent proteasome inhibitor MG132 for 6 h to evaluate the effect of the ubiquitin-proteasome system (UPS) on Bcl-2 degradation.

Figure 2A:
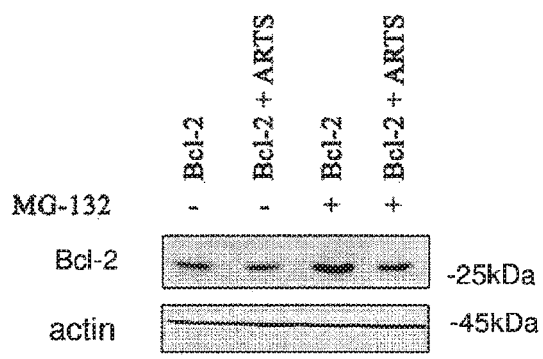
FIGS. 2A-2C. Down-regulation of Bcl-2 levels is mediated by the ubiquitin-proteasome system (UPS)
Figure 2B:
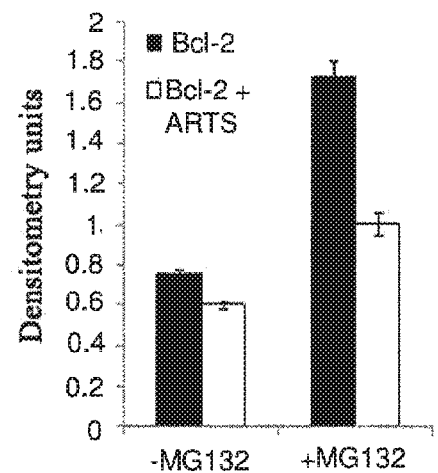

The results in FIGS. 2A and 2B show that there is an accumulation of Bcl-2 levels when cells are treated with proteasome inhibitor, namely, during proteasome inactivation. This suggested that the down-regulation in Bcl-2 levels observed during apoptosis may be mediated by the ubiquitin-proteasome machinery (UPS).

Figure 2C:
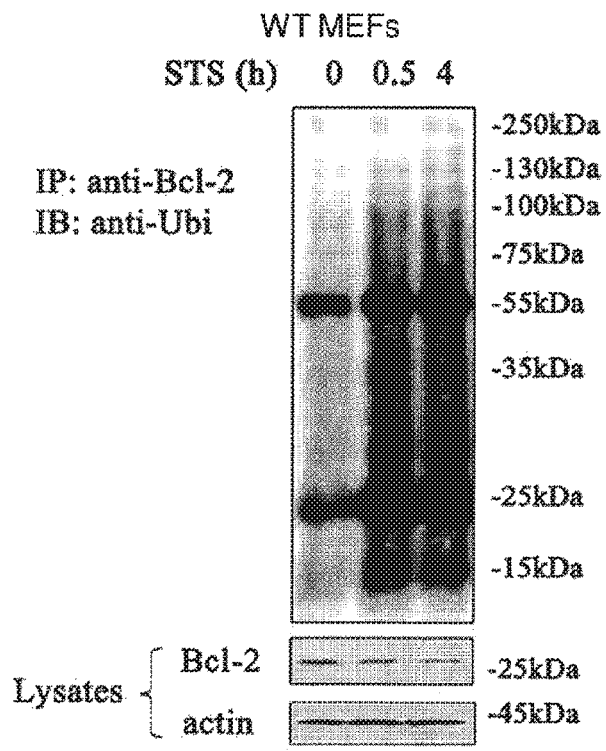

The possible in vivo ubiquitination of Bcl-2 occurring upon apoptotic induction was next tested in immortalized WT MEFs transiently transfected with Bcl-2, XIAP and ubiquitin and treated with 20 μM MG132 for 6 h. Apoptosis was induced using 1.5 μM of STS for the indicated time periods. FIG. 2C shows accumulation of polyubiquitinated forms of Bcl-2 following apoptotic induction with STS. The appearance of Bcl-2 polyubiquitinated forms was seen as early as 30 minutes following treatment with STS. These results suggest that upon induction of apoptosis in cells, Bcl-2 is conjugated to ubiquitin, and thus the levels of Bcl-2 are down-regulated through UPS-mediated degradation.

Example 2

ARTS is Required for Down-Regulation of Bcl-2 Levels

Bcl-2 is known to be localized at the outer membrane of mitochondria (MOM), the endoplasmic reticulum and nuclear envelop (Kaufmann et al., 2003).

To further determine the cellular localization of Bcl-2 under apoptotic and non-apoptotic conditions, Immunofluorescence assay was conducted. HeLa cells were transfected with Bcl-2 and the cells were treated with the apoptotic inducer Staurosporine (STS) for 60 and 180 minutes.

Figure 3A:
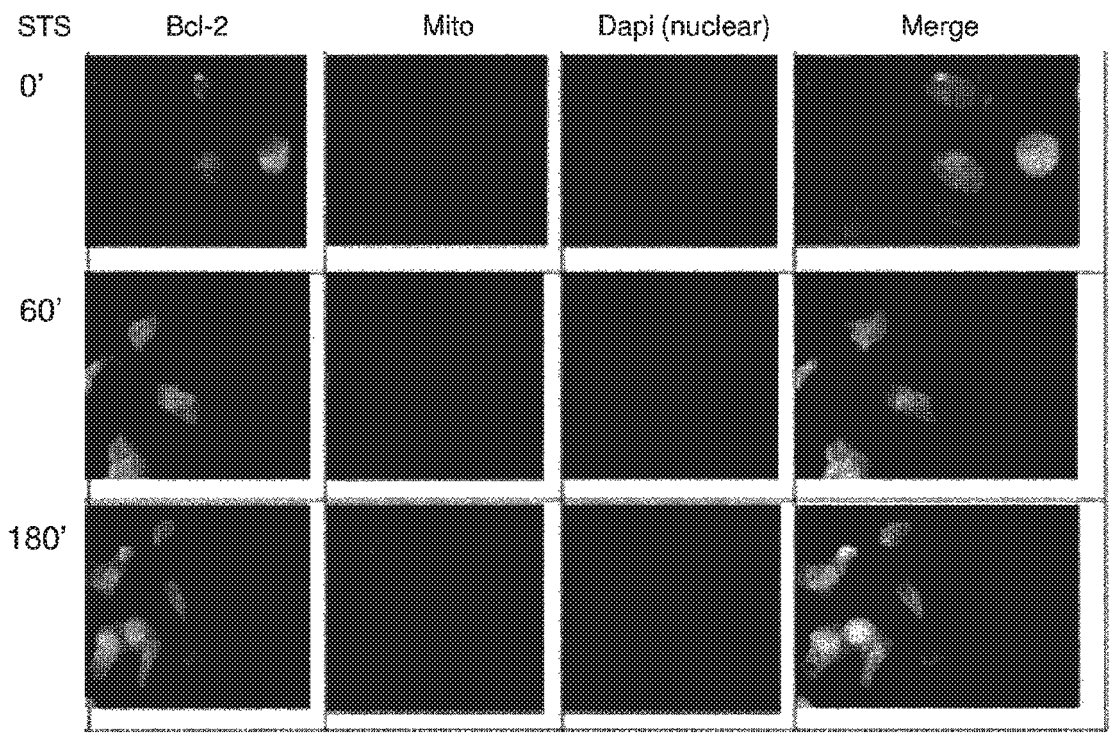
Figure 3B:
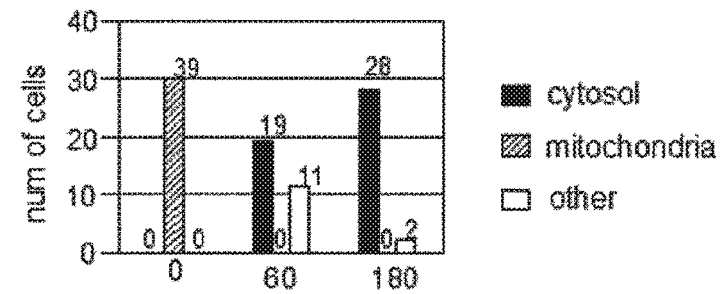
Figure 3C:
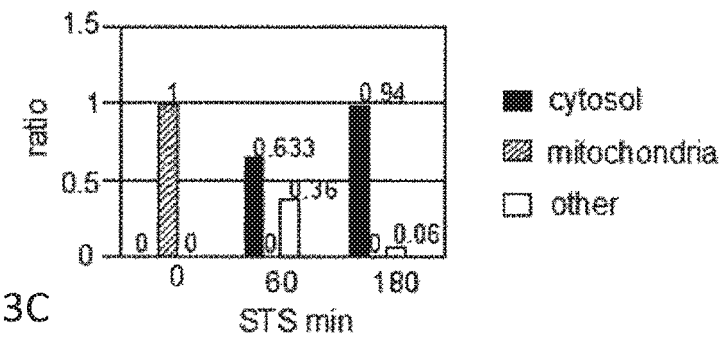

Cells in which Bcl-2 is detected at mitochondria (co-localize with MitoTracker), or at the cytosol (showing diffused pattern of staining) were counted. FIGS. 3A to 3C show that at time 0, all Bcl-2 was localized to the mitochondria. Sixty minutes following STS treatment, 63% of cells exhibited Bcl-2 in their cytosol, and following 180 minutes of STS treatment, most of the cells (94%) exhibited Bcl-2 in the cytosol.

It has been recently shown by some of the inventors that similarly to Bcl-2, ARTS resides at the MOM of living cells (Edison et al., 2012b). Following apoptotic induction, ARTS translocates to the cytosol, prior to MOMP and the release of cytochrome c and Smac, binds XIAP and initiates apoptosis (Edison et al., 2012b). Therefore, localization of Bcl-2 was further determined by fractionation assays in BT-549 (human breast cancer cells) and HeLa (human ovarian carcinoma cells) following apoptotic induction with STS.

FIGS. 3D and 3E show results from BT-549 and HeLa cells, respectively indicating that both, Bcl-2 and ARTS were found in the cytosol as early as 2-15 minutes after apoptosis induction with 0.6 µM STS. In both cell types there is a concomitant appearance of Bcl-2 and ARTS in the cytosol, indicating that Bcl-2 is released to the cytosolic fraction upon apoptotic induction simultaneously to ARTS release.

Moreover, this translocation of both Bcl-2 and ARTS to the cytosol preceded MOMP, as determined from the release of Smac after 20 and 180 minutes (in BT-549 and HeLa cells, FIG. 3D, 3E respectively).

To determine if ARTS plays a role in the translocation of Bcl-2 to the cytosol, the inventors used HeLa cells in which ARTS expression was knocked-down using shRNA method (ARTS KD HeLa) (Edison et al., 2012b). As shown in FIG. 3F, the translocation of Bcl-2 to the cytosol was abrogated in ARTS KD HeLa cells indicating that ARTS is required for the proper translocation of Bcl-2 to the cytosol.

Figure 3I:
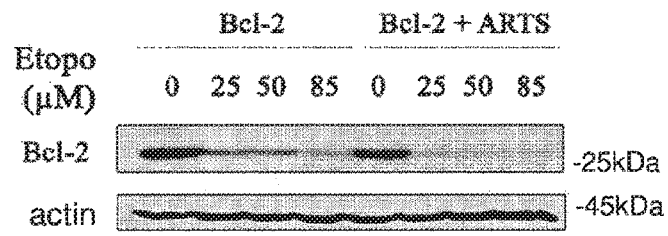
Figure 3J:
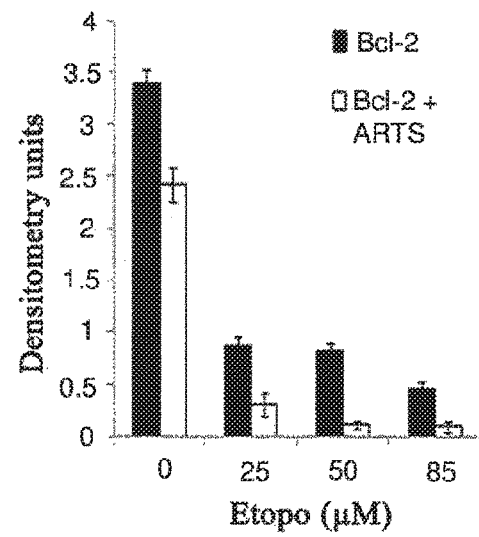

To determine whether ARTS promotes apoptosis by regulating the levels of Bcl-2, the inventors first over-expressed ARTS in COS-7 cells. More specifically, COS-7 cell were transiently transfected with ARTS, Bcl-2 or empty vector or co-transfected with both constructs. As shown in the Western blots and the corresponding Densitometry analyses of FIGS. 3G and 3H, respectively, over expression of ARTS alone was sufficient to cause reduction in Bcl-2 levels. A further reduction of Bcl-2 level was shown upon treatment with Etoposide (FIG. 3I and FIG. 3J).

The role of ARTS in the regulation of Bcl-2 levels was further examined in ARTS KD HeLa cells (Edison et al., 2012b) and MEFs obtained from Sept4/ARTS KO mice (Garcia-Fernandez et al., 2010; Kissel et al., 2005).

Figure 3K:
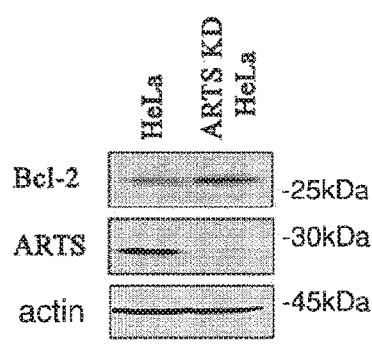
Figure 3L:
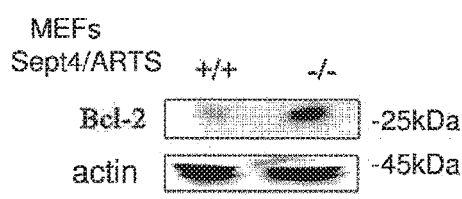
Figure 3M:
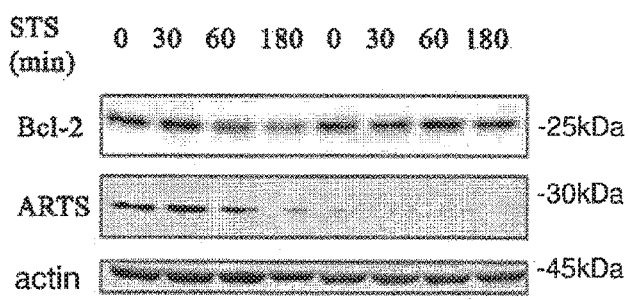

Both ARTS KD HeLa cells, as well as MEFs prepared from Sept4/ARTS KO mice, exhibited a significant increase in the steady state levels of Bcl-2 (FIG. 3K, 3L). This indicates the role of ARTS as a Bcl-2 antagonist in vivo. Importantly, while a decrease in Bcl-2 levels was seen in HeLa cells following 60 and 180 minutes treatments with STS, the levels of Bcl-2 in ARTS KD HeLa cells remained unchanged (FIG. 3M). Taken together, the results suggest that ARTS may function as a novel Bcl-2 antagonist required for down-regulation of Bcl-2 upon induction of apoptosis.

Example 3

Bcl-2, ARTS and XIAP Form a Complex

The mechanism by which ARTS regulates Bcl-2 levels was further tested using a pull-down assay in COS-7 cells which were co-transfected with Bcl-2 and ARTS expression vectors. Pull-down assays were performed using agarose anti-myc beads followed by Western blot analysis using mouse anti-ARTS and anti-Bcl-2 antibodies.

Figure 4A:
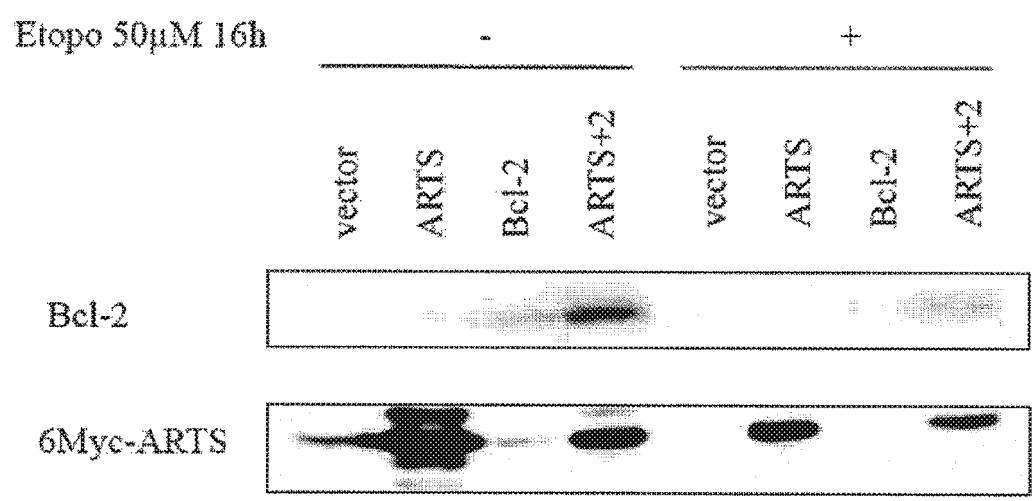

The results presented in FIG. 4A show that ARTS forms a complex with Bcl-2. Interestingly, the complex is degraded upon induction of apoptosis with Etopo.

It has been previously shown by part of the inventors that ARTS binds directly to XIAP and functions as antagonist to XIAP both in vitro and in vivo (Bornstein et al., 2011; Edison et al., 2012a; Garcia-Fernandez et al., 2010; Garrison et al., 2010; Gottfried et al., 2004). XIAP is an E3-ligase and this activity is essential for its anti-apoptotic activity; Schile et al., 2008;).

Because both ARTS and Bcl-2 are localized at the MOM, and since ARTS binds to XIAP, the inventors next examined the possibility that ARTS can bind to both XIAP and Bcl-2.

FIG. 4B presents immunoprecipitation (IP) results using an anti-ARTS monoclonal antibody obtained from HeLa cells, BT-549 cells and COS-7 cells transiently transfected with 6-Myc-ARTS construct indicating that ARTS, Bcl-2 and XIAP form a complex.

Furthermore, as shown in FIGS. 4C and 4D using IP with an anti-XIAP antibody or with an anti-ARTS antibody, respectively, after induction of apoptosis with 1.75 µM STS for 2 h in HeLa cells, XIAP, Bcl-2 and ARTS are found in the same complex.

These results are further supported in HeLa cell using (IP) of endogenous Bcl-2. FIG. 4E shows that a complex is formed between endogenous Bcl-2-ARTS-XIAP after apoptotic induction.

Further understanding and evaluation of the relative contribution of ARTS to the formation of a complex with Bcl-2 and XIAP was obtained by over-expressing ARTS, Bcl-2, and XIAP alone or all together in COS-7 cells, which contain relatively small amounts of endogenous ARTS.

FIGS. 5A and 5B show results of COS-7 cells (pull down and lysates) transiently co-transfected with combinations of ARTS, flag-Bcl-2, and myc-XIAP constructs. Pull-down of XIAP was performed using anti-myc beads, and the precipitate was subjected to western blot analyses. Using anti-flag antibody, a minimal binding of XIAP to Bcl-2 was observed in cells over-expressing only these two proteins (FIG. 5A). This weak binding was attributed to the presence of low endogenous levels of ARTS in these COS-7 cells resulting in almost no formation of the complex. However, over-expression of ARTS significantly increased the ability of XIAP to bind to Bcl-2, suggesting that ARTS facilitates the formation of a complex that includes XIAP and Bcl-2 (FIG. 5A).

To further investigate the binding relationships within this complex, the split-Venus, Bimolecular Fluorescence Complementation (BiFC) system was used. The fluorescence signals were examined using flow cytometry and reflect the relative proximity between the tested proteins. Binding of ARTS to XIAP served as a positive control. Strong binding was observed between ARTS and XIAP and ARTS and Bcl-2 in living cells shortly after apoptotic induction (30 minutes, data not shown). In contrast, only minimal background fluorescence was detected in cells expressing only XIAP and Bcl-2. This suggests that although Bcl-2 can form a complex with XIAP (FIG. 4B, 4C, 4D), Bcl-2 cannot bind directly to XIAP (data not shown) and the presence of ARTS is required. The interaction between ARTS and Bcl-2 as well as ARTS and XIAP decreased during apoptosis (data not shown). This is presumably due to degradation of Bcl-2 upon formation of the ARTS-XIAP-Bcl-2 complex. Collectively, these results suggest that ARTS serves as an adapter to bring Bcl-2 and XIAP into a complex.

Example 5

XIAP Serves as an E3-Ligase for Bcl-2

XIAP is known for its E3-ligase activity that is important for the regulation of apoptosis (Bornstein et al., 2012; Gottfried et al., 2004; Schile et al., 2008). As shown above, ARTS, XIAP and Bcl-2 form a complex that is degraded after induction of apoptosis.

The possibility that the decrease in Bcl-2 levels upon induction of apoptosis may depend on the catalytic activity of XIAP was further studied. For this purpose, over-expression of either XIAP or a mutant lacking its RING domain (XIAPdRING), which abrogated its E3-ligase function, together with Bcl-2 was done in HeLa cells (Schile et al., 2008).

Figure 6A:
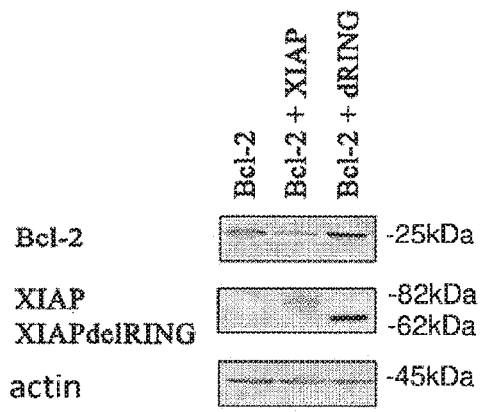
FIG. 6A-6G. XIAP serves as E3-ligase for Bcl-2
Figure 6B:
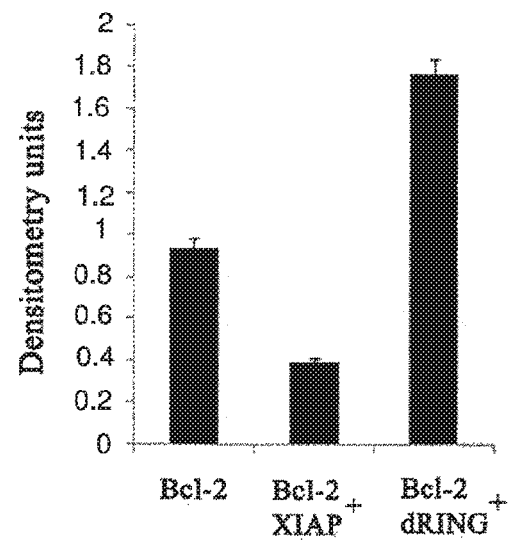

FIGS. 6A and 6B present western blot and densitometry analyses from HeLa cells transiently transfected with Bcl-2 or co-transfected with Bcl-2 and XIAP or Bcl-2 and XIAP-dRING. As shown in FIGS. 6A and 6B, exogenous XIAP reduced the levels of Bcl-2, whereas during co-transfection with XIAPdRING an accumulation of Bcl-2 protein levels was observed suggesting involvement of XIAP in Bcl-2 down-regulation. Further, this suggests that loss of E3-ligase ability of XIAP (mutant) resulted in accumulation of Bcl-2. The same results were shown further in FIG. 7A.

Figure 6C:
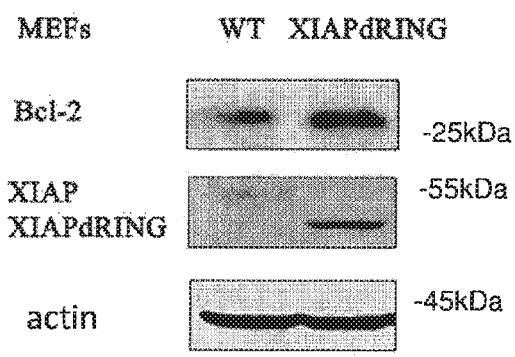
Figure 6D:
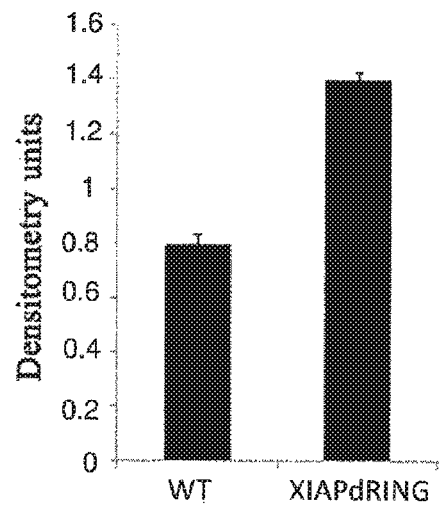

Furthermore, MEFs were produced from WT and XIAP-dRING 14-day old mouse embryos. The Western blot results of whole cell lysates and the corresponding densitometry analyses are shown in FIGS. 6C and 6D. The results show up-regulation of Bcl-2 levels in XIAPdRING MEFs compared to WT XIAP age matched MEFs. These results suggest that the catalytic activity of XIAP is necessary to reduce Bcl-2 levels in MEFs.

Figures 6E, 6F:
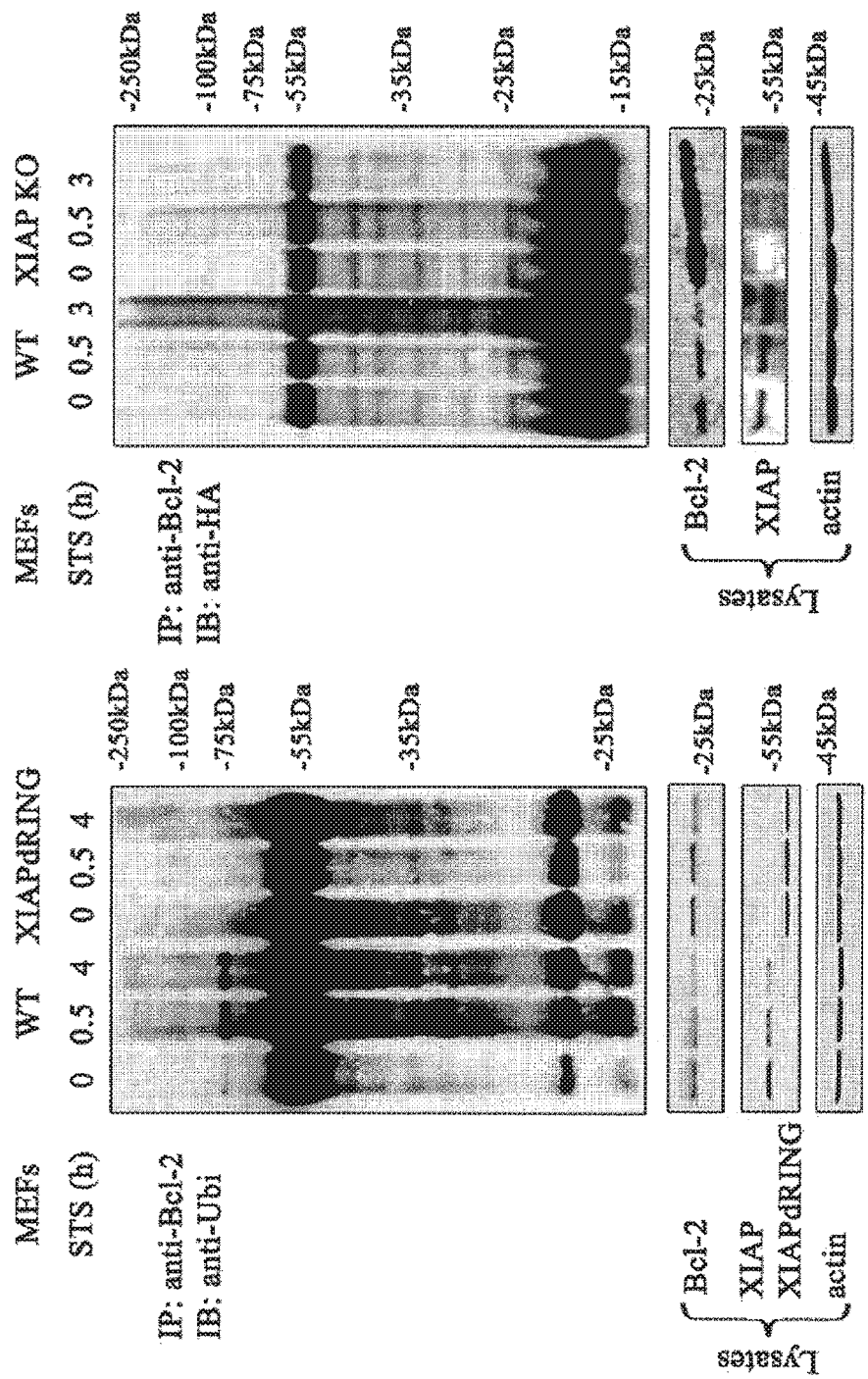

The function of XIAP as an E3-ligase for Bcl-2 was further studied in vivo, where the in vivo ubiquitination of Bcl-2 in WT and XIAPdRING MEFs was compared. FIG. 6E shows accumulation of poly-ubiquitinated forms of Bcl-2 detected at a molecular weight of higher than 26-29 KDa as soon as 30 minutes following apoptotic induction with STS in WT XIAP MEFs, but not in XIAPdRING MEFs.

Similarly, as shown in FIG. 6F, poly-ubiquitinated forms of Bcl-2 detected 180 min following STS induction in WT, but not XIAP knock-out MEFs. These results suggest that the catalytic activity of XIAP is necessary for UPS-mediated degradation of Bcl-2 upon induction of apoptosis, and that XIAP serves as a physiological E3-ligase for Bcl-2. The inventors have further showed that ubiquitination of Bcl-2 takes place in the cytosol (data dot shown).

Figure 6G:
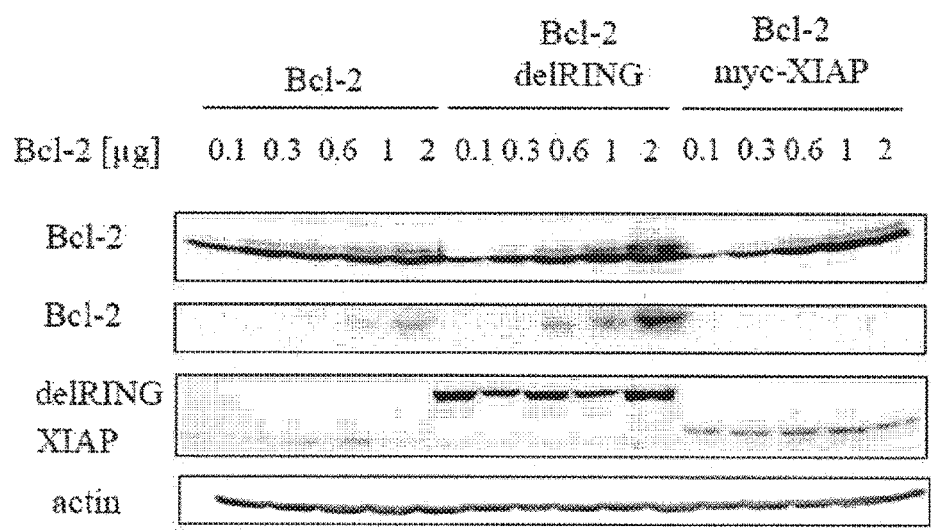

The results are further supported by FIG. 6G that presents data from HeLa cells transiently transfected with different concentrations of Bcl-2 or co-transfected with Bcl-2 and XIAP or Bcl-2 and XIAPARING. The results show that Transfection with XIAPARING resulted in accumulation of Bcl-2 suggesting the involvement of XIAP in Bcl-2 down-regulation.

Example 6

ARTS is Required for the UPS-Mediated Degradation of Bcl-2

Figure 7A:
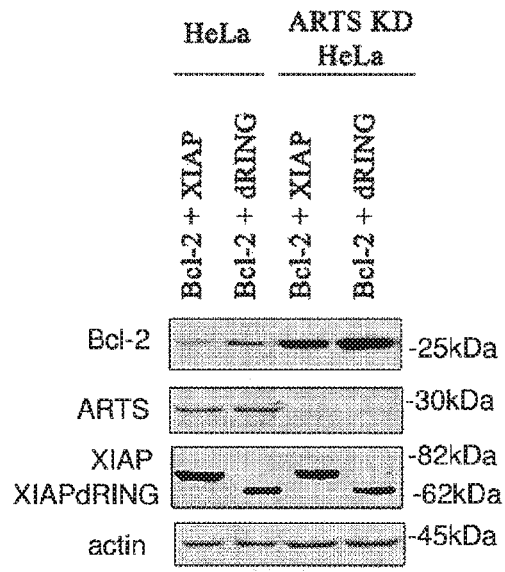
FIG. 7A-7C. ARTS is required for degradation of Bcl-2
Figure 7B:
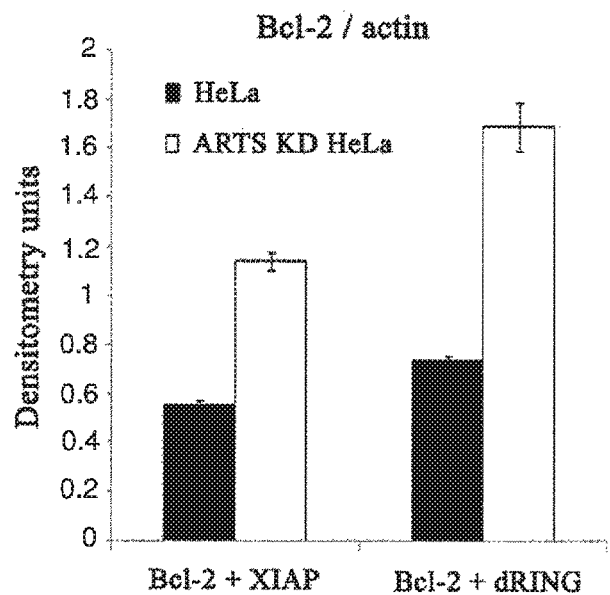

The necessity of ARTS in the UPS-mediated degradation of Bcl-2, was further tested by using HeLa cells and ARTS KD HeLa cells over-expressing Bcl-2 and XIAP, or Bcl-2 and XIAPdRING constructs. FIGS. 7A and 7B show western blot analysis and the respective densitometry analysis and demonstrate an accumulation of Bcl-2 in cells transfected with XIAPdRING. Higher levels of Bcl-2 were observed in HeLa cells over-expressing XIAPdRING compared to WT XIAP.

Even higher levels of Bcl-2 were seen in ARTS KD HeLa cells over-expressing XIAP, with highest Bcl-2 levels found in ARTS KD cells over-expressing XIAPdRING (FIG. 7A, 7B).

These results demonstrate that both ARTS and XIAP E3-ligase activity regulate the levels of Bcl-2.

ARTS plays an important role in initiating apoptosis upstream of MOMP, as was recently demonstrated by part of the inventors (Edison et al., 2012b). In particular, ARTS translocates to the cytosol and binds XIAP as soon as 30 minutes following STS treatment (Edison et al., 2012b). To examine whether ARTS is essential for the early, pre-MOMP ubiquitination and degradation of Bcl-2, in vivo ubiquitination of Bcl-2 as short as 30 minutes following STS treatment was tested in WT and ARTS KD HeLa cells.

More specifically, HeLa or ARTS KD HeLa cells were transiently transfected with Bcl-2, XIAP and ubiquitin and treated with 20 µM MG132 for 6 h. Apoptosis was induced using 1.5 µM of STS for 0.5 h. The cells were harvested and subjected to immunoprecipitation (IP) using anti-Bcl-2 antibodies, followed by immune-blotting (IB) with anti-Bcl-2 antibodies. As demonstrated in FIG. 7C, significant accumulation of poly-ubiquitinated forms of Bcl-2 was seen already 30 minutes after induction of apoptosis in HeLa cells.

This reveals that ubiquitination and degradation of Bcl-2 starts rapidly following apoptotic induction. Moreover, this early degradation of Bcl-2 occurs prior to MOMP and release of cytochrome c and Smac/Diablo that have been recently shown to occur approximately 3 hours after STS treatment (Edison et al., 2012b).

Figure 7C:
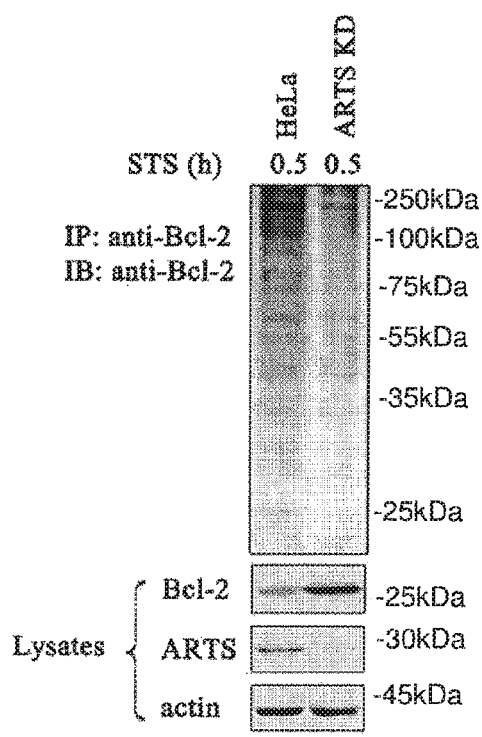

The timing of this ubiquitination is consistent with pre-MOMP function of ARTS (Edison et al., 2012b). Importantly, strong inhibition of Bcl-2 ubiquitination was seen in ARTS KD HeLa cells (FIG. 7C). Thus, it may be proposed that ARTS is required for the early, pre-MOMP ubiquitination of Bcl-2 which leads to UPS-mediated degradation and initiation of apoptosis. Collectively the results provided inhere suggest that ARTS serves as an adaptor protein enabling induced proximity between XIAP and Bcl-2, which allows XIAP to serve as E3-ligase for Bcl-2 to reduce its levels and initiate mitochondrial apoptosis.

Example 7

Interaction Site of Bcl-2 and ARTS

ABT-263 is a Bcl-2 antagonist targeting the BH3 domain and leading to initiation of apoptosis within two hours after treatment. The effect of ABT-263 was studied in HeLa cells and HeLa cells in which ARTS expression was knocked-down using shRNA method (HeLa KD ARTS). HeLa and HeLa KD ARTS cells were treated with different concentrations of ABT-263 at different incubation time points (0, 16 and 24 Hours). Lysates were separated using SDS-PAGE method. To evaluate apoptosis, Western Blot analysis was performed using antibodies recognizing Cleaved-PARP (C-PARP), Cleaved-casp3 (C-Casp3), Bcl-2, ARTS, XIAP and Actin (FIG. 8A).

Figure 8A:
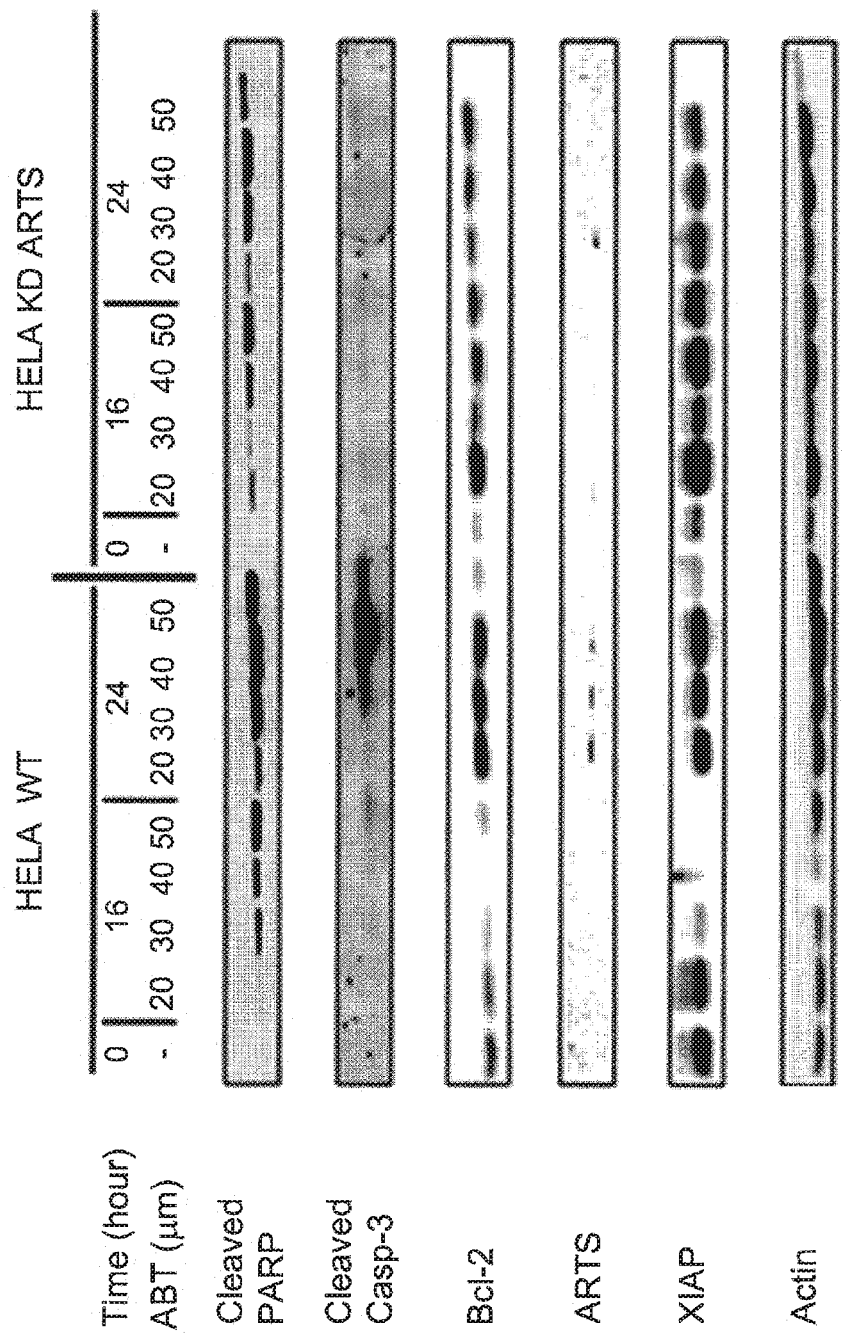
FIG. 8A-8E. Treatment with 25 µM of ABT-263 for 24H results in induction of apoptosis in HeLa cells FIG. 8A. HeLa cells and HeLa cells in which ARTS expression was knocked-down using shRNA method (HeLa KD ARTS were treated with different concentrations of ABT-263 at different incubation time points (0, 16 and 24 Hours). Lysates were separated using SDS-PAGE method. Western Blot analysis was performed using Cleaved-PARP (C-PARP) Cleaved-casp3 (C-Casp3), Bcl-2, ARTS, XIAP and Actin anti-bodies.

As shown in FIG. 8A, optimal induction of apoptosis was seen upon treatment with 25 µM of ABT-263 for 24 h.

Increased concentrations of ABT-263 resulted with increased apoptosis, as seen by higher level of C-PARP and C-Casp3.

Figure 8B:
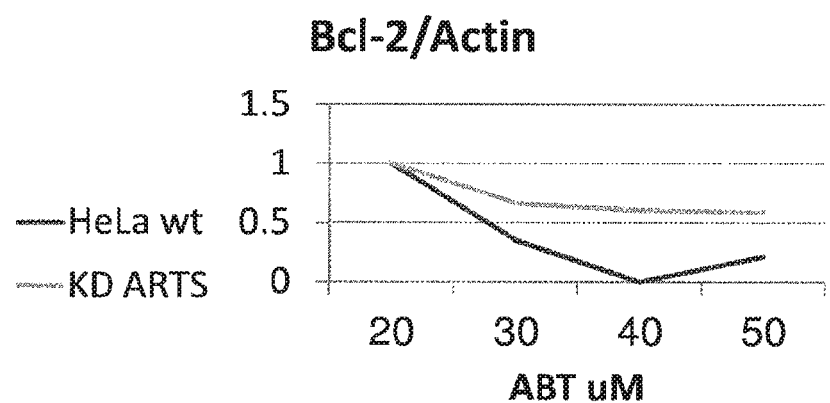
Figure 8C:
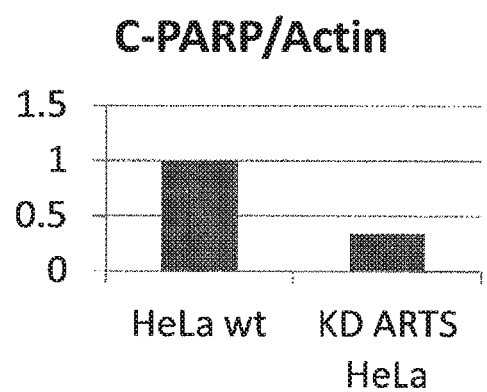
Figure 8D:
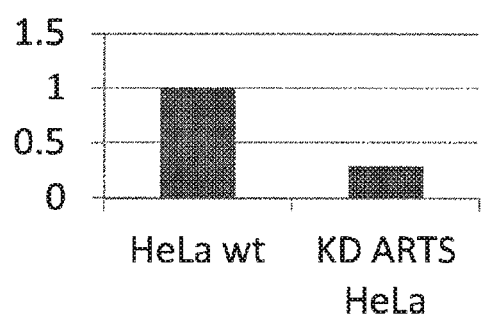
Figure 8E:
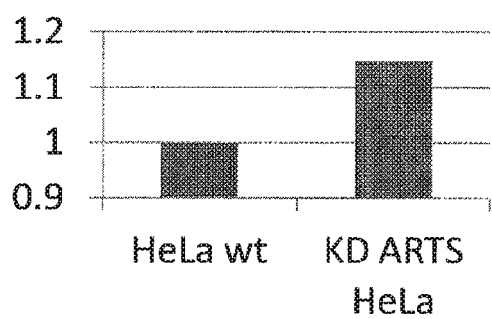

Higher levels of inhibitors of apoptosis, Bcl-2 and XIAP are seen in ARTS KD HeLa cells as compared to wt HeLa cells (FIGS. 8B and 8E). These observed high levels of the anti-apoptotic proteins was associated with lower apoptosis rates as seen by low C-PARP and C-Casp3 levels in the ARTS KD HeLa cells (FIGS. 8C and 8D). Thus, ARTS is required by the BH3 mimetics Bcl-2 antagonist ABT for induction of apoptosis in HeLa cells, through its regulation of both XIAP and Bcl-2.

Figure 9:
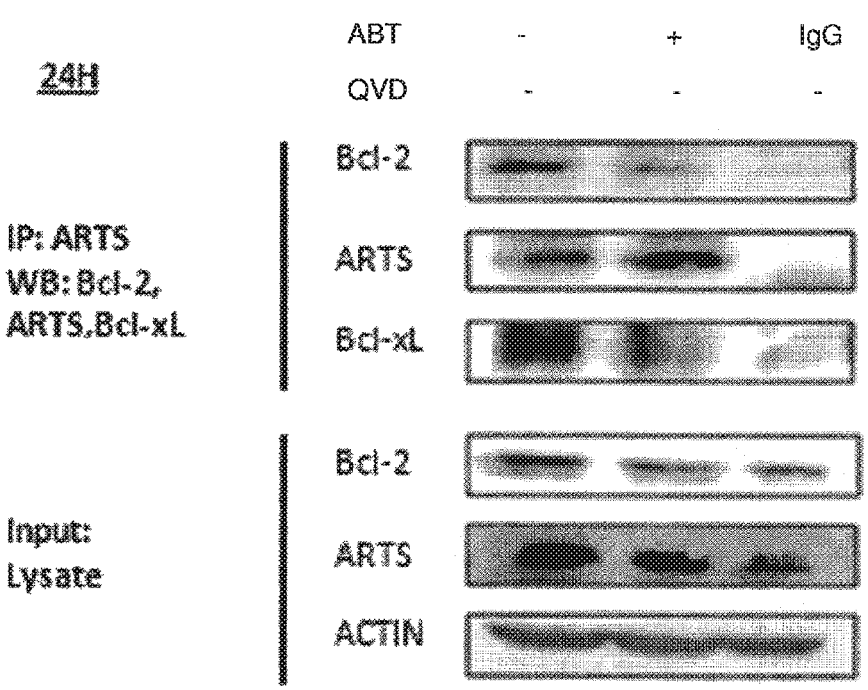
FIG. 9. ARTS binds to Bcl-2 in living cells

Further, HeLa wt cells were treated with ABT-263 25 µM for 24 h. 750 µg of total proteins were subjected to Immunoprecipitation (IP) assay using monoclonal mouse anti ARTS Antibody (Ab). Western Blot analysis was performed using Bcl-2, Bcl-xL, ARTS and Actin antibodies. As can be seen in FIG. 9, ARTS binds to Bcl-2 and Bcl-xL in living cells upstream of caspase activation. This binding is still seen after 24 hours of treatment with ABT-263. The decrease in binding may be the result of lower levels of Bcl-2 and Bcl-xL known to be strongly degraded after 24 hours of apoptosis.

ABT is a known BH3 mimetics antagonist of Bcl-2 that binds the hydrophobic binding groove in Bcl-2 that includes the BH3 domain. In order to examine the mode of action of both, ARTS and the BH3-mimetic compound ABT-263, the ability of ARTS to bind to Bcl-2 was tested after treatment with 25 µM ABT-263 for 3 and 24 hours, in presence or absence of caspase Inhibitor (QVD). Addition of QVD was done to examine whether the binding of ARTS to Bcl-2 occurs before initiation of caspase activation. An IP assay using monoclonal mouse anti ARTS Ab followed by Western Blot was performed by using Bcl-2, ARTS and Actin antibodies. As shown in FIG. 10, following 3 and 24 hours of treatment with ABT-263 in the presence of QVD, a significant increase in binding of ARTS to Bcl-2 is observed, suggesting that ARTS binding to Bcl-2 may not interrupt binding of BH3-mimetic antagonists to Bcl-2.

Moreover, the fact that ARTS and Bcl-2 show higher binding in the presence of ABT under increased apoptosis with QVD indicates that ABT fails to inhibit the binding of ARTS to Bcl-2, and therefore they may target different regions of Bcl-2 (optionally, within the hydrophobic groove). Moreover, the results may indicate that ARTS and BH3-mimetic compounds act via different mechanisms of action to inhibit Bcl-2 and enhance apoptosis. The results further demonstrate that BH3-mimetics antagonists of Bcl-2, such as ABT, require ARTS for inducing apoptosis. As such, the results establish the option of combining BH3-mimetic antagonists of Bcl-2 with ARTS and fragments thereof for enhancing apoptosis.

The present results demonstrates the feasibility of treating Bcl-2 associated disorders by combining BH3-antagonists and the dual antagonist ARTS that target both Bcl-2 and XIAP, allowing for induction of early apoptosis.

Example 8

An N-Terminal Fragment of ARTS is Required for Bcl-2 Binding

In order to identify the Bcl-2 binding domain in ARTS, the inventors examined whether deletion of different fragments of ARTS, namely, the N-terminal 128 amino-acid residues may have an effect. Therefore, pull-down experiments were performed in HeLa cells transfected with either the full length ARTS or a deletion mutant thereof. As shown in FIG. 11, while, both full length (FL) ARTS and the 128aa N'del ARTS are well expressed in the cells (FIG. 11B), only FL ARTS binds to Bcl-2 but the 128aa N'del ARTS does not bind to Bcl-2 (FIG. 11A). These results clearly indicate that deletion of 128 amino acid residues at the N-terminal sequence of ARTS abolished ARTS observed interaction with Bcl-2.

Therefore, it may be suggested that the 128 amino acids at the N-terminus of ARTS are required for Bcl-2 binding.

To further characterize the region of the N' terminal 128 amino acids residues fragment of ARTS, a sequence alignment of this region to Bcl-2 was conducted.

FIG. 12A presents sequence alignment made between the residues 100 to 150 of ARTS residing at the N-terminal portion of ARTS and a fragment of Bcl-2 that comprises the BH3 domain of Bcl-2. FIG. 12B shows sequence alignment of the BH3 region in several Bcl-2 proteins known to include a BH3 domain. As can be seen from FIG. 12A, there is a sequence homology between ARTS and the BH3-core domain in Bcl-2. Moreover, in regions that flank the BH3-core domain, identity of several amino acid residues was also shown, suggesting that ARTS may comprise a BH3-like domain. These results clearly indicate that ARTS interacts and binds Bcl-2 through a BH3-like domain.

TABLE 1 list of sequences

| SEQ ID NO: | Description |
|---|---|
| 1 | cDNA sequence of B-cell CLL/lymphoma 2 (Bcl-2) |
| 2 | cDNA sequence of Bcl-2 |
| 3 | Protein sequence of Bcl-2 |
| 4 | Protein sequence of Bcl-2 |
| 5 | cDNA sequence of B-cell lymphoma-extra large (Bcl-xL) |
| 6 | Protein sequence of Bcl-xL |
| 7 | Artificial sequence (oblimersen sodium, BH3 mimetics) |
| 8 | cDNA sequence of Apoptosis Related Protein in the TGF-beta Signaling Pathway (ARTS) |
| 9 | Protein sequence of ARTS |
| 10 | Protein sequence of ARTS [residues 1-128] |
| 11 | Protein sequence of ARTS [residues 1-148] |
| 12 | Protein sequence of ARTS [residues 106-148] |
| 13 | Protein sequence of ARTS [residues 106-133] |
| 14 | Protein sequence of ARTS [residues 106-128] |
| 15 | Protein sequence of ARTS [residues 112-148] |
| 16 | Protein sequence of ARTS [residues 112-133] |
| 17 | Protein sequence of ARTS [residues 112-128] |
| 18 | Protein sequence of Bad BH3 domain |
| 19 | Protein sequence of Bak BH3 domain |
| 20 | Protein sequence of Bax BH3 domain |
| 21 | Protein sequence of Bid BH3 domain |
| 22 | Protein sequence of Bik BH3 domain |
| 23 | Protein sequence of Bim BH3 domain |
| 24 | Protein sequence of Bok BH3 domain |
| 25 | Protein sequence of Hrk BH3 domain |
| 26 | Protein sequence of Bcl-2 BH3 domain |
| 27 | Protein sequence of Bcl-$X_L$ BH3 domain |
| 28 | Protein sequence of Bcl-W BH3 domain |
| 29 | Protein sequence of Mcl-1 BH3 domain |
| 30 | Protein sequence of ARTS [residues 207-274] |
| 31 | Protein sequence of ARTS [residues 248-274] |
| 32 | Protein sequence of ARTS [residues 266-274] |
| 33 | Protein sequence of ARTS [residues 248-256] |
| 34 | Protein sequence of ARTS [residues 257-265] |
| 35 | Protein sequence of ARTS [residues 106-140] |
| 36 | Protein sequence of ARTS [residues 112-126] |
| 37 | Protein sequence of Bcl-2 [residues 97 to 104] |
| 38 | Protein sequence of Bcl-2 [residues 84 to 124] |
| 39 | Protein sequence of Bcl-2 [residues 84 to 111] |
| 40 | Protein sequence of ARTS [residues 100 to 150] |

The invention claimed is:

1. A method for treating a B-cell lymphoma 2 (Bcl-2) over-expressing pathological disorder, said method comprising the step of administering to a subject in need thereof a therapeutically effective amount of at least one antagonist of Bcl-2 protein comprising a peptide of Apoptosis Related Protein in the TGF-beta Signaling Pathway (ARTS), or any composition comprising the same, wherein said peptide of ARTS comprises a Bcl-2 homology domain 3 (BH3)-like domain and consists of residues 1-128, 1-148, 106-148, 106-128, 106-133, 112-148, 112-128, 112-133, 106-140 or 112-126 of ARTS (SEQ ID NO: 9).

2. The method according to claim 1, wherein said antagonist interacts with Bcl-2 protein, thereby enhancing apoptosis.

3. A method for treating a B-cell lymphoma 2 (Bcl-2) over-expressing pathological disorder in a subject in need thereof, said method comprising the steps of:
   (a) determining the level of expression of said Bcl-2 protein in at least one biological sample of a potential subject to obtain an expression value;
   (b) determining if the expression value obtained in step (a) is any one of positive or negative with respect to a predetermined standard expression value or to an expression value of said Bcl-2 in a control sample;
   (c) identifying the potential subject as a subject in need of treatment for a Bcl-2 over-expressing pathological disorder, if the determination of step (b) is that the expression value obtained in step (a) is positive, and
   (d) administering to said subject identified in step (c) a therapeutically effective amount of at least one antagonist of said Bcl-2 protein comprising a peptide of ARTS or any composition comprising the same, wherein said peptide of ARTS comprises a BH3-like domain and consists of residues 1-128, 1-148, 106-148, 106-128, 106-133, 112-148, 112-128, 112-133, 106-140 or 112-126 of ARTS (SEQ ID NO. 9).

4. A method for inhibiting Bcl-2 over-expression or inducing apoptosis in a subject, said method comprising the step of administering to a subject in need thereof an effective amount of at least one antagonist of Bcl-2 protein comprising a peptide of ARTS, or any composition comprising the same, wherein said peptide of ARTS comprises a Bcl-2 BH3-like domain, and consists of residues 1-128, 1-148, 106-148, 106-128, 106-133, 112-148, 112-128, 112-133, 106-140 or 112-126 of ARTS (SEQ ID NO. 9).

5. A method of claim 4, wherein said method treats a Bcl-2 over-expressing pathological disorder and comprises inhibiting Bcl-2 over-expression or inducing apoptosis in said subject.

6. The method according to claim 5, wherein said subject is one that has been identified by:
   (a) determining the level of expression of said Bcl-2 protein in at least one biological sample of a potential subject to obtain an expression value;
   (b) determining whether the expression value obtained in step (a) is positive or negative with respect to a predetermined standard expression value or to an expression value of said Bcl-2 in a control sample; and
   (c) identifying the potential subject as said subject for said administering step if the determination of step (b) is that the expression value obtained in step (a) is positive.

7. A method for treating a Bcl-2 over-expressing pathological disorder in a subject in need thereof comprising inhibiting Bcl-2 over-expression or inducing apoptosis in said subject, said method comprising the steps of:
   (a) determining the level of expression of ARTS in at least one biological sample of a potential subject, to obtain an expression value;
   (b) determining if the expression value obtained in step (a) is any one of positive or negative with respect to a predetermined standard expression value or to an expression value of ARTS in a control sample;
   (c) identifying the potential subject as a subject if the determination of step (b) is that the expression value obtained in step (a) is negative; and
   (d) administering to said subject identified in step (c) at least one BH3-like antagonist comprising ARTS or any peptide thereof comprising the BH3-like domain, or any composition comprising the same, and at least one BH3 mimetics compound;
   wherein the combination of said antagonist with said BH3 mimetics results in a synergistic effect on induction of apoptosis in said subject, wherein said ARTS peptide consists of residues 1-128, 1-148, 106-148, 106-128, 106-133, 112-148, 112-128, 112-133, 106-140 or 112-126 of ARTS (SEQ ID NO: 9), and wherein BH3 mimetics compound is selected from the group consisting of 4-[4-[[2-(4-chlorophenyl)-5,5-dimethyl-1-cyclohexen-1-yl]methyl]-1-piperazinyl]-N-[ [4-[ [(1R)-3-(4-morpholinyl)-1-[(phenylthio)methyl]propyl] amino]-3-[(trifluoromethyl)sulfonyl]phenyl]sulfonyl]benzamide (ABT-263), (R)-4-(4-((4'-chloro-[1,1'-biphenyl]-2-yl)methyl)piperazin-1-yl)-N-((4-((4-(dimethylamino)-1-(phenylthio)butan-2-yl)amino)-3-nitrophenyl)sulfonyl)benzamide (ABT-737), 1,1',6,6',7,7'-hexahydroxy-5,5'-diisopropyl-3,3'-dimethyl-[2,2'-binaphthalene]-8,8'-dicarbaldehyde (AT-101), (Z)-2-(2-((3,5-dimethyl-1H-pyrrol-2-yl)methylene)-3-methoxy-2H-pyrrol-5-yl)-1H-indole methanesulfonate (GX15-070), and DNA, d(P-thio)(T-C-T-C-C-C-A-G-C-G-T-G-C-G-C-C-A-T (SEQ ID NO. 7)) (oblimersen sodium).

8. The method according to claim 7, wherein said BH3 mimetics compound is 4-[4-[[2-(4-chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl] benzamide (ABT-263).

9. The method according to claim 7, wherein the method further comprises administering a therapeutically effective amount of at least one pro-apoptotic protein member of the Bcl-2 family selected from the group consisting of Bax, Bak, Bnip3, Nix/Bnip3L, Bid, Noxa, Puma and Bad.

10. A method for treating a Bcl-2 over-expressing pathological disorder in a subject, said method comprising the step of administering to said subject a therapeutically effective amount of at least one antagonist of Bcl-2 protein comprising ARTS or any peptide thereof, or any composition comprising the same, simultaneously with at least one BH3-mimetics compound, wherein the combination of said antagonist with said BH3 mimetics compound results in a synergistic effect on induction of apoptosis in said subject, wherein said peptide of ARTS comprises a BH3-like domain and consists of residues 1-128, 1-148, 106-148, 106-128, 106-133, 112-148, 112-128, 112-133, 106-140 or 112-126 of ARTS (SEQ ID NO:9), and wherein said BH3 mimetics compound is selected from the group consisting of 4-[4-[[2-(4-chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl] phenyl]sulfonyl]benzamide (ABT-263), (R)-4-(4-((4'-chloro-[1,1'-biphenyl]-2-yl)methyl)piperazin-1-yl)-N-((4-

((4-(dimethylamino)-1-(phenylthio)butan-2-yl)amino)-3-nitrophenyl)sulfonyl)benzamide (ABT-737), 1,1',6,6',7,7'-hexahydroxy-5,5'-diisopropyl-3,3'-dimethyl-[2,2'-binaphthalene]-8,8'-dicarbaldehyde (AT-101), (Z)-2-(2-((3,5-dimethyl-1H-pyrrol-2-yl)methylene)-3-methoxy-2H-pyrrol-5-yl)-1H-indole methanesulfonate (GX15-070), and DNA, d(P-thio)(T-C-T-C-C-C-A-G-C-G-T-G-C-G-C-C-A-T (SEQ ID NO. 7)) (oblimersen sodium).

11. The method according to claim 10, wherein said BH3 mimetics compound is 4-[4-[[2-(4-chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl]benzamide (ABT-263).

12. The method according to claim 10, wherein said antagonist interacts with Bcl-2 protein, thereby enhancing apoptosis.

13. The method according to claim 10, wherein the method further comprises administering a therapeutically effective amount of at least one pro-apoptotic protein member of the Bcl-2 family selected from the group consisting of Bax, Bak, Bnip3, Nix/Bnip3L, Bid, Noxa, Puma and Bad.

14. The method for treating a Bcl-2 over-expressing pathological disorder in a subject according to claim 10, wherein said method comprises inhibiting Bcl-2 overexpression or inducing apoptosis in said subject, the method comprising the step of administering to said subject a therapeutically effective amount of at least one antagonist of Bcl-2 protein comprising ARTS or any peptide thereof, or any composition comprising the same, and at least one BH3-mimetics compound, wherein the combination of said antagonist with said BH3 mimetics results in a synergistic effect on induction of apoptosis in said subject, wherein said peptide of ARTS comprises a BH3-like domain and consists of residues 1-128, 1-148, 106-148, 106-128, 106-133, 112-148, 112-128, 112-133, 106-140 or 112-126 of ARTS (SEQ ID NO:9), and wherein BH3 mimetics compound is selected from the group consisting of 4-[4-[[2-(4-chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl]benzamide (ABT-263), (R)-4-(4-((4'-chloro-[1,1'-biphenyl]-2-yl)methyl)piperazin-1-yl)-N-((4-((4-(dimethylamino)-1-(phenylthio)butan-2-yl)amino)-3-nitrophenyl)sulfonyl)benzamide (ABT-737), 1,1',6,6',7,7'-hexahydroxy-5,5'-diisopropyl-3,3'-dimethyl-[2,2'-binaphthalene]-8,8'-dicarbaldehyde (AT-101), (Z)-2-(2-((3,5-dimethyl-1H-pyrrol-2-yl)methylene)-3-methoxy-2H-pyrrol-5-yl)-1H-indole methanesulfonate (GX15-070), and DNA, d(P-thio)(T-C-T-C-C-C-A-G-C-G-T-G-C-G-C-C-A-T (SEQ ID NO. 7)) (oblimersen sodium).

15. The method according to claim 14, wherein said BH3 mimetics compound is 4-[4-[[2-(4-chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl]benzamide (ABT-263).

16. The method according to claim 14, wherein the method further comprises administering a therapeutically effective amount of at least one pro-apoptotic protein member of the Bcl-2 family selected from the group consisting of Bax, Bak, Bnip3, Nix/Bnip3L, Bid, Noxa, Puma and Bad.

\* \* \* \* \*